US012624348B2

(12) United States Patent
Schlumpberger et al.

(10) Patent No.: US 12,624,348 B2
(45) Date of Patent: May 12, 2026

(54) ENRICHMENT METHOD

(71) Applicant: QIAGEN GmbH, Hilden (DE)

(72) Inventors: Martin Schlumpberger, Hilden (DE); Karolin Spitzer, Hilden (DE)

(73) Assignee: QIAGEN GmbH, Hilden (DE)

( * ) Notice: Subject to any disclaimer, the term of this patent is extended or adjusted under 35 U.S.C. 154(b) by 860 days.

(21) Appl. No.: 17/785,478

(22) PCT Filed: Dec. 16, 2020

(86) PCT No.: PCT/EP2020/086576
§ 371 (c)(1),
(2) Date: Jun. 15, 2022

(87) PCT Pub. No.: WO2021/122846
PCT Pub. Date: Jun. 24, 2021

(65) Prior Publication Data
US 2023/0028205 A1 Jan. 26, 2023

(30) Foreign Application Priority Data

Dec. 16, 2019 (EP) ..................................... 19216746

(51) Int. Cl.
*C12N 15/10* (2006.01)

(52) U.S. Cl.
CPC ....... *C12N 15/101* (2013.01); *C12N 15/1013* (2013.01)

(58) Field of Classification Search
CPC .......................... C12N 15/101; C12N 15/1013
USPC ....................................................... 536/25.41
See application file for complete search history.

(56) References Cited

U.S. PATENT DOCUMENTS

| | | | |
|---|---|---|---|
| 5,705,628 A | 1/1998 | Hawkins |
| 2001/0014650 A1 | 8/2001 | Smith et al. |
| 2001/0018513 A1 | 8/2001 | Baker |
| 2003/0130499 A1 | 7/2003 | Baker |
| 2011/0319506 A1 | 12/2011 | Erbacher et al. |
| 2012/0245337 A1 | 9/2012 | Fabis et al. |
| 2014/0004601 A1 | 1/2014 | Lim |
| 2014/0227712 A1 | 8/2014 | Horlitz et al. |
| 2015/0353920 A1 | 12/2015 | Enderle et al. |
| 2016/0281078 A1 | 9/2016 | Fabis et al. |
| 2016/0374330 A1 | 12/2016 | Grölz |
| 2017/0016048 A1 | 1/2017 | Blauwkamp et al. |
| 2019/0284548 A1 | 9/2019 | Stoll et al. |
| 2020/0261639 A1 | 8/2020 | Surkov |

FOREIGN PATENT DOCUMENTS

| | | |
|---|---|---|
| DE | 102008063001 A1 | 12/2008 |
| DE | 102008063003 A1 | 12/2008 |
| EP | 2941629 B1 | 10/2018 |
| WO | 9609379 A1 | 3/1996 |
| WO | 9929703 A1 | 6/1999 |
| WO | 0069872 A2 | 11/2000 |
| WO | 0248164 A2 | 6/2002 |
| WO | 2010072821 A1 | 7/2010 |
| WO | 2010072834 A1 | 7/2010 |
| WO | 2012087241 A1 | 6/2012 |
| WO | 2013045432 A1 | 4/2013 |
| WO | 2013045434 A1 | 4/2013 |
| WO | 201410757 A1 | 7/2014 |
| WO | 2015140218 A1 | 9/2015 |
| WO | 2016187234 A1 | 11/2016 |
| WO | 2017197399 A1 | 11/2017 |
| WO | 2019053243 A1 | 3/2019 |
| WO | WO 2019 /218077 | * 11/2019 |

OTHER PUBLICATIONS

International Search Report dated Mar. 23, 2021 filed in PCT/EP2020/086576.

* cited by examiner

*Primary Examiner* — Yih-Horng Shiao
(74) *Attorney, Agent, or Firm* — Rankin, Hill & Clark LLP

(57) ABSTRACT

A method is provided for enriching extracellular DNA from a biological sample comprising extracellular DNA and extracellular vesicles, wherein the method comprises: (a) preparing a binding mixture comprising—the biological sample, —a solid phase comprising anion exchange groups, —an acidic binding buffer comprising a buffering agent, and binding extracellular DNA to the solid phase comprising anion exchange groups; (b) separating the solid phase with the bound extracellular DNA from the remaining binding mixture, wherein the remaining binding mixture comprises extracellular vesicles. The method may furthermore comprise processing the remaining binding mixture to enrich one or more biological targets of interest therefrom, wherein processing may comprise (c) enriching as biological targets extracellular vesicles and/or extracellular RNA from the remaining binding mixture.

33 Claims, 12 Drawing Sheets

ENRICHMENT METHOD

FIELD OF THE DISCLOSURE

The present invention pertains to methods for enriching (i) extracellular DNA and/or (ii) extracellular vesicles and/or extracellular RNA from a biological sample.

BACKGROUND OF THE DISCLOSURE

Extracellular nucleic acids from cell-free biofluids, such as plasma, serum, or urine, represent important analytes for diagnostics and research. Of particular relevance are extracellular nucleic acids, such as extracellular DNA (also referred to as "cell-free" or "cfDNA" herein) and extracellular RNA (also referred to as "cell-free" or "cfRNA" herein). Extracellular RNA is e.g. found in extracellular vesicles (EVs), which contain mRNA and miRNA. The extracellular RNA comprised in extracellular vesicles is also referred to as vesicular RNA. In addition, non-vesicular extracellular RNA exists, which is often associated with proteins (e.g. miRNAs associated with Ago2 proteins) and is thereby protected from degradation.

The efficient capture of extracellular DNA, EVs and/or cfRNA from the same biological sample is challenging and prior art methods often use complex, time consuming workflows or expensive materials (WO 2012/087241, WO 2017/197399 and EP 2941629 B1). Moreover, currently available protocols do not allow to provide cfDNA and cfDNA and/or cfRNA comprising vesicular RNA in separate fractions.

There is an increasing interest and need for further methods for enriching and thus isolating (i) extracellular DNA, (ii) EVs and/or extracellular RNA that comprises vesicular RNA. In particular, there is a need for improved methods, that are more simple than the prior art workflows and allow to provide (i) extracellular DNA and (ii) and/or extracellular RNA as separate fractions. Furthermore, there is a need for methods that can be automated.

It is the object of the present disclosure to provide kits and methods that avoid drawbacks of the prior art. In particular, it is an object to prove a method and kit for enriching (i) extracellular DNA and (ii) EVs and/or extracellular RNA that comprises vesicular RNA

SUMMARY OF THE DISCLOSURE

The present disclosure is based on the finding that extracellular DNA from a biological sample comprising extracellular vesicles can be bound to a solid phase comprising anion exchange groups under conditions, wherein binding of EVs and/or cfRNA to the solid phase is reduced.

As is demonstrated by the examples, the method according to the present disclosure allows to enrich extracellular DNA (also referred to as "cell-free DNA" or "cfDNA") from biological samples comprising extracellular DNA and extracellular vesicles (EVs) (in particular cell-depleted body fluids such as plasma) by selectively binding extracellular DNA to the anion-exchange surface of a solid phase (e.g. magnetic beads) and separating the bound DNA from the remaining binding mixture. During the cfDNA binding step, binding of EVs to the solid phase can be reduced by choice of the binding conditions and the anion exchange groups of the solid phase, in particular by adjusting the acidic pH of the used binding buffer. As is demonstrated by the examples, different buffering agents and anion exchange groups can be used for preferential binding of cfDNA, while binding of EVs or cfRNA (also referred to as "cell-free RNA" or "extracellular RNA") is reduced. In embodiments, at least 50% of the EVs and cfRNA remains in the binding mixture after separation of the solid phase with the bound cfDNA.

The binding conditions according to the present disclosure thus allow to selectively capture extracellular DNA to the anion exchange surface without simultaneously capturing EVs (which contain most of the extracellular RNA) to the same extent to the anion exchange surface. This allows to provide an improved method for isolating extracellular DNA, because RNA contamination can be reduced.

Moreover, these cfDNA selective binding conditions which reduce binding of EVs and cfRNA to the anion exchange surface provides the opportunity for the sequential isolation of different target analytes, e.g. cfDNA in the first binding step, followed by enrichment of EVs and/or total cfRNA in a second binding step. The cfDNA binding conditions used according to the invention advantageously do not promote the destruction of EVs. After separating the solid phase with the bound cfDNA, intact EVs and other analytes such as non-vesicular RNA (e.g. certain miRNAs) are comprised in the remaining binding mixture (e.g. supernatant). The remaining binding mixture can thus be used for isolation of other analytes, such as EVs and/or total cfRNA. This allows to provide cfDNA and vesicular RNA (or total cfRNA comprising vesicular RNA) in separate fractions, facilitating the separate analysis of the obtained fractions (e.g. eluates) using different types of assays. In this way, the present disclosure also provides methods for the sequential enrichment of extracellular DNA and other target analytes, such as the sequential enrichment of ccfDNA and EVs (or EV content), or cfDNA and total cfRNA into separate eluates. Nucleic acids comprised in the EVs can be analyzed independently of the extracellular DNA. This can be highly advantageous, as extracellular DNA and extracellular RNA are oftentimes analyzed differently, e.g. are tested for different types of variants. For example, DNA may be analyzed for single nucleotide variants (SNVs), insertions and deletions (InDels) and, copy number variants (CNVs), while RNA may be analyzed for fusions, exon skipping events and gene expression levels.

Moreover, the herein disclosed sequential isolation of different target analytes allows to further study extracellular nucleic acids. In particular, extracellular vesicles have also been shown to contain genomic DNA fragments from their cells of origin. The methods described in the present disclosure can be used to separate such vesicular DNA from non-vesicular cell-free DNA, thereby allowing separate characterization of both.

Moreover, the method according to the present disclosure allows to use magnetic anion exchange particles as solid phase. This avoids the use of expensive prior art anion exchange membranes that are commonly used for enriching EVs. Furthermore, the use of magnetic anion exchange particles renders the methods according to the present invention automatable. Thus, according to an advantageous embodiment, the solid phase in the extracellular DNA binding step (a) is provided by particles, such as magnetic particles. This allows to perform the methods of the present invention in an automated or semi-automated manner.

According to a first aspect, a method for enriching extracellular DNA from a biological sample comprising extracellular DNA and extracellular vesicles is provided, wherein the method comprises:

(a) preparing a binding mixture comprising
        the biological sample,
        a solid phase comprising anion exchange groups,
        an acidic binding buffer comprising a buffering agent,

and binding extracellular DNA to the solid phase com-
prising anion exchange groups;
(b) separating the solid phase with the bound extracellular
DNA from the remaining binding mixture, wherein the
remaining binding mixture comprises extracellular
vesicles.
The method may further comprise processing the remain-
ing binding mixture to enrich one or more biological targets
of interest therefrom, wherein processing optionally com-
prises
(c) enriching as biological targets extracellular vesicles
and/or extracellular RNA from the remaining binding
mixture.
According to a second aspect, a method for sequentially
enriching (i) extracellular DNA and (ii) extracellular
vesicles and/or extracellular RNA from a biological sample
comprising extracellular DNA and extracellular vesicles is
provided, wherein the method comprises:
(a) preparing a binding mixture comprising
the biological sample,
a solid phase comprising anion exchange groups,
an acidic binding buffer comprising a buffering agent,
and binding extracellular DNA to the solid phase;
(b) separating the solid phase with the bound extracellular
DNA from the binding mixture, wherein the remaining
binding mixture comprises extracellular vesicles; and
(c) enriching extracellular vesicles and/or extracellular
RNA from the remaining binding mixture.
According to a third aspect, a method for enriching
extracellular vesicles and/or extracellular RNA from a bio-
logical sample comprising extracellular vesicles and non-
target biomolecules is provided, the method comprising:
(a) preparing a binding mixture comprising
the biological sample,
a solid phase comprising anion exchange groups,
an acidic binding buffer comprising a buffering agent,
and binding at least extracellular DNA as non-target
biomolecule to the solid phase;
(b) separating the solid phase with the bound extracellular
DNA from the binding mixture, wherein the remaining
binding mixture comprises extracellular vesicles; and
(c) enriching extracellular vesicles and/or extracellular
RNA from the remaining binding mixture.
The method according to the third aspect allows to enrich
EVs and/or extracellular RNA from a biological sample
comprising extracellular vesicles, by first depleting non-
target biomolecules such as extracellular DNA in step (a).
This allows to provide EVs and/or cfRNA with less cfDNA
contamination. Moreover, the method according to this
aspect can be used to deplete non-vesicular nucleic acids
(DNA and/or RNA) released by cell death, e.g. during
sample collection or cell culture, and non-vesicular nega-
tively charged proteins that may otherwise bind to anion
exchange surfaces.
According to a fourth aspect, a kit for performing the
methods according to the present disclosure is provided,
wherein the kit comprises:
(a) a solid phase comprising anion exchange groups for
binding extracellular DNA; and
(b) an acidic binding buffer comprising a buffering agent.
Other objects, features, advantages and aspects of the
present application will become apparent to those skilled in
the art from the following description and appended claims.
It should be understood, however, that the following descrip-
tion, appended claims, and specific examples, while indi-
cating preferred embodiments of the application, are given
by way of illustration only.

4

DETAILED DESCRIPTION

Figure 1A:
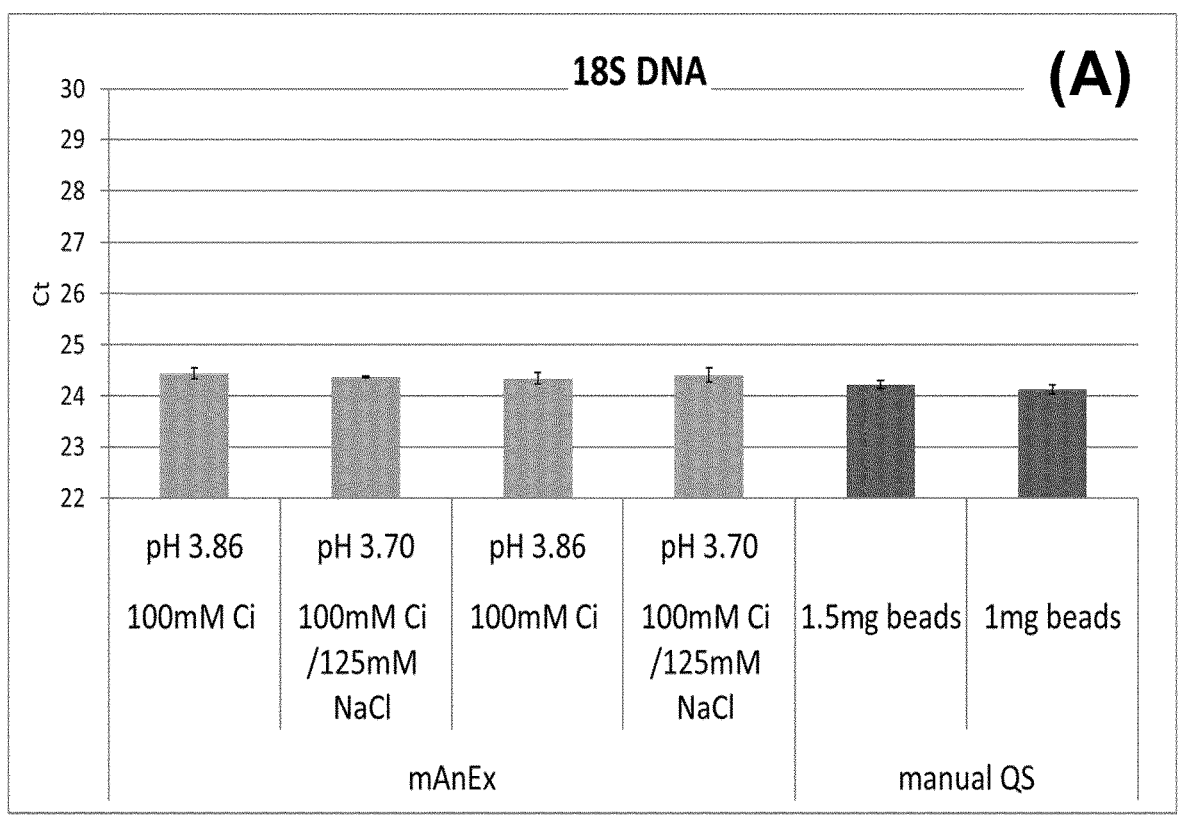
FIG. 1A: Shows results of Example 1, here recovery of
ccfDNA (18S DNA) that was in the first binding step bound
to and eluted from the mAnEx beads using the method
according to the present disclosure. As control, a plasma
sample was processed for isolating cfDNA with an estab-
lished, manual magnetic bead-based protocol using 1.5 or 1
mg beads. Shown are the Ct-values, wherein a lower Ct
value indicates a better recovery.

As is demonstrated by the examples, extracellular DNA (such as ccfDNA) and extracellular vesicles such as exosomes (including their content, such as RNA, in particular mRNA, miRNA, but also potentially other types of RNA, also in form of the total RNA as comprised in exosomes) can be enriched and thus isolated from the same biological sample. The term enrichment is used in a broad sense and inter alia covers the isolation and purification of the target analyte. The workflows described herein enable the parallel analysis of multiple different biological targets.

"Extracellular DNA" and "extracellular RNA" as used herein, in particular refers to DNA and RNA, respectively, that is not contained in cells but is comprised in the extracellular fraction of the biological sample, such as a (cell-containing) bodily fluid sample. In one embodiment, the biological sample is a cell culture supernatant. Generally, extracellular nucleic acids are also often referred to as cell-free nucleic acids, such as cell-free DNA and cell-free RNA. These terms are used as synonyms herein. Cell-free nucleic acids obtained from a circulating bodily fluid (such as blood) are also referred to as circulating cell-free nucleic acids, e.g. ccfDNA or ccfRNA. Extracellular nucleic acids may be enriched from a cell-depleted or cell-free fraction that may be obtained from a cell-containing bodily fluid (e.g. blood plasma or serum, preferably plasma). Examples of typical extracellular nucleic acids that are found in the cell-free fraction of body fluids include but are not limited to mammalian extracellular nucleic acids such as e.g. extracellular tumor-associated or tumor-derived DNA and/or RNA, other extracellular disease-related DNA and/or RNA, epigenetically modified DNA, fetal DNA and/or RNA, small interfering RNA such as e.g. miRNA and siRNA, and non-mammalian extracellular nucleic acids such as e.g. viral nucleic acids, pathogen nucleic acids released into the extracellular nucleic acid population e.g. from prokaryotes (e.g. bacteria), viruses, eukaryotic parasites or fungi. The extracellular nucleic acid population usually comprises certain amounts of intracellular nucleic acids that were released from damaged or dying cells.

The term "extracellular vesicle" (EV) or "extracellular vesicles" (EVs) as used herein in particular refers to any type of secreted vesicle of cellular origin. EVs may be broadly classified into exosomes, microvesicles (MVs) and apoptotic bodies. EVs such as exosomes and microvesicles are small vesicles secreted by cells. EVs have been found to circulate through many different body fluids including blood and urine which makes them easily accessible. Due to the resemblance of EVs composition with the parental cell, circulating EVs are a valuable source for biomarkers. Circulating EVs are likely composed of a mixture of exosomes and MVs. They contain nucleic acids, in particular mRNA, miRNA, other small RNAs protected from degradation by a lipid bilayer. The contents are accordingly specifically packaged, and represent mechanisms of local and distant cellular communications. They can transport RNA between cells. EVs such as exosomes are an abundant and diverse source of circulating biomarkers. The cell of origin may be a healthy cell or a cancer cell. The cell of origin may also be an otherwise disease-affected or affected cell, including a stress-affected cell. For instance, the cell may be affected by a neurodegenerative disease. Another example is a stressed cell, such as a cell that underwent ageing. A stressed cell may release more EVs and extracellular DNA. EVs such as exosomes are often actively secreted by cancer cells, especially dividing cancer cells. As part of the tumor microenvironment, EVs such as exosomes seem to play an important role in fibroblast growth, desmoplastic reactions but also initiation of epithelial-mesenchymal transition (EMT) and SC as well as therapy resistance building and initiation of metastases and therapy resistance. There is thus a high interest in analyzing EVs, respectively EV content such as vesicular RNA.

As disclosed herein, the methods according to the various aspects of the present disclosure are based on the same core principle for selectively enriching extracellular DNA by binding the cfDNA to a solid phase comprising anion exchange groups, wherein binding of EVs and/or cfRNA is reduced under the chosen binding conditions (see in particular the method according to the first aspect). Thus, while cfDNA is efficiently isolated, EVs and cfRNA predominantly remain in the binding mixture and can be subsequently isolated therefrom (see in particular methods according to the second and third aspect).

The Method According to the First Aspect

According to a first aspect, a method for enriching extracellular DNA from a biological sample comprising extracellular DNA and extracellular vesicles is provided, wherein the method comprises:

(a) preparing a binding mixture comprising
   the biological sample,
   a solid phase comprising anion exchange groups,
   an acidic binding buffer comprising a buffering agent,
   and binding extracellular DNA to the solid phase comprising anion exchange groups;
(b) separating the solid phase with the bound extracellular DNA from the remaining binding mixture, wherein the remaining binding mixture comprises extracellular vesicles.

The method according to the first aspect allows to selectively isolate extracellular DNA (in particular circulating, cell-free DNA (ccfDNA)) from a biological sample while depleting extracellular vesicles (EVs) and other extracellular RNA, such as non-vesicular RNA as is demonstrated by the examples. In the method according to the first aspect, binding of extracellular vesicles and other extracellular RNA to the solid phase comprising anion exchange groups in step (a) can be reduced or even eliminated by choice of the binding conditions and the anion exchange groups of the solid phase, in particular by adjusting the acidic pH of the used binding buffer. Extracellular vesicles and other extracellular RNA is thus contained in the remaining binding mixture. This allows to isolate cell-free DNA in a pure form.

Step (a)

Step (a) comprises preparing a binding mixture comprising
   the biological sample,
   a solid phase comprising anion exchange groups,
   an acidic binding buffer comprising a buffering agent,
   and binding extracellular DNA to the solid phase comprising anion exchange groups. Step (a) can be performed in the same manner in the methods according to the first, second and third aspect. Therefore, the disclosure provided herein for step (a) of the method according to the first aspect, also applies with respect to step (a) of the methods according to the second and third aspect.

As disclosed herein, it is preferred to use anion exchange particles, more preferably magnetic anion exchange particles as solid phase. This simplifies the processing of the particles because they can be processed by the aid of a magnet which is advantageous for automation. Thus, the whole disclosure herein that refers to a solid phase comprising anion exchange groups also specifically applies to the preferred embodiment wherein magnetic anion exchange particles are used as solid phase. When using anion exchange particles, such as magnetic anion exchange particles they are not comprised in a column or other device that would prevent the particles from moving in the binding mixture but the particles can move in the binding mixture that is comprised in a vessel, e.g. when the binding mixture is agitated.

The binding mixture comprises an acidic binding buffer comprising a buffering agent. The acidic binding buffer may be contacted with the biological sample and the solid phase in any order. In embodiments, the acidic binding buffer is first mixed with the biological sample and the obtained mixture is then contacted with the solid phase to prepare the binding mixture according to step (a). As is shown in the examples, the chosen pH and also the used buffering agent influence the extent of EV binding to the anion exchange surface of the solid phase. Therefore, following the teachings of the present invention allows to adjust binding conditions that preferentially bind cfDNA, while EVs and cfRNA predominantly remain in the binding mixture.

The pH

As disclosed herein and discussed in the example section, the pH of the binding buffer influences whether EVs are co-bound together with the cfDNA to the anion exchange surface or predominantly remain unbound in the binding mixture.

In embodiments, an acidic binding buffer is used wherein the pH of the binding buffer is in a range of 2.5 to 6.5 or 3 to 6.5. Exemplary pH ranges include pH 3.5 to 6, 3.7 to 5.5 or 4 to 5.2. In embodiments, the pH of the binding buffer is ≤6, ≤5.7 or ≤5.5 to ensure efficient binding of the cfDNA to the anion exchange groups of the solid phase. In certain embodiments, the pH of the binding buffer is ≤5.

As is shown in the examples, binding of EVs to the anion exchange groups of the solid phase is more sensitive to pH changes compared to binding of cfDNA. Thus, while cfDNA shows a similar binding efficiency over a broader range of acidic pH, EVs bind less effectively at higher pHs. This can be used to establish acidic binding conditions in the binding mixture, under which the cfDNA still binds with good yield to the anion exchange groups of the solid phase, while binding of EVs to the anion exchange groups of the solid phase is already significantly reduced.

In embodiments, the pH of the binding buffer is ≥3.5 or ≥3.8. In further embodiments, the pH of the cfDNA binding buffer is ≥4 or ≥4.2. In embodiments, the pH of the binding buffer is ≥4.5 or ≥4.7. As is shown by the examples, increasing the pH of the binding buffer within the acidic range decreases binding of EVs and other cfRNA species and thus allows to further reduce binding of EVs.

Preferably, the pH of the binding mixture prepared in step (a) by contacting the acidic binding buffer with the biological sample and the solid phase comprising anion exchange groups corresponds to the pH of the acidic binding buffer or deviates by ≤1.5 pH units from the pH of the binding buffer, preferably ≤1, ≤0.75 or ≤0.5 pH units.

In embodiments, the pH of the binding mixture prepared in step (a) is in a range of 2.5 to 6.5, in particular 3 to 6.5, such as 3.5 to 6, 3.7 to 5.5 or 4 to 5.2. In embodiments, the pH of the binding mixture is ≤6, ≤5.7 or ≤5.5. In further embodiments, the pH of the binding mixture pf step (a) for binding cfDNA to the anion exchange groups of the solid phase is ≤5. The pH of the binding mixture may be ≥3.5 or ≥3.8. In embodiments, the pH of the binding mixture is ≥4 or ≥4.2, such as ≥4.5 or ≥4.7. As disclosed herein, increasing the pH of the binding mixture within such narrow acidic range allows to adjust the binding conditions and thereby allows to deplete EVs in the isolated ccfDNA as the EVs bind significantly less efficiently than cfDNA under these conditions as is demonstrated by the examples.

The pH of the binding mixture prepared in step (a) may be lower than the pKa of the ionized form of the anion exchange groups of the solid phase to enable good binding of the cfDNA. The pH of the binding mixture may be at least 1, at least 1.5, at least 2 or at least 2.5 unit(s) lower than the pKa of the anion exchange group.

To maintain a stable pH, the pH of the binding mixture prepared in step (a) is preferably within the buffering range of the acidic binding buffer.

Even though it is preferred for many applications that the pH in the binding mixture is established by contacting the biological sample with the acidic binding buffer, the present invention also covers embodiments, wherein the pH value in the binding mixture is adjusted and thus modified after the biological sample was contacted with the binding buffer. Thus, according to one embodiment, the pH value of the binding mixture is adjusted to ensure that the pH of the binding mixture is within the intended range. Suitable pH values are described above and it is referred to the respective disclosure. E.g. the adjustment can be made manually. The pH value of the binding mixture may be determined and then adjusted to the desired pH value by adding appropriate pH modifying substances such as acids or bases. Such procedure can be advantageous if the biological sample has an unusual high or low pH value. However, preferably, the pH of the binding mixture is exclusively established by the addition of the acidic binding buffer.

As disclosed herein, the binding mixture of step (a) may be prepared by contacting the biological sample with the acidic binding buffer and the solid phase comprising anion exchange groups. In embodiments, the binding conditions in the binding mixture of step (a) are exclusively established by contacting the biological sample with the binding buffer and the solid phase. In embodiments, the acidic binding buffer is contacted in step (a) with the biological sample in a ratio of sample to binding buffer that is selected from a range between 10:1 to 1:10, preferably 5:1 to 1:5, 4:1 to 1:4, 3:1 to 1:3, or 2:1 to 1:2, more preferably 1:1.

The Buffer Agent

As disclosed herein, the acidic binding buffer comprises a buffering agent. The buffering agent is chosen such that it has a buffering capacity that includes the desired binding pH value of the binding mixture to allow efficient binding of the cfDNA to the anion exchange surface of the solid phase. As is demonstrated in the examples, the choice of the used buffering agent can influence EV binding and thus recovery. Advantageously, the selectivity for cfDNA binding and EV depletion during binding can thus be further improved by choice of the buffering agent. This results in that EVs remain in the binding mixture while the cfDNA is efficiently bound to the solid phase.

In one embodiment, the acidic cfDNA binding buffer of step (a) comprises a buffering agent that has at least 1 pKa value. The buffering agent may have one or more of the following characteristics:

(i) the buffering agent has at least 2 pKa values, optionally wherein the different pKa values deviate by at least 0.75;

(ii) the one or more pKa values of the buffering agent are in a range of 1 to 6.5, optionally 1.2 to 5.5 or 1.2 to 5;

(iii) the buffering agent has at least one pKa value in a range of 1 to 4.

The buffering agent may comprise an acid and a base, wherein the acid preferably comprises a carboxylic acid group and the base is the conjugate base of the acid, which preferably is a carboxylic acid. As is demonstrated by the examples, it is advantageous to include a carboxylic acid based buffering agent into the acidic binding buffer. The buffering agent may comprise a carboxylic acid and a salt of said carboxylic acid. Suitable embodiments are well-known in the art. According to one embodiment, the carboxylic acid (i) comprises 1 to 3 carboxylic acid groups;

(ii) is aliphatic; and/or (iii) is saturated.

In embodiments, the buffering agent comprised in the acidic binding buffer that is used in step (a) comprises a buffer component selected from citrate, oxalate, formate, acetate, propionate, lactate and tartrate. As is shown by the examples, cfDNA could be captured efficiently when using such buffers at an appropriate pH, while binding of EVs to the anion exchange groups of the solid phase could be reduced. Following the teachings of the present disclosure, the skilled person can identify further selective cfDNA binding conditions.

In one embodiment, the acidic cfDNA binding buffer of step (a) has a pH of ≥3.5, preferably ≥3.8 or ≥4. For such pH values, the buffering agent may comprise a buffer component selected from citrate, oxalate, formate, propionate, lactate and tartrate. Preferably, the buffer component is selected from oxalate, formate, lactate and tartrate. It may be selected from oxalate and formate. In a further preferred embodiment, the buffer component is citrate.

In a particular embodiment, the acidic cfDNA binding buffer of step (a) has a pH of ≥3.5, preferably ≥3.8 or ≥4 and wherein the buffering agent comprises oxalate as buffer component. As is demonstrated by the examples, oxalate was particularly effective in ensuring binding of cfDNA, while depleting EVs. EVs thus remain in the binding mixture. As noted above, in embodiments, the pH of the acidic ccfDNA binding buffer is ≤6, ≤5.7 or ≤5.5 to ensure efficient binding of the cfDNA to the anion exchange groups of the solid phase. In certain embodiments, the pH of the binding buffer is ≤5.

In a preferred embodiment, the acidic cfDNA binding buffer of step (a) has a pH of ≥3.5, preferably ≥3.8 or ≥4 and the buffering agent comprises citrate as buffer component. As is demonstrated by the examples, citrate was effective in ensuring binding of cfDNA while EVs remain in the binding mixture. As noted above, in embodiments, the pH of the acidic ccfDNA binding buffer is ≤6, ≤5.7 or ≤5.5 to ensure efficient binding of the cfDNA to the anion exchange groups of the solid phase. In certain embodiments, the pH of the binding buffer is ≤5. As is disclosed in the examples, such acidic cfDNA binding buffer works well in combination with anion exchange particles comprising trialkylamine or dialkylaminoalkyl groups (such as DEAPS) for cfDNA binding in step (a).

In one embodiment, the acidic cfDNA binding buffer of step (a) has a pH of ≥4.5, preferably ≥4.8 or ≥5 and wherein the buffering agent comprises acetate as buffer component. As is shown in the examples, a higher pH of the acidic binding buffer is advantageous when using acetate as buffer in order to reduce EV binding to the anion exchange groups of the solid phase during the cfDNA capture step. Compared with other carboxylic acid based buffers, acetate shows at the same pH a higher tendency to promote binding of EVs. Therefore, a higher pH is required in the acidic binding buffer to compensate this effect and ensure selective cfDNA binding with remote EV recovery. In embodiments, the binding buffer does not comprise acetate as main buffer component and optionally is free of acetate.

The acidic cfDNA binding buffer that is added in step (a) to adjust the binding conditions in the binding mixture may comprise the buffering agent in a concentration of 1M or less, 0.7M or less, 0.5M or less or 0.25M or less. The suitable concentration also depends on the volume of the binding buffer that is contacted with the biological sample. As is shown by the examples, in some embodiments, 1 volume of the binding buffer is mixed with 1 volume of the biological sample. The resulting mixture may then be contacted with the solid phase for cfDNA binding. However, as noted before, other contacting orders are also feasible and within the scope of the present invention.

The acidic cfDNA binding buffer used in step (a) comprises the buffering agent in a sufficient concentration so that the desired pH in the binding mixture can be achieved, respectively maintained. In embodiments, the acidic binding buffer comprises the buffering agent is concentration of at least 30 mM, such as at least 50 mM or at least 75 mM, such as at least 80 mM. The acidic binding buffer of step (a) may comprise the buffering agent e.g. in a concentration that lies in a range of 30 mM to 500 mM, such as 50 mM to 300 mM, 75 mM to 250 mM or 80 mM to 200 mM. In embodiments, the buffering agent is comprised in a concentration that lies in a range of 50 mM to 150 mM, such as 75 mM to 125 mM.

As disclosed herein, the binding mixture is prepared by contacting the biological sample with the acidic binding buffer (and the solid phase comprising anion exchange groups, preferably magnetic anion exchange particles). Therefore, the components of the acidic binding buffer which has been described in detail above are also comprised in the binding mixture. It is thus referred to the above disclosure.

According to one embodiment, the binding mixture of step (a) does not comprise acetate as main buffer component. Optionally, no acetate is added in step (a) to the biological sample, at least not in a concentration above 20 mM or above 15 mM.

In embodiments, the binding mixture of step (a) comprises the buffering agent originating from the binding buffer in a concentration of 0.5M or less, 0.35M or less, 0.3M or less or preferably 0.25M or less. The binding mixture may comprise the buffering agent originating from the binding buffer in a concentration of at least 15 mM, such as at least 25 mM or at least 35 mM, such as at least 40 mM. The binding mixture of step (a) may comprise the buffering agent originating from the binding buffer in a concentration that lies in a range of 15 mM to 250 mM, 25 mM to 200 mM, 30 mM to 150 mM or 40 mM to 125 mM. In embodiments, the buffering agent originating from the binding buffer in a concentration that lies in a range of 25 mM to 75 mM, such as 30 mM to 65 mM.

Optional Salt, Such as a Non-Buffering Salt

According to one embodiment, the acidic binding buffer that is added in step (a) comprises a salt. The salt may be a non-buffering salt. However, as is demonstrated in the examples, the addition of salt is not required so that this is an optional component of the binding buffer and hence the binding mixture of step (a).

The salt allows to further reduce binding of EVs and other components that should be excluded from binding at this step to the solid phase. The use of such salt advantageously allows to optimize the binding conditions by adjusting the salt concentration. For example, by increasing the salt concentration the binding of EVs and other components that should be excluded from binding can be weakened. E.g. at a salt concentration between 0.5-1M in the binding mixture elution conditions for the components that shall not bind are established.

In embodiments, the acidic binding buffer that is added in step (a) comprises a buffering salt as buffering agent and in addition thereto a non-buffering salt. The non-buffering salt may have at least one of the following characteristics:

it is a non-chaotropic salt;
it is an monovalent salt;
it is an alkali metal salt, preferably an alkali metal halide; and/or
it is selected from sodium chloride, potassium chloride, lithium chloride and cesium chloride, preferably selected from sodium chloride and potassium chloride. In embodiments, the non-buffering salt is sodium chloride.

In one embodiment, the acidic binding buffer that is added in step (a) comprises a buffering salt as buffering agent and in addition thereto an ammonium salt.

The concentration of the non-buffering salt in the binding buffer is in embodiments, 1M or less, such as 750 mM or less. The concentration of the non-buffering salt in the binding buffer may be 500 mM or less, 370 mM or less, 300 mM or less or 250 mM or less.

In further embodiments, the total salt concentration in the binding buffer is 1M or less or 750 mM or less. The total salt concentration in the acidic cfDNA binding buffer and also the prepared binding mixture of step (a) is chosen such that cfDNA can bind to the anion exchange groups. Therefore, the overall salt concentration in the binding mixture that results from the added reagents should not be so high that elution of the cfDNA is promoted as this would reduce the cfDNA yield. It is preferred that the total salt concentration in the binding buffer is 500 mM or less, 370 mM or less, 300 mM or less or 250 mM or less.

In the binding mixture, the total concentration of salt(s) introduced into the binding mixture due to the addition of the binding buffer and optionally further reagent(s) is also preferably 1M or less, such as 750 mM or less. As noted above, lower total salt concentrations are preferred to prevent loss of cfDNA. In the binding mixture of step (a), the total concentration of salt(s) introduced into the binding mixture due to the addition of the binding buffer and optionally further reagent(s) is in embodiments 500 mM or less, such as 450 mM or less, 400 mM or less or 370 mM or less. In further embodiments, said total salt concentration is 300 mM or less or 250 mM or less.

Further Features of the Binding Mixture of Step (a)

As disclosed herein, the present method is advantageous in that cfDNA is efficiently bound to the anion exchange groups of the slid phase under the conditions established in the acidic binding mixture, while under said conditions, binding of EVs and optionally also further non-vesicular RNA is reduced. After separation of the bound solid phase with the bound cfDNA, the unbound EVs and optionally non-vesicular RNA remains in the binding mixture and can be recovered therefrom. As is shown in the examples, intact extracellular vesicles are still comprised in the remaining binding mixture of step (a) (e.g. the supernatant when using magnetic particles). Advantageously, these extracellular vesicles may be isolated as such from the remaining sample and/or vesicular RNA may be released therefrom and may be purified as cfRNA from the remaining binding mixture that can be collected after separation step (b). This is e.g. described in conjunction with the method according to the second aspect and also the third aspect.

Therefore, in embodiments, the binding mixture of step (a) does not comprise during the cfDNA binding step (a) a detergent or other lytic agent that would cause substantial lysis of the comprised extracellular vesicles. Otherwise, the EVs would be lysed or disrupted and the content, such as the comprised RNA, would be released, followed by binding to the solid phase comprising the anion exchange groups. Hence, substantial lysis of the extracellular vesicles would result in the release of vesicular cfRNA, which could then be co-purified together with the cfDNA. It is preferred to avoid such risk. The binding mixture of step (a) does not comprise during the cfDNA binding step (a) an organic solvent and/or a chaotropic salt in a concentration above 500 mM, above 300, above 250 mM, above 200 mM or preferably above 100 mM. Optionally does not comprise a chaotropic salt at all. Chaotropic salts are well-known in the art and include guanidinium salts, iodides, thiocyanates, perchlorates and other chaotropic salts of equal or stronger chaotropic nature. As disclosed herein, such agents may be added to the remaining binding mixture if desired, however, after the anion exchange solid phase with the bound cfDNA was separated from the remaining sample.

In some embodiments, the binding mixture used in step (a) does not comprise a chemical crowding agent (e.g., polyethylene glycol (PEG)) at a concentration of 0.5% or more.

The Solid Phase Comprising Anion Exchange Groups

The solid phase that is comprised in the binding mixture of step (a) provides an anion exchange surface and thus comprises anion exchange groups at its surface. The solid phase may be provided e.g. by a porous separation means, such as a filter or membrane or may be provided by particles, preferably magnetic particles. The use of particles, in particular magnetic anion exchange particles is preferred.

Various anion exchange groups comprising functional groups carrying at the binding conditions positive charges may be used that provide the capability to bind negatively charged analytes such as cfDNA. Examples of such functional groups are primary, secondary, tertiary or quaternary amino groups. The amino functionality may also be part of a heterocyclic or heteroaromatic ring, such as the imidazole ring in e.g. histidine or histamine. As disclosed herein, such functional groups may be provided at the surface of the solid phase as monomers, oligomers, or polymers, whereby an increasingly higher density of positive charges on the particle surface is provided. As demonstrated by the examples, EVs have a higher tendency to bind to anion exchange surfaces having a higher charge density, as it is e.g. provided by oligomers or polymers. Therefore, for binding EVs (see e.g. subsequent step (a), it may be advantageous to use anion exchange groups providing a high charge density. In contrast, for binding cfDNA while reducing binding of EVs, it is preferred to use monomeric anion exchange groups, which provide one ionizable group per surface attached anion exchange group. However, as is shown by the examples, variations are possible and may be balanced by the choice of the remaining binding conditions, such as the pH and the buffering agent present in the binding mixture of step (a).

The anion exchange groups may be coupled as ligands to the surface of the solid phase, such as particles, membranes or other solid phases, as it is well-known in the art.

The surface of the solid phase may comprise anion exchange groups of a single type, however, different types of anion exchange groups may also be used. Suitable anion exchange groups for binding charged molecules such as cfDNA and EVs are provided by monoamines, diamines, polyamines, and nitrogen-containing aromatic or aliphatic heterocyclic groups. Preferably, the anion exchange group comprises at least one amino group, preferably a primary, secondary or tertiary amino group.

In embodiments, the anion exchange group comprises a group selected from the group consisting of primary, secondary and tertiary amines of the formula $$(R)_3N, (R)_2NH, RNH_2 \text{ and/or } X\text{—}(CH_2)_n\text{—}Y$$

wherein

X is $(R)_2N$, RNH or $NH_2$,

Y is $(R)_2N$, RNH or $NH_2$,

R is independently of each other a optionally substituted linear, branched or cyclic alkyl, alkenyl, alkynyl or aryl substituent which may comprise one or more heteroatoms, preferably selected from O, N, S and P, and n is an integer in the range of from 0 to 20, preferably 0 to 18.

Hence, the anion exchange groups may have an ionisable, in particular protonatable group and optionally may have more than one ionizable group which may be the same or different. A protonatable group preferably is a chemical group which is neutral or uncharged at a high pH value and is protonated at a low pH value, thereby having a positive charge. In particular, the protonatable group is positively charged at the binding pH at which binding of the cfDNA to the solid phase occurs. In embodiments, the pKa value of the (protonated) protonatable group is in the range of 5 to 13, such as 6 to about 12.5 or 7 to about 12. In embodiments, the pKa value is in the range from 8 to 12 or 9 to 11.5.

Examples of suitable anion exchange groups comprise in particular amino groups such as primary, secondary and tertiary amino groups as well as cyclic amines, aromatic amines and heterocyclic amines. Preferred are tertiary amino groups. The amino groups may bear alkyl, alkenyl, alkynyl and/or aromatic substituents, including cyclic substituents and substituents which together with the nitrogen atom form a heterocyclic or heteroaromatic ring. The substituents may comprise 1 to 20 carbon atoms, such as 1 to 12, 1 to 8, 1 to 6, 1 to 5, 1 to 4, 1 to 3 or 1 or 2 carbon atoms. They may be linear or branched and may comprise heteroatoms such as oxygen, nitrogen, sulfur, silicon and halogen (e.g. fluorine, chlorine, bromine) atoms. In embodiments, the substituents comprise not more than 4, more preferably not more than 3, not more than 2 or not more than 1 heteroatom.

Examples of amine functions are primary amines such as aminomethyl (AM), aminoethyl (AE), aminoalkyl, alkylaminoalkyl, dialkylaminoalkyl such as diethylaminoethyl (DEAE), ethylendiamine, diethylentriamine, triethylentetraamine, tetraethylenpentaamine, pentaethylenhexaamine, trimethylamino (TMA), triethylaminoethyl (TEAE), linear or branched polyethylenimine (PEI), carboxylated or hydroxyalkylated polyethylenimine, jeffamine, spermine, spermidine, 3-(propylamino)propylamine, polyamidoamine (PAMAM) dendrimers, polyallylamine, polyvinylamine, N-morpholinoethyl, polylysine, and tetraazacycloalkanes.

In one embodiment the anion exchange group that is provided as ligand on the surface of the solid phase comprises 1 to 20, 1 to 15 or 1 to 10 ionizable groups, such as the preferred amino groups, per anion exchange group. In preferred embodiments, the anion exchange group of the solid phase that is used for cfDNA binding comprises 1 to 8, 1 to 6, 1 to 5, 1 to 4, 1 to 3 or 1 to 2 ionizable groups, such as the preferred amino groups, per anion exchange group. As is demonstrated in the examples, the use of anion exchange groups that comprise few ionisable groups (e.g. 1 to 5, preferably 1 or 2), such as the preferred amino groups, per anion exchange group is preferred for cfDNA binding step (a). While binding of cfDNA to such anion exchange surface is efficient, binding of EVs is reduced.

Preferably, the particles used for cfDNA binding in step (a) comprise anion exchange groups with a dialkylaminoalkyl group for cfDNA binding, such as a diethylaminoalkyl group, wherein the particles may also comprise more than one type of dialkylaminoalkyl groups.

Suitable anion exchange groups are also disclosed in the items of the invention as identified below, see in particular items 48 to 77.

As disclosed therein, the anion exchange groups may comprise at least one amino group that is part of a heterocyclic or heteroaromatic ring. The amino group may be part of an imidazole ring. The anion exchange groups may comprise e.g. histidine and/or histamine. According to one embodiment, the solid phase comprises histamine coupled to a carboxy-modified surface. Alternatively, an imidazole carboxylic acid, such as 4-imidazole acetic acid may be coupled to a surface, such as an amino-modified surface.

According to one embodiment, the anion exchange groups comprise histidine or histamine. The number of histidine groups is preferably at least 3 or at least 4. According to one embodiment, the anion exchange groups are selected from (i) oligo-histidine, wherein the number of histidine monomers is in the range of 4 to 18, such as 5 to 16, 6 to 14, 7 to 13 or preferably 8 to 12, and (ii) a histamine group, optionally wherein the anion exchange groups comprise 1 histamine group per anion exchange group.

According to one embodiment, the anion exchange groups are selected from (i) polyhistidine and (ii) anion exchange groups comprising Bis-Tris groups. According to one embodiment the number of histidine monomers in the polyhistidine is at least 30.

In embodiments, anion exchange particles are used as solid phase for cfDNA binding in step (a). Magnetic particles are preferred. Anion exchange particles that can be used in the context of the present invention include, but are not limited to, particulate materials that are functionalized with anion exchange groups. As basic material for the particles, any material suitable for anion exchange chromatography may be used, including but not limited to silicon containing materials such as silica and polysilicic acid materials, borosilicates, silicates, anorganic glasses, organic polymers such as poly(meth)acrylates, polyurethanes, polystyrene, agarose, polysaccharides such as cellulose, metal oxides such as aluminum oxide, magnesium oxide, titanium oxide and zirconium oxide, metals such as gold or platinum, sephadex, sepharose, polyacrylamide, divinylbenzene polymers, styrene divinylbenzene polymers, dextrans, and derivatives thereof; glass or silica. In embodiments, the particles are made of or contain a mineral or polymeric material such as silica, glass, quartz, polyethylene, polypropylene, polyvinylidene fluoride, polyacrylonitrile, polyvinylchloride, polyacrylate, methacrylate or methyl methacrylate. Important is that the particles comprise anion exchange groups at their surface and hence provide an anion exchange surface for interaction with the cfDNA. Such surface can be provided by functionalizing the base material of the particles with suitable anion exchange groups. For functionalizing particles with anion exchange groups in order to provide an anion exchange surface, several methods are feasible and known to the skilled person. The anion exchange groups may be bound directly to the surface of the particles, either covalently or non-covalently, electrostatically and/or may form part of a polymer or other composition which forms a surface coating or which is provided at the surface of the particles. The anion exchange groups may also be precipitated on the particles. According to one embodiment, the anion exchange groups are applied in form of a coating on the particles. A covalent attachment of the anion exchange groups is preferred. The particles may comprise at their surface functionalities for attachment of the anion exchange groups, for example functionalities such as Si—O—Si, Si—OH, (poly-)silicic acid, alcohol, diol or polyol, carboxylate, amine, phosphate or phosphonate. The anion exchange groups may be attached to the solid phase, for example, by using epoxides, (activated) carboxylic acids, silanes, acid anhydrides, acid chlorides, formyl groups, tresyl groups or pentafluorophenyl groups. The functional groups may be attached directly to the solid phase or via (linear or branched) spacer groups, e.g. hydrocarbons such as —$(CH_2)_n$— groups, carbohydrates, polyethylenglycols and polypropylenglycols. In embodiments, the solid phase comprises carboxyl groups for attaching anion exchange groups by covalent attachment using carbodiimide-based reactions, in particular by reacting carboxyl groups of the particles with amino groups comprised in the anion exchange groups. Alternatively, also a polymer composed of monomers comprising the anion exchange group such as an amino functional group can be used as anion exchange material. In certain embodiments, the particles have a silicon containing surface such as a polysilicic acid surface and the anion exchange groups are coupled to said surface by using suitable organosilanes such as an aminosilane.

The anion exchange group may comprise a protonatable group attached to a linker structure. The linker may be a linear, branched or cyclic alkylen, alkenylen or alkynylen group which may comprise 1 to 20 carbon atoms, such as 1 to 12, 1 to 8, 1 to 6, 1 to 5, 1 to 4, 1 to 3 or 1 or 2 carbon atoms. It may further comprise heteroatoms such as oxygen, nitrogen, sulfur, silicon and halogen (e.g. fluorine, chlorine, bromine) atoms, preferably not more than 4, more preferably not more than 3, not more than 2 or not more than 1 heteroatom. In embodiments, the linker group is an alkylene group, in particular a propylene group.

According to one embodiment, the particles comprise a silicon containing surface, preferably a polysilicic acid surface which is derivatized with a silane compound comprising at least one anion exchange group, such as the preferred dialkylaminoalkyl group. Suitable methods involving the use of organosilanes such as aminosilanes are well-known. In embodiments, magnetic anion exchange particles are used in step (a) for cfDNA binding, which comprise DEAPS groups as anion exchange groups. As is demonstrated by the examples, such anion exchange groups are particularly suitable, in particular when being used in combination with the acidic binding buffers according to the present disclosure.

in embodiments the anion exchange groups of the solid phase used in step (a) comprise at least one ionizable group, wherein said group is ionizable by protonation, wherein the ionizable group is protonated at the acidic pH of the binding mixture and is neutral or uncharged at a basic pH, such as at a basic pH of at least 8, at least 9 or at least 10. The solid phase used in step (a) may comprise anion exchange groups that have a single positive charge per anion exchange group at the pH of the binding mixture, optionally at a pH ranging from ≥3 to ≤6 or ≥3.5≤5.5.

As disclosed herein, the anion exchange groups of the solid phase and the binding conditions used in step (a) may be adjusted to establish binding of the extracellular DNA to the anion exchange groups of the solid phase, while binding of extracellular vesicles to the anion exchange groups of the solid phase is reduced under these binding conditions. In embodiments, magnetic anion exchange particles are used, wherein the anion exchange groups of the magnetic particles comprise a trialkylamine group for cfDNA binding and wherein the acidic binding buffer of step (a) has a pH of ≥3.5, preferably ≥3.8 or ≥4 and wherein the buffering agent comprises a buffer component selected from citrate, oxalate, formate, propionate, lactate and tartrate, preferably selected from oxalate, formate, lactate and tartrate. The binding buffer may comprise the buffering agent in a concentration that lies in a range of 30 mM to 500 mM, 50 mM to 300 mM or 75 mM to 250 mM and optionally comprises a non-buffering salt. As disclosed elsewhere, the total salt concentration in the binding mixture is preferably 750 mM or less, such as 500 mM or less, 370 mM or less, 300 mM or less or 250 mM or less to ensure tight cfDNA binding.

The particles are preferably spherical. The particles may have a mean diameter selected from the ranges of 100 nm to 35 μm, such as 150 nm to 30 μm, 200 nm to 25 μm, 250 nm to 20 μm, 300 nm to 15 μm or 350 nm to 10 μm. Examples include 400 nm to 7.5 μm, 450 nm to 5 μm, 500 nm to 3 μm and 550 nm to 2.5 μm. Suitable exemplary ranges include but are not limited to 100 nm to 10 μm, 150 nm to 7.5 μm, 200 nm to 5 μm, 300 nm to 4 μm, 500 nm to 3.5 μm, 550 nm to 2 μm and 600 nm to 1.5 μm. Particles of the respective sizes and in particular of a smaller size such as 10 μm or less, 7.5 μm or less, preferably 5 μm or less, 2.5 μm or less or 1.5 μm or less are easy to handle and can be well resuspended in the binding mixture. Furthermore, respective small particles provide a large surface area that can bind and accordingly can efficiently collect the cfDNA from the binding mixture of step (a).

When using particles such as magnetic particles for performing the binding step, the anion exchange particles are not comprised in a column or other device that would prevent the particles from moving in the binding mixture. Instead the particles can move in the binding mixture that is comprised in a container, e.g. when the binding mixture is agitated. Therefore, the particles must be collected from the binding mixture to recover the bound cfDNA. According to a preferred embodiment, the particles are magnetic. This simplifies the processing of the particles because they can be processed by the aid of a magnet which is advantageous for automation. The particles may have ferrimagnetic, ferromagnetic, paramagnetic or superparamagnetic properties and in embodiments are superparamagnetic. Such properties can be achieved by incorporating a suitable magnetic material into the particles. Suitable methods are known to the skilled person. Preferably, the magnetic material is completely encapsulated e.g. by the silica, polysilicic acid, glass or polymeric material that is used as base material for the particles. In certain preferred embodiments, the nucleic acid binding matrix is a silicon containing particle, preferably a polysilicic acid particle, preferably a magnetic polysilicic acid particle which carries anion exchange groups.

Examples of suitable particles and anion exchange groups are described in WO 2010/072834 A1, DE10 2008 063 001A1, WO2010072821A1, DE 10 2008 063 003, WO 99/29703 and WO0248164 to which it is referred.

The anion exchange particles are added in an amount so that the binding capacity of the anion exchange surface is preferably in excess of the cfDNA contained in the biological sample. This supports a high yield of recovered cfDNA. Non-limiting examples of suitable amounts of particles (in mg) per ml sample include 0.15 mg to 10 mg, 0.25 mg to 5 mg, 0.5 mg to 3.5 mg, 0.75 mg to 3 mg, 1 mg to 2.5 mg and 1.25 mg to 2 mg. The suitable amount inter alia depends on the sample volume to be processed and the anion exchange particles used and can be determined by the skilled person.

At the end of step (a), extracellular DNA contained in the binding mixture are bound to the solid phase comprising anion exchange groups, such as magnetic particles comprising anion exchange groups.

Step (b)

Step (b) of the method according to the first aspect comprises separating the solid phase with the bound extracellular DNA from the remaining binding mixture, wherein the remaining binding mixture comprises extracellular vesicles. As disclosed herein, step (b) of the methods according to the second and third aspects comprise essentially the same step (b). Therefore, the present disclosure also applies with respect to step (b) of these methods.

In step (b) the solid phase with the bound extracellular DNA is separated from the remaining binding mixture. Thereby, the solid phase with the bound extracellular DNA is collected. For this purpose, any means known in the art can be used. Suitable means include but are not limited to magnetic separation if magnetic particles are used, centrifugation e.g. if non-magnetic particles are used, sedimentation, the application of a vacuum, filtration and the like.

The remaining binding mixture may be collected as sample comprising extracellular vesicles and non-vesicular RNA and said sample may be further processed in a step (c) in order to recover in a subsequent step (c) EVs and/or cfRNA from said sample from which cfDNA was depleted. Details are described below in conjunction with the method according to the second and third aspect of the present disclosure.

After separating the solid phase with the bound extracellular DNA in step (b) the method may furthermore comprise comprises washing the extracellular DNA. Suitable wash solutions are known in the art.

After separation and preferably washing, the extracellular DNA may be recovered, preferably eluted from the solid phase. Suitable elution protocols are known in art and also disclosed in the patent literature on anion exchange matrices referred to above. In a preferred embodiment, the method comprises eluting the extracellular DNA from the solid phase by contacting the solid phase with the bound extracellular DNA with a basic elution solution, optionally wherein the pH of the elution solution is in the range of 8 to 13, such as 9 to 13, 10 to 13 or 11 to 12. As is known in the art, such elution conditions promote the release and thus elution of the bound cfDNA.

Elution may also be assisted by incorporating a salt. According to one embodiment, elution is achieved by high salt conditions, e.g. using an elution solution with a concentration of salt, e.g. >1M salt. In such an embodiment, the elution can be achieved independent of the pH. However, this is less preferred, as this would require a clean-up of the eluate (to remove the salt), at least for some downstream applications.

The recovered cfDNA may then be analysed using conventional analytic methods.

Step (c)

The method according to the first aspect may further comprise processing the remaining binding mixture from which the solid phase with the bound cfDNA was separated. The remaining binding mixture may be collected and further processed as sample comprising extracellular vesicles (and optionally) non-vesicular RNA. Further processing may encompass enriching one or more biological targets of interest from the remaining binding mixture. E.g. such analytes may be recovered using the same binding conditions but different anion exchange particles comprising different anion exchange groups, which allow binding of e.g. EVs and/or cfRNA under the binding conditions. In addition, the same anion exchange particles may be used applying different buffer conditions which promote binding of the analytes such as EVs. E.g. the pH can be lowered or a buffering agent may be added that promotes binding of EVs such as acetate. It is also within the scope of the invention to use different anion exchange particles and different binding conditions to capture the target analytes of interest from the remaining binding mixture from which cfDNA was removed.

In particular embodiments, the method according to the first aspect comprises
   (c) enriching as biological targets extracellular vesicles and/or extracellular RNA from the remaining binding mixture.

Suitable embodiments for performing step (c) are disclosed in the conjunction with the methods according to the second and third aspect below. It is referred to step (c) and subsequent steps as disclosed in conjunction with these aspects. The enrichment and purification of cfRNA that comprises vesicular RNA is of particular interest.

The Method According to the Second and Third Aspect

According to a second aspect, a method for sequentially enriching (i) extracellular DNA and (ii) extracellular vesicles and/or extracellular RNA from a biological sample comprising extracellular DNA and extracellular vesicles is provided, wherein the method comprises:

(a) preparing a binding mixture comprising
the biological sample,
a solid phase comprising anion exchange groups,
an acidic binding buffer comprising a buffering agent,
and binding extracellular DNA to the solid phase;

(b) separating the solid phase with the bound extracellular DNA from the binding mixture, wherein the remaining binding mixture comprises extracellular vesicles; and (c) enriching extracellular vesicles and/or extracellular RNA from the remaining binding mixture.

As disclosed above and in the examples, it is advantageous that the present invention enables the sequential isolation of cfDNA, followed by isolation of cfRNA or EVs. Therefore, for instance, after selective isolation of extracellular DNA (such as ccfDNA), the remaining mixture (e.g. supernatant) of the separation step can be used for isolation of other analytes, in particular EVs. In this way, the invention also allows sequential isolation of extracellular DNA (e.g. ccfDNA) and EVs (or EV content), or extracellular DNA (in particular ccfDNA) and total ccfRNA into separate eluates. This is a significant improvement compared to prior art methods.

According to a third aspect, a method for enriching extracellular vesicles and/or extracellular RNA from a biological sample comprising extracellular vesicles and non-target biomolecules is provided, the method comprising:

(a) preparing a binding mixture comprising
the biological sample,
a solid phase comprising anion exchange groups,
an acidic binding buffer comprising a buffering agent,
and binding at least extracellular DNA as non-target biomolecule to the solid phase;

(b) separating the solid phase with the bound extracellular DNA from the binding mixture, wherein the remaining binding mixture comprises extracellular vesicles; and (c) enriching extracellular vesicles and/or extracellular RNA from the remaining binding mixture.

The method according to the third aspect allows to enrich EVs and/or extracellular RNA from a biological sample comprising extracellular vesicles, by first depleting non-target biomolecules such as extracellular DNA in step (a). This allows to provide EVs and/or cfRNA with less cfDNA contamination.

Step (a) and Step (b)

Steps (a) and (b) essentially corresponds to steps (a) and (b) of the method according to the first aspect. Therefore, it is referred to the corresponding disclosure, which also applies with respect to the method according to the second aspect and the method according to the third aspect.

Step (c)

Step (c) comprises enriching extracellular vesicles and/or extracellular RNA from the remaining binding mixture. As disclosed herein, enriching also refers to and encompasses isolating and purifying.

Extracellular EVs may be enriched as separate fraction using suitable EV isolation methods. Suitable methods are known in the art and also disclosed herein.

Furthermore, extracellular RNA may be enriched and thus isolated from the remaining binding mixture. As is demonstrated by the examples, the present invention allows to isolate total cfRNA from the remaining binding mixture from which the cfDNA was separated. It is also within the scope of the present disclosure to isolate EVs and in parallel non-vesicular RNA, as is also supported by the examples. Therefore, step (c) comprises enriching extracellular vesicles and/or extracellular RNA from the remaining binding mixture.

In preferred embodiments, step (c) comprises enriching extracellular vesicles (EV) and optionally non-vesicular RNA from the remaining binding mixture collected after separation step (b). As is known in the art, extracellular vesicles may be enriched by at least one of the following binding to a solid phase, ultracentrifugation, ultrafiltration, gradients, affinity capture, in particular biochemical affinity capture, antibody capture, size exclusion chromatography or a combination of the foregoing. All these methods may be used in conjunction with the present invention. Numerous protocols and commercial products are available for extracellular vesicle/exosome isolation, and are known to the skilled person. E.g. EVs and EV content can be isolated using existing methods, such as exoEasy/exoRNeasy, miR-CURY Exosome Isolation kits (or equivalent), ultracentrifugation, size exclusion chromatography, immunocapture, or other methods known in the art. Exemplary, non-limiting isolation methods are described in the following.

Extracellular vesicles and in particular exosomes can be enriched e.g. by methods involving ultracentrifugation. An exemplary ultracentrifugation isolation method is described by Thery et al. (Isolation and Characterization of Exosomes from Cell Culture Supernatants and Biological Fluids. Unit 3.22, Subcellular Fractionation and Isolation of Organelles, in Current Protocols in Cell Biology, John Wiley and Sons Inc., 2006). Hence according to one embodiment, extracellular vesicles are enriched by ultracentrifugation. To increase the purity of the enriched extracellular vesicles, cells and cell fragments, and optionally apoptotic bodies if desired, can be removed prior to enriching the extracellular vesicles, e.g. by centrifugation or filtration. E.g. filtration methods can be used which exclude particles $\geq 0.8$ µm, $\geq 0.7$ µm or $\geq 0.6$ µm. According to embodiments, filtration membranes are used which have a pore size in the range of 0.1 µm to 0.5 µm. According to one embodiment, extracellular vesicles are enriched by affinity capture to a solid phase. According to one embodiment, extracellular vesicles, such as exosomes, are enriched by immuno-magnetic capture using magnetic beads coated with antibodies directed against proteins exposed on extracellular vesicles, e.g. on exosomal membranes.

According to one embodiment, extracellular vesicles are captured by passing the cell-depleted sample through a vesicle capture material. Bound extracellular vesicles can be washed and subsequently eluted. Commercial systems that are based on biochemical affinity capture such as the exoEasy Kit (QIAGEN) are available for extracellular vesicle purification and can be used in conjunction with the present invention. Methods based on the use of volume-excluding polymers, such as PEG, have also been described for the isolation of EVs. Therein, the polymers work by tying up water molecules and forcing less-soluble components such as extracellular vesicles out of solution, allowing them to be collected by a short, low-speed centrifugation. Commercial products that make use of this principle are ExoQuick (System Biosciences, Mountain View, USA) and Total Exosome Isolation Reagent (Life Technologies, Carlsbad, USA). Hence according to one embodiment, extracellular vesicles are enriched by precipitation with a volume-excluding polymer. Also, extracellular vesicles, such as exosomes, can be enriched based on their density, e.g. by layering the sample onto discontinuous sucrose or iodixanol gradients and subjecting to high speed centrifugation. Thus according to one embodiment, extracellular vesicles, such as exosomes, are enriched by density gradient centrifugation.

According to one embodiment, the enriched extracellular vesicles comprise or predominantly consist of exosomes and/or microvesicles. According to one embodiment, the extracellular vesicles comprise or predominantly consist of exosomes. Thus, in embodiments, the enriched biological target essentially consists of exosomes.

In a preferred embodiment, step (c) comprises enriching extracellular vesicles by binding to an anion exchange surface of a solid phase. The solid phase may be provided by a porous separation means, such as preferably a filter or membrane. Preferably, the solid phase is provided by anion exchange particles, preferably magnetic particles.

In embodiments, step (c) comprises enriching extracellular vesicles by binding to magnetic anion exchange particles, wherein enriching comprises:

(aa) contacting the remaining binding mixture collected after step (b) with magnetic anion exchange particles under EV binding conditions so that extracellular vesicles and optionally non-vesicular RNA bind to the anion exchange particles;

(bb) separating the anion exchange particles with the bound extracellular vesicles; and (cc) optionally further processing the anion exchange particles.

It is preferred that the binding conditions used in step (a) for binding cfDNA differ from the binding conditions used in step (c) for binding EVs and optionally extracellular RNA. This is to ensure efficient EV capture by binding to the anion exchange solid phase, which is preferably provided by magnetic anion exchange particles. The different binding conditions in step (a) and step (c) may be achieved by one or more of the following:

In step (c) a solid phase comprising anion exchange groups is used that differs from the solid phase comprising anion exchange groups that is used in step (a). The charge density of the solid phase used in step (c) for binding extracellular vesicles may be higher than the charge density of the solid phase that was used in step (a) for cfDNA binding.

The EV binding mixture of step (c) (aa) may have a lower pH than the cfDNA binding mixture of step (a). As is demonstrated in the examples, EVs bind better at lower acidic pH, while binding of cfDNA can be achieved over a broader range with good yield.

In step (c) a buffering agent may be introduced into the EV binding mixture that differs from the buffering agent that was used in the cfDNA binding mixture of step (a), optionally wherein the buffering agent promotes binding of EVs to the anion exchange groups of the solid phase. Preferably said buffering agent is acetate. As is shown in the examples, acetate promotes binding of EVs.

In one embodiment, the EV binding conditions of step (c) (aa) utilize an acidic pH wherein the EV binding pH is in the range of 2.5 to 5, such as 3 to 5, preferably 3 to 4.5, more preferably 3 to 4. Preparing the EV binding conditions in step (c) (aa) may comprise adding an acidic reagent, optionally wherein the pH of the acidic reagent is in the range of 2.5 to 5.5, such as 2.5 to 5, such as 3 to 5, or 3 to 4.5. In embodiments, the pH is 3-4.

The acidic reagent for adjusting the EV binding conditions may comprise a buffering agent, preferably a carboxylic acid based buffer. Exemplary carboxylic acid based buffers were described above in conjunction with the cfDNA acidic binding buffer. It is referred to the above disclosure. Preferably acetate is used as buffering agent to promote binding of EVs to the anion exchange groups.

In embodiments, the EV binding mixture in step (c) (aa) comprises the buffering agent from the acidic reagent in a concentration of 100 mM to 1M, such as 200 mM to 700 mM, 300 mM to 600 mM or 350 mM to 550 mM, optionally wherein the buffering agent is acetate. The acidic reagent used in step (c) (aa) for establishing EV binding conditions may have a lower pH than the acidic binding buffer of step (a) for cfDNA binding.

According to a preferred embodiment, step (c) uses magnetic anion exchange particles which comprise anion exchange groups as defined in any one of items 49 to 68, preferably as defined in any one of items 58 to 64, of the invention as described below. In embodiments, magnetic particles comprising anion exchange groups selected from histamine, polyethyleneimine and poly-histidine are used in step (c) for EV binding under acidic conditions. As disclosed herein, also other derivatives containing the imidazole ring may be used as anion exchange groups.

Accordingly, the anion exchange groups of the magnetic anion exchange particles used in step (c) may comprise at least one amino group that is part of a heterocyclic or heteroaromatic ring. The amino group may be part of an imidazole ring. The anion exchange groups may comprise e.g. histidine and/or histamine. According to one embodiment, the solid phase comprises histamine coupled to a carboxy-modified surface. Alternatively, an imidazole carboxylic acid, such as 4-imidazole acetic acid may be coupled to a surface, such as an amino-modified surface.

According to a particular embodiment, the anion exchange groups of the magnetic anion exchange particles used in step (c) comprise histidine or histamine. The number of histidine groups is preferably at least 3 or at least 4.

According to one embodiment, the anion exchange groups of the magnetic anion exchange particles used in step (c) are selected from (i) oligo-histidine, wherein the number of histidine monomers is in the range of 4 to 18, such as 5 to 16, 6 to 14, 7 to 13 or preferably 8 to 12, and (ii) a histamine group, optionally wherein the anion exchange groups comprise 1 histamine group per anion exchange group. As disclosed herein, these anion exchange particles are well suitable for binding extracellular vesicles and/or extracellular RNA in step (c). These anion exchange particles can be used in step (c) for binding of EVs and/or extracellular RNA, while different anion exchange particles are used for cfDNA binding in step (a), such as anion exchange groups comprising a trialkylamine group or dialkylaminoalkyl group for cfDNA binding.

According to a particular embodiment, the anion exchange groups of the magnetic anion exchange particles used in step (c) are selected from (i) polyethyleneimine; (ii) polyhistidine, (iii) oligo-histidine, (iv) histamine and (v) anion exchange groups comprising Bis-Tris groups. According to one embodiment the number of histidine monomers in the polyhistidine is at least 30. These anion exchange particles can be used in step (c) for binding of EVs and/or extracellular RNA, while different anion exchange particles are used for cfDNA binding in step (a), such as anion exchange groups comprising a trialkylamine group or dialkylaminoalkyl group for cfDNA binding.

These magnetic anion exchange particles that can be used for binding extracellular vesicles in step (c) may also be comprised in the kit according to the present disclosure.

After separation step (c) (bb), the solid phase with the bound extracellular vesicles may be contacted with an acidic wash buffer that comprises a buffering agent, preferably acetate. Optionally, the acidic wash buffer does not comprise a detergent, in particular in concentrations high enough to facilitate lysis of vesicles.

According to one embodiment, EVs bound to the anion exchange solid phase are recovered by elution and/or lysis, wherein recovering comprises:

(i) providing a salt having a concentration of more than 1M;

(ii) increasing the pH such that the anion exchange groups are not positively charged, such as at least pH 8;

(iii) contacting the solid phase with the bound EVs with a reagent comprising phenol and a chaotropic salt.

According to a further embodiment, EVs bound to the anion exchange solid phase are recovered by elution and/or lysis, wherein recovering comprises:

(i) providing a salt having a concentration of more than 1M:

(ii) increasing the pH such that the anion exchange groups are not positively charged, such as at least pH 8;

(iii) contacting the solid phase with the bound EVs with a reagent comprising a chaotropic salt and optionally a detergent.

The method may further comprise lysing enriched extracellular vesicles thereby providing a lysate that comprises vesicular RNA. The method may further comprise enriching such as purifying RNA from the lysate. In particular embodiments, step (c) comprises enriching total extracellular RNA from the remaining binding mixture, wherein the enriched total extracellular RNA comprises vesicular RNA and optionally non-vesicular RNA. Suitable RNA isolation methods are described in the examples and are also well-known in the art and moreover commercially available, e.g. RNeasy® or miRNeasy (QIAGEN).

Step (c) may comprise enriching extracellular vesicles and optionally non-vesicular RNA from the remaining binding mixture collected after step (b) and lysing the enriched extracellular vesicles to release the vesicular RNA. After lysis, the released RNA may be purified from the provided lysate, wherein the purified RNA comprises vesicular RNA and optionally non-vesicular RNA if present in the lysate. Relevant molecular information may be obtained by analyzing RNA molecules present in extracellular vesicles such as exosomes. EVs have been shown to contain various small RNA species, including miRNA, piRNA, tRNA (and fragments thereof), vault RNA, Y RNA, fragments of rRNA, as well as long non-coding RNA, and also mRNA.

Exemplary and preferred methods for RNA isolation are described herein and are also known in the art.

According to one embodiment, RNA isolation comprises binding RNA to a solid phase with anion exchange moieties and eluting the RNA from the solid phase. The RNA is bound to the solid phase at binding conditions that allow binding of the RNA to the anion exchange moieties. To that end, suitable pH and/or salt conditions can be used, as is known to the skilled person. The bound RNA can optionally be washed. Any suitable elution method can be used and suitable embodiments are known to the skilled person. Elution can e.g. involve changing the pH value. Thus, elution can e.g. occur at an elution pH which is higher than the binding pH. Likewise, ionic strength can be used to assist or effect the elution. Elution can also be assisted by heating and/or shaking.

Suitable RNA isolation methods are also disclosed in the European application 19216752.6 with the title "Method for enriching vesicular RNA" which was filed on Dec. 16, 2019 in the name of the same applicant and the corresponding PCT application filed today and claiming priority to this European application 19216752.6. The disclosure is with respect to the method for enriching extracellular RNA such as vesicular RNA herewith incorporated by reference. The method for enriching vesicular RNA described therein may be advantageously used for isolating vesicular RNA from the enriched extracellular vesicles.

Further Embodiments of the Disclosed Methods According to the First, Second or Third Aspect According to one embodiment, the methods according to the present disclosure may comprise adding a protease, optionally proteinase K, in one or more of the following step:

prior to step (a);

in step (a);

after step (b);

in step c); and/or after step c), in particular, after step b) and/or after step c).

The methods of the present disclosure may have one or more of the following characteristics:

(i) wherein magnetic anion exchange particles are used in step (a) for binding extracellular DNA, and wherein at least steps (a) and (b) are performed in an automated manner using a robotic instrument, optionally wherein magnetic anion exchange particles are used in step (c) for binding extracellular vesicles, and wherein steps (a) to (c) are performed in an automated manner using a robotic instrument;

(ii) wherein enriched cfDNA and enriched cfRNA are provided in separate fractions, preferably in separate eluate fractions; and/or (iii) wherein enriching encompasses isolating or purifying the target molecule of interest.

As disclosed herein, it is preferred that after step (a) at least 50% of the EVs and/or cfRNA remain in the binding mixture after separating the solid phase with the bound extracellular DNA from the binding mixture, optionally wherein the percentage is at least 60% or at least 65%. As disclosed in the examples, binding of EVs can be efficiently reduced following the teachings of the present invention.

In embodiments, the method comprises removing prior to step (a) cells from a body fluid sample, whereby a cell-depleted or cell-free body fluid sample is provided as biological sample comprising extracellular vesicles that is then contacted with the binding buffer and the solid phase in step (b) to prepare the binding mixture. Methods for separating a cell-containing bodily fluid into a, i.e. at least one, cell-containing fraction and a, i.e. at least one, cell-depleted fraction are well-known in the art and therefore, do not need to be described in detail. Common methods include, but are not limited to, centrifugation, filtration and density gradient centrifugation. The different methods may also be combined. Such common methods may be advantageously used in conjunction with the stabilization technology according to the present disclosure, which advantageously allows to avoid the use of cross-linking agents for stabilization, so that common, established methods may be used. The methods are performed so that the integrity of the comprised cells is preserved. This is advantageous because cell breakage during separation would contaminate e.g. the extracellular nucleic acids that are comprised in the cell-depleted fraction with cellular nucleic acids that are released from disrupted cells.

Biological Sample

The biological sample comprising extracellular vesicles preferably is or is derived from a body fluid. The biological sample may be a sample that was obtained from a body fluid by removing cells. In particular, the biological sample comprising extracellular vesicles may be a cell-free or cell-depleted body fluid sample. The cell-free or cell-depleted body fluid sample preferably is or is derived from the following samples by removing cells: whole blood, plasma, serum, lymphatic fluid, urine, liquor, cerebrospinal fluid, synovial fluid, interstitial fluid, ascites, milk, bronchial lavage, saliva, amniotic fluid, semen/seminal fluid, body secretions, nasal secretions, vaginal secretions, wound secretions and excretions. In a further embodiment the biological sample is a plant extract comprising extracellular vesicles.

In embodiments, the biological sample comprising extracellular vesicles is selected from plasma, serum and urine, wherein urine is preferably cell-depleted or cell-free urine.

In one embodiment, the biological sample comprising extracellular vesicles is or is derived from a cell culture liquid, in particular a cell culture supernatant. The biological sample may be a sample that was obtained from a cell culture liquid by removing the cells. Methods to remove cells have been described herein and are known in the art.

Analysis

The isolated analytes (in particular extracellular DNA and/or extracellular vesicles) can be analyzed and/or further processed using suitable assay and/or analytical methods. Hence, according to one embodiment, the isolated extracellular nucleic acids are analyzed. The analysis can be performed in order to identify, detect, screen for, monitor or exclude a disease, an infection and/or at least one fetal characteristic.

The isolated extracellular DNA and/or EVs, preferably EV content (extracellular RNA) and/or a specific target extracellular nucleic acid comprised or suspected of being comprised in the isolate can be identified, quantified, modified, contacted with at least one enzyme, amplified, reverse transcribed, cloned, sequenced, contacted with a probe and/or be detected. Respective methods are well-known in the prior art and are commonly applied in the medical, diagnostic and/or prognostic field.

According to one embodiment, the (i) isolated extracellular DNA and (ii) isolated vesicular and/or non-vesicular extracellular RNA are analyzed differently, e.g. are tested for different types of variants. For example, the isolated extracellular DNA may be analyzed for one or more variants selected from single nucleotide variants (SNVs), insertions and deletions (InDels) and copy number variants (CNVs). The isolated RNA may be analyzed for fusions, exon skipping events and/or gene expression levels.

According to one embodiment, the isolated extracellular vesicles can be further analyzed. In particular, extracellular vesicles have also been shown to contain genomic DNA fragments from their cells of origin. The methods described in the present disclosure can be used to separate such vesicular DNA from non-vesicular cell-free DNA, thereby allowing separate characterization of both.

Automation

The method according to the present invention can be performed manually, or by using automated systems. Manual methods can often process larger sample volumes. Automated systems usually have due to their design a certain limit with respect to the volume they can process. Automated systems have in particular the advantage that many samples can be processed at the same time and that automated systems are less error prone, because handling errors are avoided. This is a particular advantage where a high number of samples are to be processed, as is the case in many laboratories were samples are analyzed for medical and/or diagnostic purposes. The present method is particularly suitable for automation. Thus, according to one embodiment, the method is performed using an automated system. In this embodiment, it is preferred to use a solid phase selected from magnetic particles, as this simplifies the processing. The magnetic particles including the bound analytes can be processed easily by the aid of a magnetic field, e.g. by using a permanent magnet. This embodiment is e.g. compatible with established robotic systems capable of processing magnetic particles. Here, different robotic systems are used in the art that can be used in conjunction with the present method. As respective systems are well-known in the prior art and are also commercially available (e.g. QIAsymphony®; QIAGEN), they do not need any detailed description here. In a further alternative system for processing magnetic particles, the sample comprising the magnetic particles are aspirated into a pipette tip and the magnetic particles are collected in the pipette tip by applying a magnet e.g. to the side of the pipette tip. The remaining sample can then be released from the pipette tip while the collected magnet particles remain due to the magnet in the pipette tip. The collected magnetic particles can then be processed further. Such systems are also well-known in the prior art and are also commercially available (e.g. BioRobot EZ1, QIAGEN) and thus, do not need any detailed description here.

The Kit According to the Fourth Aspect

According to a fourth aspect, a kit for performing the methods according to the present disclosure is provided, wherein the kit comprises:

(a) a solid phase comprising anion exchange groups for binding extracellular DNA; and (b) an acidic binding buffer comprising a buffering agent.

The solid phase (a) has one or more of the characteristics as disclosed herein in conjunction with the method of the first aspect for binding cfDNA in step (a). It is referred to the respective disclosure.

The acidic binding buffer (b) was likewise discussed above in conjunction with the method of the first aspect, step (a) where an according acidic binding buffer is added to the biological sample in order to prepare suitable binding conditions. It is again referred to the above disclosure which discloses suitable binding buffers, as well as suitable anion exchange groups. Suitable acidic binding buffers are also described in further detail below.

In embodiments, the kit comprises (a) magnetic anion exchange particles for binding extracellular DNA;

(b) an acidic binding buffer comprising a buffering agent;

(c) magnetic anion exchange particles for binding extracellular vesicles, wherein said anion exchange particles differ from the magnetic anion exchange particles (a), and (d) optionally an acidic reagent as defined in any one of items 92 to 96 of the invention as disclosed below.

Details of components (a) the magnetic anion exchange particles for binding extracellular DNA and (b) the acidic binding buffer comprising a buffering agent were described in detail above and are also disclosed in the further embodiments identified below. These reagents may be comprised in the kit according to the present invention and it is referred to the corresponding disclosure which also applies here. The same applies with respect to component (c), i.e. the magnetic anion exchange particles for binding extracellular vesicles that differ from the magnetic anion exchange particles (a). Suitable embodiments are described herein.

The magnetic anion exchange particles (c) may comprise anion exchange groups as defined in any one of items 49 to 68, preferably as defined in any one of items 58 to 64 as disclosed below, optionally wherein magnetic anion exchange particles (c) comprise anion exchange groups selected from histamine, polyethyleneimine and poly-histidine. The magnetic anion exchange particles for binding extracellular vesicles are also disclosed in detail above, in particular in conjunction with the methods according to the second and third aspect and it is referred to the respective disclosure which also applies in conjunction with the kit.

According to one embodiment, the kit comprises (c) magnetic anion exchange particles for binding extracellular vesicles comprising anion exchange groups selected from (i) oligo-histidine, wherein the number of histidine monomers is in the range of 4 to 18, such as 5 to 16, 6 to 14, 7 to 13 or preferably 8 to 12, and (ii) a histamine group, optionally wherein the anion exchange groups comprise 1 histamine group per anion exchange group. As disclosed herein, these anion exchange particles are well suitable for binding extracellular vesicles and/or extracellular RNA. The kit may additionally comprise different magnetic anion exchange particles for binding extracellular DNA which comprise anion exchange groups comprising a trialkylamine group or dialkylaminoalkyl group for cfDNA binding.

According to a particular embodiment, the kit comprises (c) magnetic anion exchange particles for binding extracellular vesicles comprising anion exchange groups selected from (i) polyethyleneimine; (ii) polyhistidine, (iii) oligo-histidine, (iv) histamine and (v) anion exchange groups comprising Bis-Tris groups. According to one embodiment the number of histidine monomers in the polyhistidine is at least 30. The kit may additionally comprise different magnetic anion exchange particles for binding extracellular DNA which comprise anion exchange groups comprising a trialkylamine group or dialkylaminoalkyl group for cfDNA binding.

The present disclosure also discloses the use of the kit according to the fourth aspect and as defined in the items relating to the kit in a method according to the first, second or third aspect (see also items 1 to 113 as disclosed below).

Further Embodiments

Embodiments of the present invention are described again and in further detail in the following. The present invention in particular discloses and provides for the following items:

1. A method for enriching extracellular DNA from a biological sample comprising extracellular DNA and extracellular vesicles, wherein the method comprises:
(a) preparing a binding mixture comprising
the biological sample,
a solid phase comprising anion exchange groups,
an acidic binding buffer comprising a buffering agent,
and binding extracellular DNA to the solid phase comprising anion exchange groups;

(b) separating the solid phase with the bound extracellular DNA from the remaining binding mixture, wherein the remaining binding mixture comprises extracellular vesicles.

2. The method according to item 1, comprising processing the remaining binding mixture to enrich one or more biological targets of interest therefrom, wherein processing optionally comprises
(c) enriching as biological targets extracellular vesicles and/or extracellular RNA from the remaining binding mixture.

3. A method for sequentially enriching (i) extracellular DNA and (ii) extracellular vesicles and/or extracellular RNA from a biological sample comprising extracellular DNA and extracellular vesicles, wherein the method comprises:
(a) preparing a binding mixture comprising
the biological sample,
a solid phase comprising anion exchange groups,
an acidic binding buffer comprising a buffering agent,
and binding extracellular DNA to the solid phase;
(b) separating the solid phase with the bound extracellular DNA from the binding mixture, wherein the remaining binding mixture comprises extracellular vesicles; and
(c) enriching extracellular vesicles and/or extracellular RNA from the remaining binding mixture.

4. A method for enriching extracellular vesicles and/or extracellular RNA from a biological sample comprising extracellular vesicles and non-target biomolecules, the method comprising:
(a) preparing a binding mixture comprising
the biological sample,
a solid phase comprising anion exchange groups,
an acidic binding buffer comprising a buffering agent,
and binding at least extracellular DNA as non-target biomolecule to the solid phase;
(b) separating the solid phase with the bound extracellular DNA from the binding mixture, wherein the remaining binding mixture comprises extracellular vesicles; and
(c) enriching extracellular vesicles and/or extracellular RNA from the remaining binding mixture.

5. The method according to any one of items 1 to 4, wherein the pH of the binding buffer is in a range of 2.5 to 6.5 or 3 to 6.5, such as 3.5 to 6, 3.7 to 5.5 or 4 to 5.2.

6. The method according to claim 5, wherein the pH of the binding buffer is ≤5.5.

7. The method according to claim 5 or 6, wherein the pH of the binding buffer is ≤5.

8. The method according to one or more of items 5 to 7, wherein the pH of the binding buffer is ≥3.5 or ≥3.8.

9. The method according to one or more of items 5 to 7, wherein the pH of the binding buffer is ≥4 or ≥4.2.

10. The method according to one or more of items 5 to 7, wherein the pH of the binding buffer is ≥4.5.

11. The method according to one or more of items 5 to 7, wherein the pH of the binding buffer is ≥4.7.

12. The method according to one or more of items 1 to 11, wherein in step (a) the pH of the binding mixture corresponds to the pH of the acidic binding buffer or deviates by ≤1.5 pH units from the pH of the binding buffer, preferably ≤1, ≤0.75 or ≤0.5 pH units.

13. The method according to any one of items 1 to 12, wherein in step (a) the pH of the binding mixture is in a range of 2.5 to 6.5, in particular 3 to 6.5, such as 3.5 to 6, 3.7 to 5.5 or 4 to 5.2.

14. The method according to item 13, wherein in step (a) the pH of the binding mixture is ≤6, ≤5.7 or ≤5.5.

15. The method according to item 13 or 14, wherein in step (a) the pH of the binding mixture is ≤5.

16. The method according to one or more of items 13 to 15, wherein in step (a) the pH of the binding mixture is ≥3.5 or ≥3.8.

17. The method according to one or more of items 13 to 15, wherein in step (a) the pH of the binding mixture is ≥4 or ≥4.2.

18. The method according to one or more of items 13 to 15, wherein in step (a) the pH of the binding mixture is ≥4.5.

19. The method according to one or more of items 13 to 15, wherein in step (a) the pH of the binding mixture is ≥4.7.

20. The method according to one or more of items 1 to 19, wherein in step (a) the pH of the binding mixture is lower than the pKa of the ionized form of the anion exchange groups of the solid phase, optionally wherein the pH is at least 1, at least 1.5, at least 2 or at least 2.5 unit(s) lower than the pKa.

21. The method according to one or more of items 1 to 20, wherein the in step (a) the pH of the binding mixture is within the buffering range of the binding buffer.

22. The method according to any one of items 1 to 21, wherein the acidic cfDNA binding buffer of step (a) comprises a buffering agent that has at least 1 pKa value, wherein the buffering agent has one or more of the following characteristics:

(i) the buffering agent has at least 2 pKa values, optionally wherein the different pKa values deviate by at least 0.75;

(ii) the one or more pKa values of the buffering agent are in a range of 1 to 6.5, optionally 1.2 to 5.5 or 1.2 to 5; and/or (iii) the buffering agent has at least one pKa value in a range of 1 to 4.

23. The method according to any one of items 1 to 22, wherein the acidic binding buffer of step (a) comprises a carboxylic acid based buffering agent.

24. The method according to item 23, wherein the buffering agent comprises a carboxylic acid and a salt of said carboxylic acid.

25. The method according to item 23 or 24, wherein the carboxylic acid (i) comprises 1 to 3 carboxylic acid groups;

(ii) is aliphatic; and/or (iii) is saturated.

26. The method according to any one of items 23 to 25, wherein the buffering agent comprises a buffer component selected from citrate, oxalate, formate, acetate, propionate, lactate and tartrate.

27. The method according to any one of items 23 to 26, wherein the binding buffer of step (a) has a pH of ≥3.5, preferably ≥3.8 or ≥4 and wherein the buffering agent comprises a buffer component selected from citrate, oxalate, formate, propionate, lactate and tartrate, preferably selected from citrate, oxalate, formate, lactate and tartrate, more preferably citrate.

28. The method according to any one of items 23 to 26, wherein the binding buffer of step (a) has a pH of ≥3.5, preferably ≥3.8 or ≥4 and wherein the buffering agent comprises oxalate or citrate as buffer component, preferably citrate.

29. The method according to any one of items 23 to 26, wherein the binding buffer of step (a) has a pH of ≥4.5, preferably ≥4.8 or ≥5 and wherein the buffering agent comprises acetate as buffer component.

30. The method according to one or more of items 1 to 28, wherein the binding buffer does not comprise acetate as main buffer component and optionally is free of acetate.

31. The method according to one or more of items 1 to 30, wherein the acidic binding buffer of step (a) comprises the buffering agent in a concentration of 1M or less, 0.7M or less, 0.5M or less or 0.25M or less.

32. The method according to one or more of items 1 to 31, wherein the acidic binding buffer of step (a) comprises the buffering agent in a concentration of at least 30 mM, such as at least 50 mM or at least 75 mM, optionally at least 80 mM.

33. The method according to one or more of items 1 to 32, wherein the acidic binding buffer of step (a) comprises the buffering agent in a concentration that lies in a range of 30 mM to 500 mM, such as 50 mM to 300 mM, 75 mM to 250 mM or 80 mM to 200 mM, optionally wherein the buffering agent is comprised in a concentration that lies in a range of 50 mM to 150 mM, such as 75 mM to 125 mM.

34. The method according to any one of the preceding items, wherein the binding mixture of step (a) does not comprise acetate as main buffer component, optionally wherein no acetate is added in step (a) to the biological sample.

35. The method according to one or more of items 1 to 34, wherein in step (a) the binding mixture comprises buffering agent originating from the binding buffer in a concentration of 0.5M or less, such as 0.35M or less, 0.3M or less or preferably 0.25M or less.

36. The method according to one or more of items 1 to 35, wherein in step (a) the binding mixture comprises the buffering agent originating from the binding buffer in a concentration of at least 15 mM, such as at least 25 mM or at least 35 mM, such as at least 40 mM.

37. The method according to one or more of items 1 to 36, wherein in step (a) the binding mixture comprises the buffering agent originating from the binding buffer in a concentration that lies in a range of 15 mM to 250 mM, 25 mM to 200 mM, 30 mM to 150 mM or 40 mM to 125 mM.

38. The method according to one or more of items 1 to 37, wherein the binding buffer comprises a salt.

39. The method according to one or more of items 1 to 38, wherein the binding buffer comprises a non-buffering salt.

40. The method according to one or more of items 1 to 39, wherein the binding buffer comprises a buffering salt as buffering agent and in addition thereto a non-buffering salt.

41. The method according to one or more of items 38 to 40, wherein the salt has at least one of the following characteristics:

it is a non-chaotropic salt;

it is an monovalent salt;

it is an alkali metal salt, preferably an alkali metal halide;

it is selected from sodium chloride, potassium chloride, lithium chloride and cesium chloride, preferably selected from sodium chloride and potassium chloride, more preferably the comprised salt is sodium chloride.

42. The method according to one or more of items 39 to 41, wherein the concentration of the non-buffering salt in the binding buffer is 1M or less, preferably 750 mM or less.

43. The method according to one or more of items 39 to 42, wherein the concentration of the non-buffering salt in the binding buffer is 500 mM or less, 370 mM or less, 300 mM or less or 250 mM or less.

44. The method according to one or more of items 1 to 43, wherein the total salt concentration in the acidic binding buffer of step (a) is 1M or less or 750 mM or less.

45. The method according to one or more of items 1 to 44, wherein the total salt concentration in the acidic binding buffer of step (a) is 500 mM or less, 370 mM or less, 300 mM or less or 250 mM or less.

46. The method according to one or more of items 1 to 45, wherein in the binding mixture the total concentration of salt(s) introduced into the binding mixture due to the addition of the binding buffer and optionally further reagent(s) is 1M or less or 750 mM or less.

47. The method according to one or more of items 1 to 46, wherein in the binding mixture the total concentration of salt(s) introduced into the binding mixture due to the addition of the binding buffer and optionally further reagent(s) is 500 mM or less, 370 mM or less, 300 mM or less or 250 mM or less.

48. The method according to one or more of items 1 to 47, wherein the solid phase that is used in step (a) is provided by particles, preferably magnetic particles.

49. The method according to one or more of items 1 to 48, wherein the solid phase comprises anion exchange groups of the same or different types.

50. The method according to one or more of items 1 to 49, wherein the anion exchange groups comprise at least one ionizable group as functional group, wherein preferably the ionizable group is ionizable by protonation.

51. The method according to one or more of items 1 to 50, wherein the ionisable groups of the anion exchange groups are provided on the surface of the solid phase as monomers, oligomers or polymers, wherein preferably, for cfDNA binding in step (a), a monomeric anion exchange group is used.

52. The method according to one or more of items 1 to 51, wherein the solid phase comprises anion exchange groups that comprise 1 to 20, 1 to 15 or 1 to 10 ionizable groups per anion exchange group.

53. The method according to item 52, wherein the solid phase comprises anion exchange groups that comprise 1 to 8, 1 to 6, 1 to 5, 1 to 3 or 1 to 2 ionizable groups per anion exchange group, wherein preferably, for cfDNA binding in step (a), a solid phase is used that comprise anion exchange groups that comprise 1 to 3, 1 or 2 or only 1 ionizable group(s) per anion exchange group.

54. The method according to one or more of items 1 to 53, wherein the solid phase comprises anion exchange groups that comprise per anion exchange group at least one, optionally only one ionizable group and a linker or spacer moiety.

55. The method according to one or more of items 1 to 54, wherein the solid phase comprises anion exchange groups that comprise at least one amino group, optionally wherein the solid phase comprises anion exchange groups that comprise only 1 amino group per anion exchange group for cfDNA binding in step (a).

56. The method according to one or more of items 1 to 55, wherein the solid phase comprises anion exchange groups that comprise at least one primary, secondary or tertiary amino group.

57. The method according to one or more of items 1 to 56, wherein the anion exchange group of the solid phase comprises a group selected from the group consisting of primary, secondary and tertiary amines of the formula $$(R)_3N, (R)_2NH, RNH_2 \text{ and/or } X\text{---}(CH_2)_n\text{---}Y$$

wherein
X is $(R)_2N$, RNH or $NH_2$,
Y is $(R)_2N$, RNH or $NH_2$,
R is independently of each other a optionally substituted linear, branched or cyclic alkyl, alkenyl, alkynyl or aryl substituent which may comprise one or more heteroatoms, preferably selected from O, N, S and P, and n is an integer in the range of from 0 to 20, preferably 0 to 18.

58. The method according to one or more of items 1 to 57, wherein the anion exchange groups comprise at least one amino group, wherein the amino group is part of a heterocyclic or heteroaromatic ring.

59. The method according to item 58, wherein the amino group is part of an imidazole ring.

60. The method according to item 59, wherein the anion exchange groups comprise histidine or histamine.

61. The method according to one or more of items 55 to 60, wherein the solid phase comprises anion exchange groups that comprise 1 to 20, 1 to 15 or 1 to 10 amino groups per anion exchange group.

62. The method according to one or more of items 55 to 60, wherein the solid phase comprises anion exchange groups that comprise 1 to 8, 1 to 6, 1 to 5, 1 to 4 or 1 to 2 amino groups per anion exchange group, wherein preferably, for cfDNA binding in step (a), a solid phase is used that comprise anion exchange groups that comprise 1 to 3, 1 or 2 or only 1 amino group(s) per anion exchange group.

63. The method according to one or more of items 1 to 62, wherein the anion exchange groups have a molecular weight per anion exchange group of 1000 Da or less, 500 Da or less or 300 Da or less.

64. The method according to one or more of items 1 to 63, wherein the anion exchange groups comprise at least one ionizable group having a pKa value of the ionized form, preferably the protonated form, within a range of 6 to about 13 or 7 to about 12.

65. The method according to item 64, wherein the pKa value is in the range from 8 to 12 or 9 to 11.5.

66. The method according to one or more of items 1 to 65, wherein the anion exchange groups comprise a trialkylamine group.

67. The method according to one or more of items 1 to 66, wherein the anion exchange groups comprise a dialkylaminoalkyl group for cfDNA binding and optionally no further ionizable groups for cfDNA binding.

68. The method according to item 66 or 67, wherein the alkyl groups independent of each other may comprise 1-6, 1 to 5 or 1 to 4 carbon atoms.

69. The method according to one or more of items 1 to 68, in particular 66 to 68, wherein the anion exchange group comprises a silane group.

70. The method according to item 69, wherein the solid phase comprises anion exchange groups that were provided by functionalization with trialkylsilanes, optionally N,N-dialkyl-3-aminoalkyl)trialkoxysilane, wherein the alkyl groups are selected from methyl-, ethyl-, propyl-, butyl-, or pentyl-groups.

71. The method according to one or more of items 1 to 70, wherein the anion exchange groups of the solid phase that is used for cfDNA binding are not provided by polyethylenimine.

72. The method according to one or more of items 1 to 71, wherein the anion exchange groups comprise at least one ionizable group, wherein said group is ionizable by protonation, wherein the ionizable group is protonated at the acidic pH of the binding mixture and is neutral or uncharged at a basic pH, such as at a basic pH of at least 8, at least 9 or at least 10.

73. The method according to one or more of items 1 to 72, wherein the solid phase comprises anion exchange groups that have a single positive charge per anion exchange group at the pH of the binding mixture, optionally at a pH ranging from $\geq 3$ to $\leq 6$ or $\geq 3.5 \leq 5.5$.

74. The method according to one or more of items 1 to 73, wherein the anion exchange groups of the solid phase and the binding conditions used in step (a) are adjusted to establish binding of the extracellular DNA to the anion exchange groups of the solid phase, while binding of extracellular vesicles to the anion exchange groups of the solid phase is reduced.

75. The method according to any one of items 61 to 74, wherein in step (a) magnetic anion exchange particles are used, which comprise at their surface anion exchange groups having one or more characteristics as defined in items 61 to 73 and wherein the binding buffer used in step (a) has one or more of the characteristics as defined in items 23 to 33.

76. The method according to item 75, wherein the anion exchange groups of the magnetic particles comprise a trialkylamine group and wherein the binding buffer has a pH of $\geq 3.5$, preferably $\geq 3.8$ or $\geq 4$ and wherein the buffering agent comprises a buffer component selected from citrate, oxalate, formate, propionate, lactate and tartrate, preferably selected from oxalate, formate, lactate and tartrate.

77. The method according to item 75 or 76, wherein the binding buffer comprises the buffering agent in a concentration that lies in a range of 30 mM to 500 mM, 50 mM to 300 mM or 75 mM to 250 mM and optionally comprises a non-buffering salt.

78. The method according to any one of items 75 to 77, wherein the total salt concentration in the binding buffer is 500 mM or less, 370 mM or less, 300 mM or less or 250 mM or less.

79. The method according to one or more of items 1 to 78, wherein the binding mixture of step (a) does not comprise one or more of the following:
    (i) a detergent or other agent that would cause substantial lysis of the comprised extracellular vesicles;
    (ii) an organic solvent; and/or
    (iii) a chaotropic salt in a concentration above 300 mM, above 250 mM, above 200 mM or preferably above 100 mM and optionally does not comprise a chaotropic salt at all.

80. The method according to one or more of items 1 to 79, wherein step (a) comprises contacting the biological sample with the binding buffer and the solid phase to prepare the binding mixture.

81. The method according to one or more of items 1 to 80, wherein the binding conditions in the binding mixture of step (a) are exclusively established by contacting the biological sample with the binding buffer and the solid phase.

82. The method according to one or more of items 1 to 81, wherein in step (a) the volume ratio of sample to binding buffer is selected from a range between 10:1 to 1:10, preferably 5:1 to 1:5, 4:1 to 1:4, 3:1 to 1:3, or 2:1 to 1:2, more preferably 1:1.

83. The method according to one or more of items 1 to 82, wherein after separating the solid phase with the bound extracellular DNA in step (b) the method comprises:
    (i) washing the extracellular DNA; and/or
    (ii) recovering, preferably eluting, the extracellular DNA from the solid phase.

84. The method according to one or more of items 1 to 83, comprising eluting the extracellular DNA from the solid phase by contacting the solid phase with the bound extracellular DNA with a basic elution solution, optionally wherein the pH of the elution solution is in the range of 8 to 13, such as 9 to 13, 10 to 13 or 11 to 12.

85. The method according to one or more of items 1 to 84, comprising analyzing the enriched extracellular DNA.

86. The method according to one or more of items 1 to 85, wherein step (c) comprises enriching extracellular vesicles (EV) and optionally non-vesicular RNA from the remaining binding mixture collected after step (b).

87. The method according to item 86, wherein extracellular vesicles are enriched in step (c) by at least one of the following binding to a solid phase, ultracentrifugation, ultrafiltration, gradients, affinity capture or a combination of the foregoing or wherein the extracellular vesicles are enriched in step (c) by size exclusion chromatography.

88. The method according to item 86 or 87, wherein step (c) comprises enriching extracellular vesicles by binding to an anion exchange surface of a solid phase.

89. The method according to item 88, wherein the solid phase is provided by
    a porous separation means, preferably a filter or membrane; or
    particles, preferably magnetic particles.

90. The method according to item 89, wherein step (c) comprises enriching extracellular vesicles by binding to magnetic anion exchange particles, wherein enriching comprises:
    (aa) contacting the remaining binding mixture collected after step (b) with magnetic anion exchange particles under EV binding conditions so that extracellular vesicles and optionally non-vesicular RNA bind to the anion exchange particles;
    (bb) separating the anion exchange particles with the bound extracellular vesicles; and
    (cc) optionally further processing the anion exchange particles.

91. The method according to item 90, wherein the binding conditions used in step (a) for binding cfDNA differ from the binding conditions used in step (c) for binding EVs and optionally extracellular RNA;
    optionally wherein the different binding conditions in step (a) and step (b) are achieved by one or more of the following:
    (i) in step (c) a solid phase comprising anion exchange groups is used that differs from the solid phase comprising anion exchange groups that is used in step (a), optionally wherein the charge density of the solid phase used in step (c) for binding extracellular vesicles is higher than the charge density of the solid phase used in step (a);
    (ii) the EV binding mixture of step (c) (aa) has a lower pH than the cfDNA binding mixture of step (a); and/or
    (iii) in step (c) a buffering agent is introduced into the EV binding mixture that differs from the buffering agent in the cfDNA binding mixture of step (a), optionally wherein the buffering agent promotes binding of EVs to the anion exchange groups of the solid phase, wherein preferably said buffering agent is acetate.

92. The method according to item 90 or 91, wherein the EV binding conditions of step (c) (aa) utilize an acidic pH wherein the EV binding pH is in the range of 2.5 to 5, such as 3 to 5, preferably 3 to 4.5, more preferably 3 to 4.

93. The method according to any one of items 90 to 92, wherein preparing the EV binding conditions in step (c) (aa) comprises adding an acidic reagent, optionally wherein the pH of the acidic reagent is in the range of 2.5 to 5.5, such as 2.5 to 5, optionally 3 to 5 or 3 to 4.5.

94. The method according to item 93, wherein the acidic reagent comprises a buffering agent, preferably a carboxylic acid based buffer, more preferably acetate.

95. The method according to item 93 or 94, wherein the EV binding mixture in step (c) (aa) comprises the buffering agent from the acidic reagent in a concentration of 100 mM to 1M, such as 200 mM to 700 mM, 300 mM to 600 mM or 350 mM to 550 mM, optionally wherein the buffering agent is acetate.

96. The method according to any one of items 93 to 95, wherein the acidic reagent used in step (c) (aa) for EV binding has a lower pH than the binding buffer of step (a) for cfDNA binding.

97. The method according to one or more of items 90 to 96, wherein in step (c) magnetic anion exchange particles are used which comprise anion exchange groups as defined in any one of items 49 to 68, preferably as defined in any one of items 58 to 64.

98. The method according to item 97, wherein step (c) comprises using magnetic particles comprising anion exchange groups selected from histamine, polyethylene-imine and poly-histidine for EV binding.

99. The method according to any one of items 86 to 98, wherein the method further comprises lysing enriched extracellular vesicles thereby providing a lysate that comprises vesicular RNA.

100. The method according to 99, comprising enriching RNA from the lysate.

101. The method according to any one of items 86 to 100, wherein step (c) comprises enriching total extracellular RNA from the remaining binding mixture, wherein the enriched extracellular RNA comprises vesicular RNA and optionally non-vesicular RNA.

102. The method according to item 101, wherein step (c) comprises enriching extracellular vesicles and optionally non-vesicular RNA from the remaining binding mixture collected after step (b), lysing the enriched extracellular vesicles to release the vesicular RNA and purifying RNA from the provided lysate, wherein the purified RNA comprises vesicular RNA and optionally non-vesicular RNA.

103. The method according to any one of items 90 to 102, wherein after separation step (bb), the solid phase with the bound extracellular vesicles is contacted with an acidic wash buffer that comprises a buffering agent, preferably acetate, optionally wherein the acidic wash buffer does not comprise a detergent.

104. The method according to any one of items 88 to 103, comprising recovering EVs bound to the anion exchange solid phase by elution and/or lysis, wherein recovering comprises at least one of the following:
    (i) providing a salt having a concentration of more than 1M;
    (ii) increasing the pH such that the anion exchange groups are not positive charged, such as at least pH 8;
    (iii) contacting the solid phase with the bound EVs with a reagent comprising phenol and a chaotropic salt.

105. The method according to any one of items 1 to 104, wherein a protease, optionally proteinase K, is added in one or more of the following step:
    prior to step (a);
    in step (a);
    after step (b);
    in step c); and/or
    after step c),
    in particular, after step b) and/or after step c).

106. The method according to any one of items 1 to 105, having one or more of the following characteristics: (i) wherein magnetic anion exchange particles are used in step (a) for binding extracellular DNA, and wherein at least steps (a) and (b) are performed in an automated manner using a robotic instrument, optionally wherein magnetic anion exchange particles are used in step (c) for binding extracellular vesicles, and wherein steps (a) to (c) are performed in an automated manner using a robotic instrument;
    (ii) wherein enriched cfDNA and enriched cfRNA are provided in separate fractions, preferably in separate eluate fractions, optionally wherein the enriched cfDNA and enriched cfRNA are analyzed differently; and/or
    (iii) wherein enriching encompasses isolating or purifying the target molecule of interest.

107. The method according to any one of items 1 to 106, wherein after step (a), at least 50% of the EVs and/or cfRNA remain in the binding mixture after separating the solid phase with the bound extracellular DNA from the binding mixture, optionally wherein the percentage is at least 60% or at least 70%.

108. The method according to any one of items 1 to 107, wherein the biological sample is or is derived from a body fluid or from a cell culture liquid.

109. The method according to item 108, wherein the biological sample is a sample obtained from a body fluid or cell culture liquid by removing cells.

110. The method according to item 108 or 109, wherein the biological sample is a cell-free or cell-depleted body fluid sample or cell culture liquid sample.

111. The method according to any one of items 108 to 110, wherein the cell-free or cell-depleted body fluid sample is or is derived from the following samples by removing cells: whole blood, plasma, serum, lymphatic fluid, urine, liquor, cerebrospinal fluid, ascites, milk, bronchial lavage, saliva, amniotic fluid, semen/seminal fluid, body secretions, nasal secretions, vaginal secretions, wound secretions and excretions.

112. The method according to any one of items 108 to 110, wherein the biological sample is selected from plasma, serum and urine, wherein urine is preferably cell-depleted or cell-free urine.

113. The method according to any one of items 1 to 112, wherein prior to step (a) the method comprises removing cells from a body fluid sample, whereby a cell-depleted body fluid sample is provided as biological sample that is contacted with the binding buffer and the solid phase in step (b) to prepare the binding mixture.

114. A kit for performing the method according to any one of items 1 to 113, wherein the kit comprises:
    (a) a solid phase comprising anion exchange groups for binding extracellular DNA;
    (b) an acidic binding buffer comprising a buffering agent.

115. The kit according to item 114, wherein the solid phase (a) has one or more of the characteristics as defined in any one of items 48 to 71.

116. The kit according to item 114 or 115, wherein the acidic binding buffer (b) has one or more of the characteristics as defined in any one of items 22 to 33 and 38 to 44.

117. The kit according to any one of items 114 to 116, wherein the solid phase (a) and the binding buffer (b) are as defined in any one of items 75-78.

118. The kit according to any one of items 114 to 117, comprising
    (a) magnetic anion exchange particles for binding extracellular DNA;
    (b) an acidic binding buffer comprising a buffering agent;
    (c) magnetic anion exchange particles for binding extracellular vesicles, wherein said anion exchange particles differ from the magnetic anion exchange particles (a), and
    (d) optionally an acidic reagent as defined in any one of items 92 to 96.

119. The kit according to item 118, wherein magnetic anion exchange particles (c) comprise anion exchange groups as defined in any one of items 49 to 68, preferably as defined in any one of items 58 to 64, optionally wherein magnetic anion exchange particles (c) comprise anion exchange groups selected from histamine, polyethyleneimine and poly-histidine.

This invention is not limited by the exemplary methods and materials disclosed herein, and any methods and materials similar or equivalent to those described herein can be used in the practice or testing of embodiments of this invention. Numeric ranges are inclusive of the numbers defining the range. The headings provided herein are not limitations of the various aspects or embodiments of this invention which can be read by reference to the specification as a whole.

As used in the subject specification, items and claims, the singular forms "a", "an" and "the" include plural aspects unless the context clearly dictates otherwise. The terms "include," "have," "comprise" and their variants are used synonymously and are to be construed as non-limiting. Further components and steps may be present. Throughout the specification, where compositions are described as comprising components or materials, it is additionally contemplated that the compositions can in embodiments also consist essentially of, or consist of, any combination of the recited components or materials, unless described otherwise. Reference to "the disclosure" and "the invention" and the like includes single or multiple aspects taught herein; and so forth. Aspects taught herein are encompassed by the term "invention".

It is preferred to select and combine preferred embodiments described herein and the specific subject-matter arising from a respective combination of preferred embodiments also belongs to the present disclosure.

EXAMPLES

It should be understood that the following examples are for illustrative purpose only and are not to be construed as limiting this invention in any manner. The below examples demonstrate that the method according to the present disclosure allows to enrich extracellular DNA (also referred to as "cell-free DNA" or "cfDNA") from biological samples comprising extracellular DNA and extracellular vesicles (EVs) (in particular cell-depleted body fluids such as plasma) by selectively binding extracellular DNA to the anion-exchange surface of a solid phase (e.g. magnetic beads) and separating the bound DNA from the remaining binding mixture. During the cfDNA binding step, binding of EVs to the solid phase can be reduced by choice of the binding conditions and the anion exchange groups of the solid phase, in particular by adjusting the pH of the used binding buffer. Different buffering agents and anion exchange groups can be used for preferential binding of cfDNA, while binding of EVs or cfRNA (also referred to as "cell-free RNA" or "extracellular RNA") is reduced. In embodiments, at least 50% of the EVs and cfRNA remains in the binding mixture after separation of the solid phase with the bound cfDNA.

The disclosed binding conditions thus allow to selectively capture extracellular DNA to the anion exchange surface without simultaneously capturing EVs, which contain most of the extracellular RNA. The binding conditions disclosed herein thus also allow to enrich extracellular DNA with reduced RNA contamination as is shown by the examples.

The cfDNA binding conditions used according to the invention advantageously do not promote the destruction of EVs. After separating the solid phase with the bound ccfDNA, intact EVs and other analytes such as non-vesicular RNA (e.g. certain miRNAs) are comprised in the remaining binding mixture (e.g. supernatant). The remaining binding mixture can thus be used for isolation of other analytes, such as EVs and/or total cfRNA. In this way, the present disclosure also provides methods for the sequential enrichment of extracellular DNA and other target analytes, such as the sequential enrichment of ccfDNA and EVs (or EV content), or cfDNA and total cfRNA into separate eluates.

Magnetic anion exchange particles (also referred to as "magnetic beads") used in the examples were either obtained from a commercial source or prepared as follows. Magnetic beads carrying carboxyl surface groups were coupled to different anion exchange groups using carbodiimide-based coupling. Following anion exchange groups were coupled as ligands:

polyethyleneimine (PEI—"AxpH" beads), poly-histidine (5,000-25,000 g/mol, n=32-160) and histamine.

Furthermore, anion exchange particles were prepared by coupling trialkyl amine groups, such as trialkylsilanes, to magnetic silica beads. (N,N-dialkyl-3-aminoalkyl)trialkoxysilanes, in particular DEAPS groups were coupled as ligands to prepare the mAnEx beads.

The ion balance beads are according to WO2010/130402. The charge-switch magnetic beads are described in WO02/48164. Other anion exchange groups may also be used in the method according to the present disclosure.

In the below examples, relative quantitation of isolated DNA, mRNA and miRNA was performed using the QuantiTect SYBR Green PCR Kit, QuantiTect SYBR Green RT-PCR Kit, and the miRCURY LNA miRNA PCR System (or for Example 2, the miScript® miRNA PCR System), respectively.

1. Example 1: Sequential Isolation of cfDNA and Total cfRNA

Example 1 shows the sequential isolation of ccfDNA and total ccfRNA into separate eluates using different magnetic anion exchange beads. Table 1 briefly summarizes the binding conditions used for cfDNA capture in the first binding step (step (a) of the present method) and for binding EVs and non-vesicular RNA in the second binding step (step (c) of the present methods) from the supernatant obtained after the first binding step.

TABLE 1

Experimental conditions used in Example 1. The 2x binding buffers and magnetic anion exchange particles used in the first binding step are shown, as well as the added compounds for the second binding step (acidifier and magnetic anion exchange particles).

| First binding step | | | | | Second binding step | | | |
|---|---|---|---|---|---|---|---|---|
| 2 x binding buffer | | | Solid | Anion exchange | Added acidifier | | Added solid | Anion exchange |
| pH | Buffer agent | Salt | phase | group | Type | Conc. | phase | group |
| 3.86 | citrate 100 mM | None | mAnEx | Monomeric (DEAPS) | acetate | 4M | p-His | poly-histidine |
| 3.70 | citrate 100 mM | NaCl 125 mM | mAnEx | Monomeric (DEAPS) | acetate | 4M | AxpH | polyethylenimine |

Plasma was prepared from blood collected from 2 subjects by centrifugation (10 min, 16000×g and 15 min 3000× g) and filtration (0.8 μm) to deplete cells and cell debris. The plasma was pooled.

Suspensions comprising anion exchange particles were vortexed and transferred into 2 mL reaction tubes. The particles were separated and the storage buffer removed.

cfDNA Binding and Recovery

For each condition tested (in duplicate) 1 ml of pooled plasma was mixed with 1 volume of the different 2× citrate binding buffers shown in table 1 above and inverted 5 times. The mixture (2 ml) was then added to the anion exchange particles, followed by 5 min end-over-end incubation of the binding mixture. The anion exchange particles were then separated for 3 min. The remaining binding mixture (supernatant) was collected for further processing to enrich cfRNA therefrom (see total cfRNA binding).

The separated anion exchange particles with the bound cfDNA were subjected to a protease digestion. The particles were contacted with 1.5 ml of a digestion buffer comprising proteinase K and incubated head-over-head for 30 min at room temperature. The particles were magnetically separated for 3 min and the supernatant removed. The proteinase K digestion buffer was chosen so that the cfDNA remained bound to the anion exchange surface to prevent loss of cfDNA.

The separated anion exchange beads were then washed and the bound cfDNA was eluted using an elution solution with a strong basic pH. Specifically, washing and elution was performed according to a manual version of the QIAsymphony ccfDNA protocol (QIAGEN). The obtained eluate was used for cfDNA analysis.

As reference, cfDNA was isolated from another 1 ml aliquot of the same plasma following a manual version of the QIAsymphony ccfDNA protocol (using 2 different amounts of magnetic particles).

Total cfRNA Binding and Recovery

Magnetic particles (polyethylenimine-functionalized particles ("AxpH" beads) or particles modified with poly-histidine ("pHis"-beads) were used as anion exchange particles for EV/cfRNA enrichment.

The supernatant collected after the first binding step was used for total cfRNA (comprising RNA from EVs and non-vesicular RNA) enrichment. The supernatant was adjusted to 440 mM acetate (by addition of 250 μL of a 4 M acetate stock buffer at pH of approx. 3.7 or 3.86, respectively). As noted above in Table 1, the binding buffer comprised 125 mM (or 0 mM) NaCl. After addition of the acetate buffer to the supernatant collected after the first binding step, the NaCl originating from the binding buffer comprising 125 mM NaCl is diluted to 56 mM.

2.25 ml of the adjusted supernatant was added to the anion exchange beads and incubated 10 min end-over-end. The magnetic anion exchange particles with the bound EVs/ cfRNA were separated for 2 min and the supernatant removed. The separated particles were washed with 1 ml wash buffer (e.g. 100 mM acetate pH 5) and separated for 2 min and the wash buffer removed.

700 μL QIAzol (QIAGEN), a phenol/guanidine based lysis reagent adjusted here to pH 8 was added to the washed anion exchange particles for elution/lysis of the bound analytes (cfRNA, EVs are lysed under these conditions, whereby vesicular RNA is released), followed by vortexing and 3 min end-over-end incubation. The anion exchange particles were separated for 2 min and the QIAzol eluate/ supernatant comprising the cfRNA was transferred into a 2 mL reaction tube. The eluate was vortexed briefly and incubated at room temperature for 2 min. 90 μL chloroform was added, vortexed (20 sec) and incubated for 2-3 min at room temperature. For separating the aqueous phase which comprises the recovered cfRNA, 15 min centrifugation was performed at 12000 g at 4° C. cfRNA was then purified from the aqueous phase using the miRNeasy Micro protocol (QIAGEN). The aqueous phase was transferred into a new 2 mL reaction tube followed by addition of 2× volume EtOH (100%) and mixing. The binding mixture was applied to an RNeasy MinElute Spin Column (centrifugation 8000×g 15 sec, loaded twice) followed by washing and elution of the bound nucleic acids. The so obtained eluate comprises total cfRNA (comprising vesicular and non-vesicular RNA) and thus the RNA that was still present in the supernatant collected from the first cfDNA binding step and enriched therefrom using the described method. It allows to efficiently isolate extracellular mRNA and miRNAs as is demonstrated herein.

For each condition, an additional aliquot of the same plasma sample was processed without ccfDNA capture (no addition of mAnEx beads) to control for any losses due to binding of EVs or ccfRNA together with ccfDNA to the mAnEx beads.

Moreover, for each particle type, an additional aliquot was processed with direct binding from 465 mM acetate buffer pH 4 (to control for any effect of the citrate buffer used in the DNA binding step).

Results

The results are shown in FIG. 1A-F below. cfDNA recovery from the first cfDNA binding step was determined based on detection of the 18S DNA (FIG. 1A). Total cfRNA recovery from the supernatant of the first binding step was determined by detecting RNA target molecules (FIG. 1B-F) that are predominantly found within EVs (vesicular RNA) or outside EVs (non-vesicular RNA). mRNA EEF2 (FIG. 1B), miRNAs let-7a (FIG. 1C) and miR-150 (FIG. 1D) were detected as vesicular RNAs. miR-122 (FIG. 1E) and miR-16 (FIG. 1F) were detected as non-vesicular RNAs.

The results show that ccfDNA was successfully enriched in the first binding step by binding to the magnetic anion exchange beads. The results confirm that using the method of the present disclosure ccfDNA can be recovered with similar efficiency as with the reference protocol for all conditions tested (FIG. 1A).

Furthermore, a high recovery of total cfRNA from the supernatant of the mAnEx beads was achieved, demonstrating that cfRNA (vesicular and non-vesicular) was not bound to the mAnEx beads and thus depleted in the first cfDNA binding step. The results show that total cfRNA can be efficiently enriched from the supernatant of the cfDNA binding step as shown by the successful isolation of vesicular as well as non-vesicular RNAs with good yield.

Figure 1B:
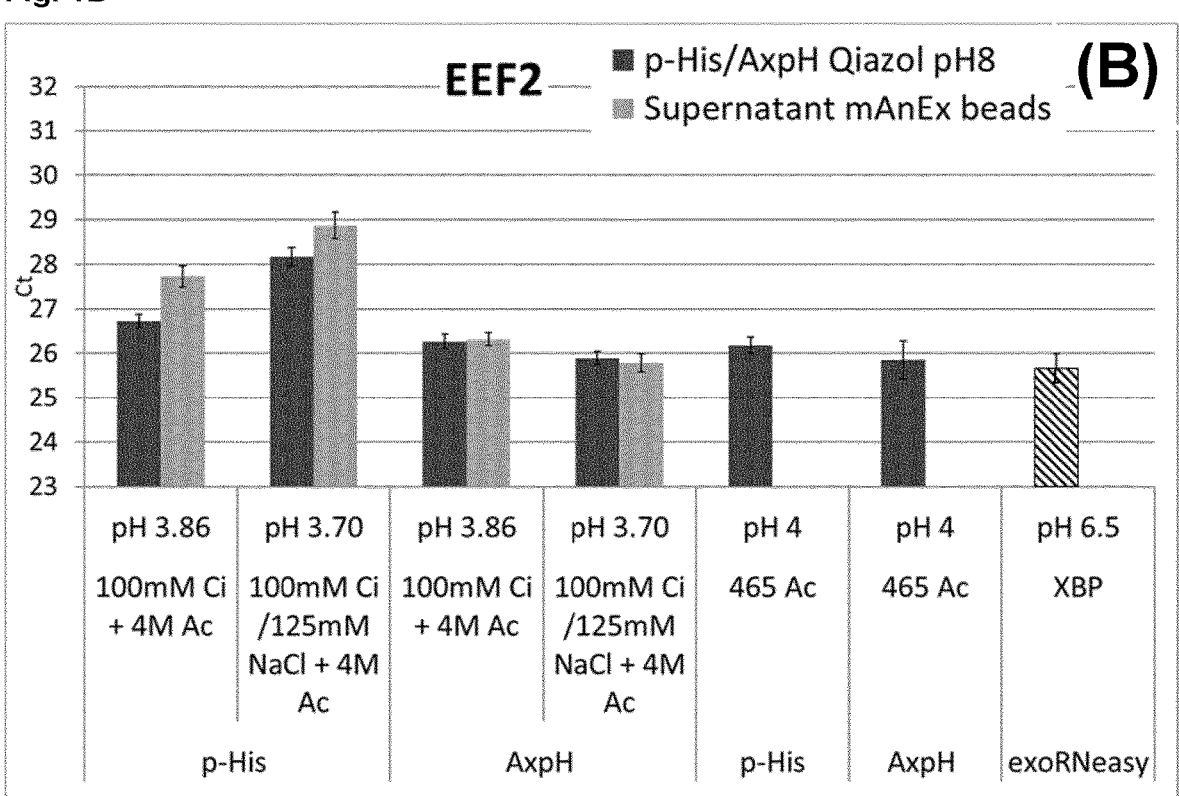
FIG. 1B: Shows results of Example 1, here recovery of
mRNA (EEF2). The dark blue columns ("p-His/AxpH
QIAzol pH8") show the results of the reference/control,
where cfRNA was isolated without prior cfDNA capture (no
mAnEx beads added to the first binding mixture). The light
blue columns ("supernatant mAnEx beads") show the results
(invention), when mAnEx beads are added to the first
binding mixture for cfDNA capture and wherein the cfRNA
is subsequently isolated from the remaining binding mix-
ture/supernatant, i.e. after separating the mAnEx beads with
the bound cfDNA. Also shown are the results of the further
controls, wherein the plasma samples were processed with
the exoRNeasy kit (striped column on the far right) and with
direct binding to p-His or AxpH beads from 465 mM acetate
buffer pH 4 (dark blue columns).
Figure 1C:
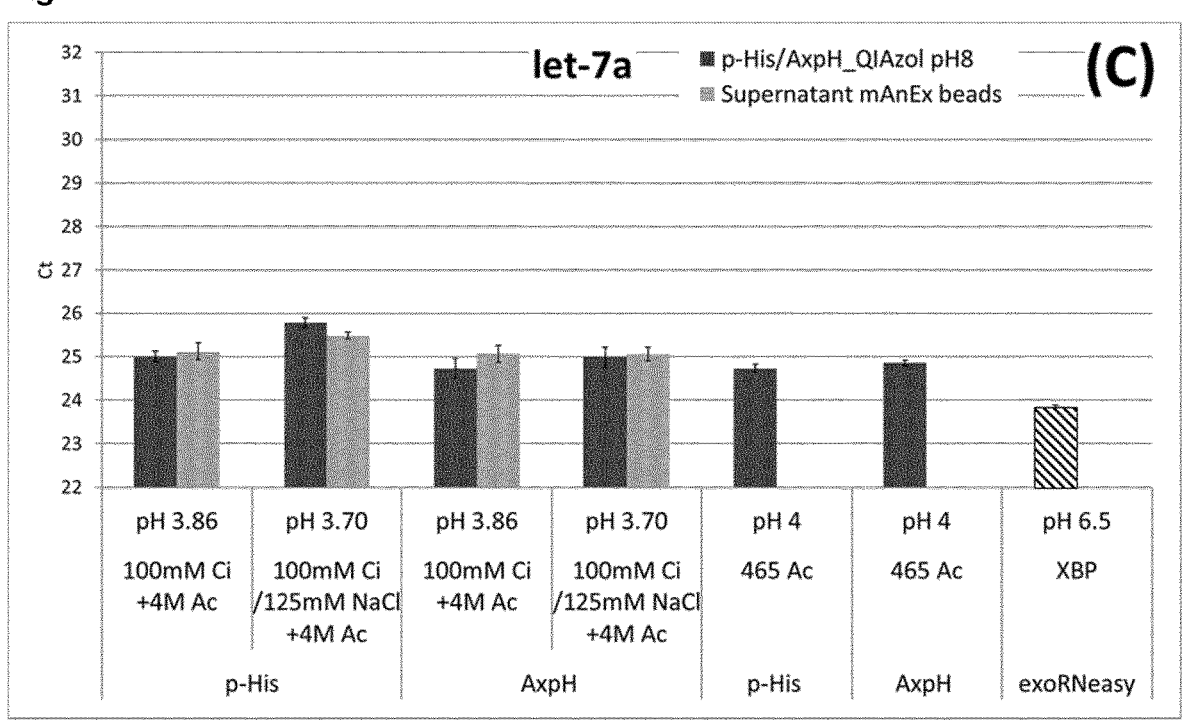
FIG. 1C: Shows results of Example 1, here recovery of
vesicular miRNA (let-7a). The legend otherwise corre-
sponds to FIG. 1B.
Figure 1D:
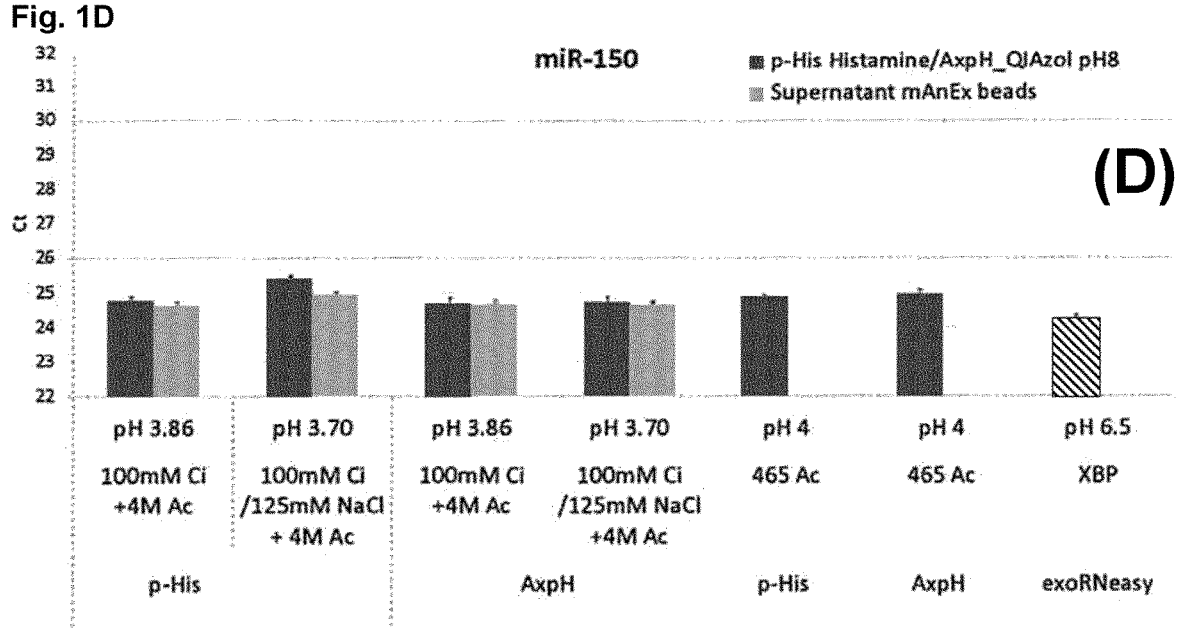
FIG. 1D: Shows results of Example 1, here recovery of
vesicular miRNA (miR-150). The legend otherwise corre-
sponds to FIG. 1B.
Figure 1E:
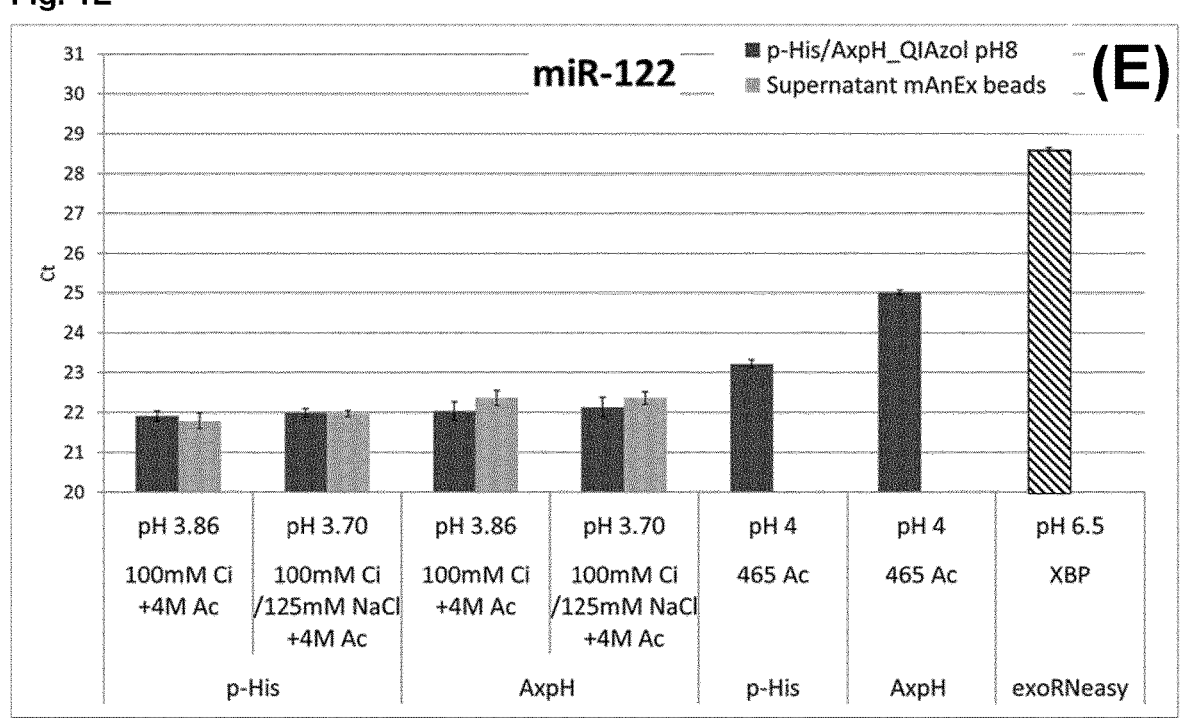
FIG. 1E: Shows results of Example 1, here recovery of
non-vesicular miRNA (miR-122). The legend otherwise
corresponds to FIG. 1B.
Figure 1F:
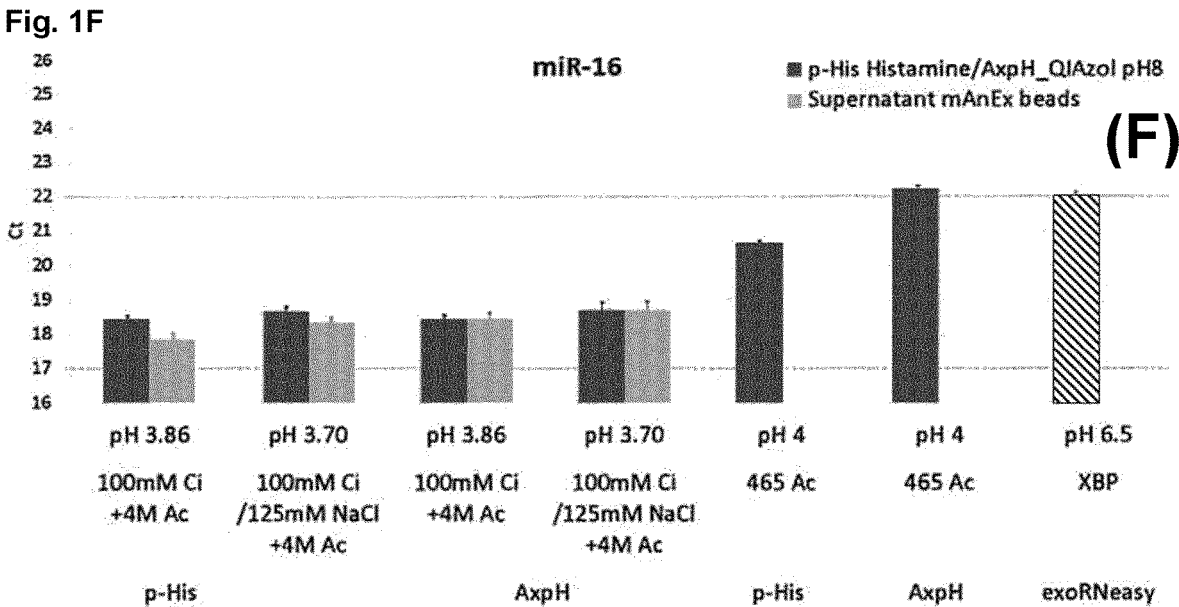
FIG. 1F: Shows results of Example 1, here recovery of
non-vesicular miRNA (miR-16). The legend otherwise cor-
responds to FIG. 1B.

Recovery of mRNA (EEF2) was comparable between exoRNeasy and direct binding to AxpH and pHis beads from acetate buffer alone as well as to AxpH from the citrate/acetate and citrate/acetate/NaCl buffer mixes, whereas with the pHis beads, binding efficiency was lower by approximately 1 CT with citrate/acetate and 2 CTs with citrate/acetate/NaCl (FIG. 1B).

Recovery of vesicular miRNA (let-7a in FIG. 1C and miR-150 in FIG. 1D) was comparable between all conditions tested and within about 1 CT of the positive reference exoRNeasy (1.5 CT for pHis beads and citrate/acetate/NaCl mix).

Interestingly, recovery of non-vesicular miRNA (miR-122 in FIG. 1E and miR-16 in FIG. 1F) was much higher compared to exoRNeasy using any of the test conditions. Given the assumption that binding of cell-free non-vesicular miRNA to the exoEasy membrane is prevented due to association with Ago2 (and perhaps other miRNA-binding proteins), this implies weakening of the Ago2-miRNA interaction at lower pH, and/or higher affinity of the Ago2-bound miRNA to the solid anion exchange matrix. Thus, non-vesicular RNA was purified with superior yield using the sequential method according to the present disclosure.

Therefore, total cfRNA can be sequentially isolated without any substantial loss in yield due to the first cfDNA binding step. Hence, example 1 shows that cfDNA and other analytes (EVs and/or cfRNA) can be enriched in a sequential manner from the same biological sample using the advantageous method according to the present disclosure. The provided protocol is flexible and due to the use of magnetic beads also automatable.

2. Example 2: Specificity of Different Anion Exchange Particles for Reduced or Effective Binding of EVs Using Different Binding Conditions Step (a) of the present method efficiently binds and thus captures cfDNA to the anion exchange surface of the solid phase, while EV binding to the solid phase is preferably low, to avoid substantial loss of EVs during step (a) and/or a contamination of the bound cfDNA. Hence, for step (a) binding conditions are preferred where cfDNA binding is high while EV binding is low, so that the EVs remain predominantly in the binding mixture from which they may then subsequently be recovered if desired (see Example 1 and step (c) of the methods where EVs are subsequently enriched). On the other hand, for enriching EVs by binding to an anion exchange solid phase (see e.g. step (c) of the disclosed methods), binding conditions are needed that efficiently capture the EVs to the anion exchange solid phase.

Example 2 analyses the extent of EV binding to four different anion exchange surfaces using binding buffers having different pH values, as shown in table 2 below.

TABLE 2

Gives an overview over the used binding conditions tested in Example 2 to analyze EV binding to different anion exchange particles using different acidic binding buffers. For the citrate based binding buffers, the pH, the buffering agent concentration and the salt is shown for the 2x binding buffer that is contacted with the biological sample and the different magnetic anion exchange particles. Citric acid/sodium citrate dihydrate can be used as citrate buffering agent. In addition, the commercially available XBP binding buffer of the exoEasy/exoRNeasy kit (pH 6.5) was tested in combination with the different magnetic anion exchange particles.

| | Buffer agent | | Salt | | | Anion exchange |
| pH | Type | Concentration | Type | Concentration | Solid phase | group |
| --- | --- | --- | --- | --- | --- | --- |
| 3 | citrate | 100 mM | NaCl | 370 mM | 0.5 mg AxpH | polyethylenimine |
| 4 | | | | | | |
| 5 | | | | | | |
| 6.5 | XBP binding buffer (ExoEasy/exoRNeasy kit) | | | | | |
| 3 | citrate | 100 mM | NaCl | 370 mM | 0.5 mg mAnEx | monomeric (DEAPS) |
| 4 | | | | | | |
| 5 | | | | | | |
| 6.5 | XBP binding buffer (ExoEasy/exoRNeasy kit) | | | | | |
| 3 | citrate | 100 mM | NaCl | 370 mM | 3 mg charge switch (Invitrogen-Kit (CS11204) | poly-His or Bis-Tris/PAA |
| 4 | | | | | | |
| 5 | | | | | | |
| 6.5 | XBP binding buffer (ExoEasy/exoRNeasy kit) | | | | | |
| 3 | citrate | 100 mM | NaCl | 370 mM | 0.5 mg ion balance beads | |
| 4 | | | | | | |
| 5 | | | | | | |
| 6.5 | XBP binding buffer (ExoEasy/exoRNeasy kit) | | | | | |

Plasma was prepared from blood collected from 2 subjects by centrifugation (10 min 1900×g and 15 min 3000×g) and filtration (0.8 μm) to deplete cells and cell debris. The plasma was pooled.

The suspensions comprising anion exchange particles were vortexed and transferred into 2 mL reaction tubes. Afterwards, the particles were separated and the storage buffer was removed.

For each condition tested (in duplicate) 1 ml of pooled plasma was mixed with 1 volume of the different 2× citrate binding buffers shown in table 2 above or 1 volume of the binding buffer XBP from the exoEasy/exoRNeasy kit (QIAGEN) and inverted 5 times. The mixture (2 ml) was then added to the anion exchange particles and vortexed, followed by 10 min end-over-end incubation of binding mixture. The anion exchange particles were then separated for 1 min. The remaining binding mixture (supernatant) was collected for later processing and analysis of the analytes/nucleic acids that were not captured/bound to the anion exchange particles in this binding step and thus are still comprised in the remaining binding mixture (see below).

The separated anion exchange particles comprising the bound analytes were washed, e.g. by adding 1 mL wash solution (e.g. 100 mM acetate, pH 5 or XWP buffer of the exoRNeasy kit (QIAGEN)), followed by vortexing, incubation, separation and removal of the wash supernatant. 700 μL QIAzol (QIAGEN, a phenol/guanidine based lysis reagent) was added to the washed anion exchange particles for elution/lysis of the bound analytes (nucleic acids, EVs), followed by vortexing and at least 1 min end-over-end incubation. The anion exchange particles were separated and the QIAzol eluate/supernatant was transferred into a 2 mL reaction tube. 90 μL chloroform was added, vortexed (20 sec) and incubated for 2-3 min at room temperature. For separating the aqueous phase which comprises the recovered nucleic acids, 15 min centrifugation was performed at 12000×g at 4° C. The aqueous phase was transferred into a new 2 mL reaction tube followed by addition of 2× volume EtOH (100%) and mixing. The binding mixture was applied to an RNeasy MinElute Spin Column (centrifugation 8000×g 15 sec, loaded twice) followed by washing step and elution of the bound nucleic acids (see miRNeasy Micro protocol, QIAGEN). The so obtained eluate comprises nucleic acids that were in the first binding step recovered from the binding mixture by binding to the anion exchange particles, either by direct binding to the anion exchange particles or because these nucleic acids were comprised in EVs that were initially bound to the anion exchange solid phase and from which the nucleic acids were then recovered by QIAzol extraction and subsequent purification.

The remaining binding mixture/supernatant fraction (that was collected after separation of the anion exchange particles, see above) was further processed to analyze whether EVs and/or non-vesicular RNA were predominantly removed therefrom by binding to the anion exchange particles in the binding step or instead predominantly remained in the binding mixture/supernatant (from which they can then be recovered, see Example 1). For this analysis, the collected remaining binding mixture/supernatant fraction was applied to exoEasy spin columns to capture any remaining EVs, again following the established exoRNeasy protocol (QIAGEN).

As reference, plasma was processed with an exoEasy column following the established prior art protocol.

By comparing (1) the detected amount of vesicular miRNA let-7a and beta-actin mRNA from eluates obtained after processing the separated anion exchange beads with (2) the detected amount of vesicular miRNA let-7a and beta-actin mRNA from eluates obtained after processing the remaining binding mixture/supernatant it can be analyzed whether EVs and/or non-vesicular RNA efficiently bind to and are thus captured by the used anion exchange particles under the tested binding conditions or not. This allows to identify binding conditions that predominantly do not capture EVs and/or non-vesicular RNA in the binding step, as it is desired for ccfDNA binding step (a) according to the methods of the present disclosure. It furthermore allows to identify binding conditions that do effectively capture EVs and/or non-vesicular RNA as it is e.g. desired when performing an EV enrichment step (c) according to the methods of the present disclosure.

Results

Figure 2:
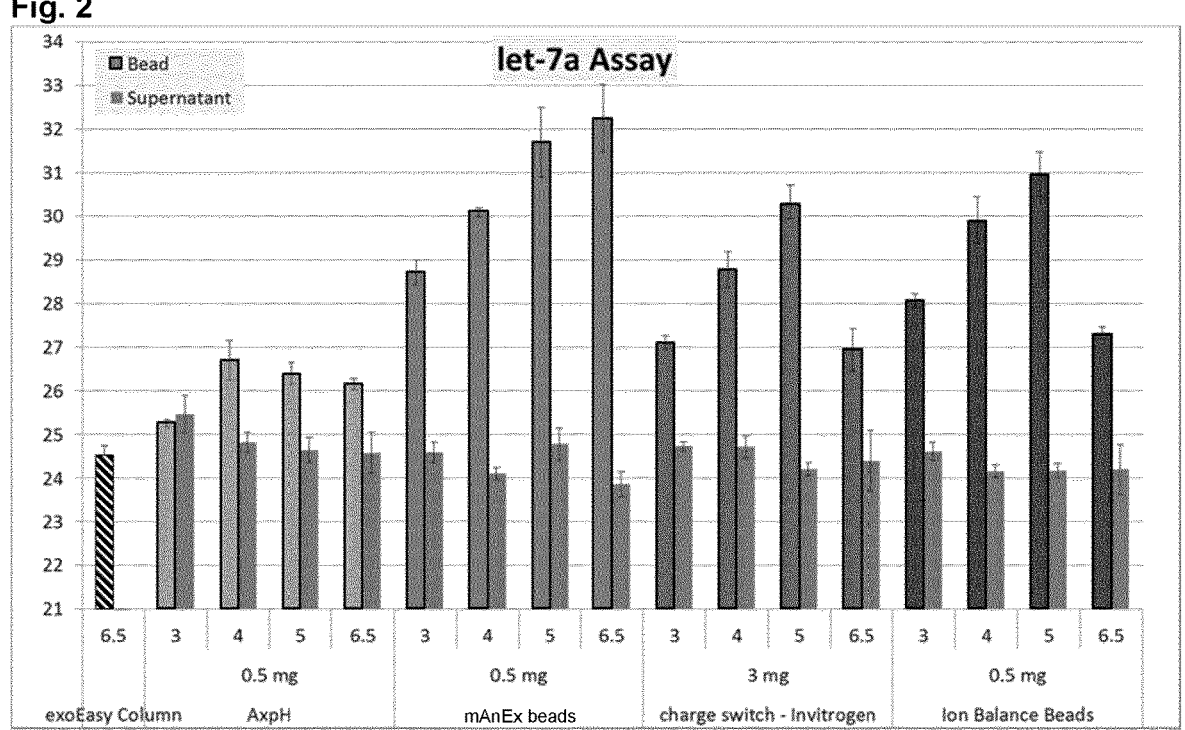
FIGS. 2 and 3: Shown are the results from Example 2,
here recovery of vesicular micro-RNA (let-7a) (see FIG. 2)
or vesicular beta-actin mRNA (see FIG. 3) when using
different magnetic anion exchange particles and acidic bind-
ing buffers at different pHs. Shown are the Ct-values,
wherein a lower Ct value indicates a higher target recovery.
The left columns (blue, "beads") show the results for the
nucleic acids recovered from the separated beads after
further processing, while the right columns (red, "superna-
tant") show the results for the nucleic acids recovered from
the separated remaining binding mixture/supernatant after
further processing for cfRNA recovery. As control the
exoEasy column and protocol was applied (striped column,
far left).
Figure 3:
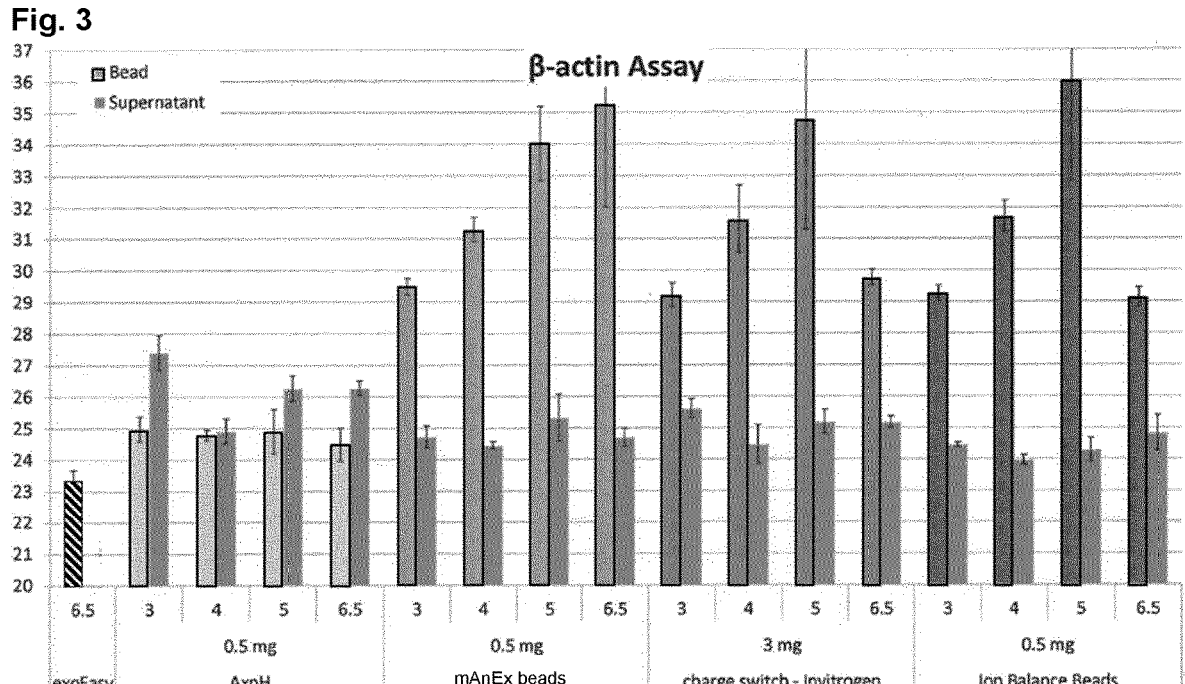

The results are shown in FIG. 2 (let-7a assay) and FIG. 3 (beta-actin). The results demonstrate that the binding conditions can be adjusted to either increase or reduce binding of EVs to the anion exchange surface of the solid phase. Such adjustment can be made by choosing the anion exchange groups of the solid phase and the binding buffer, in particular its pH.

The let-7a data demonstrates that in Example 2, EVs were most efficiently captured by the AxpH beads functionalized with polyethylenimine groups at pH 3, i.e. the lowest pH tested. Hence, these binding conditions may e.g. be used for enriching EVs by binding to AxpH beads (see methods that incorporate an EV enrichment step (c)). At higher pH values (4-6.5), EVs were less efficiently captured by the AxpH beads so that more EVs remained in the remaining binding mixture/supernatant with overall similar results for the tested pH range of pH 4-6.5. From the let-7a data it can furthermore be derived that EVs were not efficiently bound to the other three anion exchange particles tested. As can be seen, the Ct values are significantly higher for the nucleic acid eluates from the beads, indicating low EV binding to these particles under the tested conditions. In line with this finding, low Ct values were obtained from the eluates that were obtained by further processing the remaining binding mixture/supernatant for cfRNA recovery. This demonstrates that EVs predominantly remained therein after separation of the anion exchange particles with the bound cfDNA. This data further supports that binding of EVs can be adjusted by balancing the choice of the anion exchange surface with the used binding conditions and that a high degree of binding selectivity can be achieved. Moreover, a strong influence of the pH was detected, showing that a higher pH as tested leads to less EV binding. Hence, such binding conditions may e.g. be used in binding steps wherein low EV binding is desired (see e.g. cfDNA enrichment step (a) of the methods of the invention). In particular, the mAnEx particles showed less efficient EV binding under the tested conditions and are therefore particularly useful as anion exchange particles to efficiently capture cfDNA, while reducing binding of EVs so that EVs remain in the binding mixture/supernatant and can be recovered therefrom, if desired (see also Example 1).

The different performance of the different anion exchange particles under the tested binding conditions may be attributable to their charge density and/or the chemical nature of the anion exchange group. AxpH beads are functionalized with polyethylenimine and have a high surface charge density that apparently allows to efficiently capture EVs at low pH values. mAnEx and ion balance beads carry monomeric functional groups, suggesting a lower surface charge density which goes along with considerably less efficient capture of EVs, in particular at higher pH values. The exact surface chemistry of the charge-switch beads is unknown (kept confidential by manufacturer), but it is assumed to be poly-histidine or a polymer consisting of Bis-Tris coupled to polyacrylic acid.

3. Example 3: Influence of Buffer System and pH

Example 3 (3.1-3.3) demonstrates that different binding conditions can be used in order to selectively enrich cfDNA from biological samples comprising cfDNA and EVs, by selectively binding the cfDNA to anion exchange particles. The chosen binding conditions allow to reduce binding of EVs and non-vesicular RNA to the anion exchange solid phase. cfDNA is thus preferentially bound over EVs/non-vesicular RNA. This not only reduces contaminations of the bound cfDNA, but additionally allows to subsequently recover EVs and/or total cfRNA from the remaining binding mixture (after separating the anion exchange solid phase with the bound cfDNA). Inter alia, the influence of the pH and type of buffer agent in the binding buffer and type of buffer were analyzed for the first binding step by recovering DNA and RNA from the anion exchange particles by lysis/elution with QIAzol, pH adjusted to 8 to sequester the DNA to the aqueous phase (together with RNA), followed by wash and elution steps mirroring the miRNeasy Micro protocol (QIAGEN).

The anion exchange particles and pooled plasma were prepared as described in Example 2. For each condition tested (in duplicate) 1 volume of pooled plasma was mixed with 1 volume of the different 2× binding buffers shown in tables 3 to 5 below and inverted 5 times. The mixture (2 ml) was then added to the anion exchange particles. The binding mixture was subjected to 10 min end-over-end incubation. The anion exchange particles were then separated. If desired, the remaining binding mixture (supernatant) can be collected for later processing and recovery of the analytes/cfRNA that were not captured/bound to the anion exchange particles in this binding step. The separated anion exchange particles comprising the bound analytes were washed, e.g.

shaken (20 sec) and incubated for 2-3 min at room temperature. For separating the aqueous phase which comprises the recovered nucleic acids (DNA and RNA), 15 min centrifugation was performed at 12000 g at 4° C. The aqueous phase was transferred into a new 2 mL reaction tube followed by addition of 2× volume EtOH (100%) and mixing. The binding mixture was applied to an RNeasy MinElute Spin Column (centrifugation 8000×g 15 sec, loaded twice) followed by washing step and elution of the bound nucleic acids (see miRNeasy Micro protocol (QIAGEN)). The so obtained eluate comprises nucleic acids (DNA and RNA) that were in the first binding step recovered from the binding mixture by binding to the anion exchange particles, either by direct binding to the anion exchange particles (as it is the case for cfDNA) or because these nucleic acids were comprised in EVs that were initially bound to the anion exchange solid phase and from which the nucleic acids were then recovered by QIAzol (pH 8) extraction and subsequent purification.

Reference isolations from plasma were performed using exoRNeasy (QIAGEN; ref. for RNA), a manual version of the QIAsymphony ccfDNA protocol which also uses anion exchange beads for ccfDNA binding (QIAGEN; ref. for ccfDNA), and a modified version of exoRNeasy that also recovers DNA (termed 'exoD/R', ref. for both, DNA and RNA).

Example 3.1. Binding Buffers Comprising Citrate or Acetate at Different pHs

In this example acetate and citrate buffers having different pH values (see table 3 below) were tested and used for selective binding of cfDNA. The aim was to ensure efficient cfDNA binding, while co-isolation of cfRNA (inside and outside of EVs) in the cfDNA binding step (step (a)) should be minimized.

TABLE 3

Gives an overview over the used binding conditions tested in Example 3.1. Shown are the pH and the buffer agent (type and concentration) present in the 2x binding buffers tested which comprise no additional salt. Citric acid/sodium citrate dehydrate can be used as citrate buffering agent and HOAc/NaOAc trihydrate as acetate buffering agent.

Figure 4A:
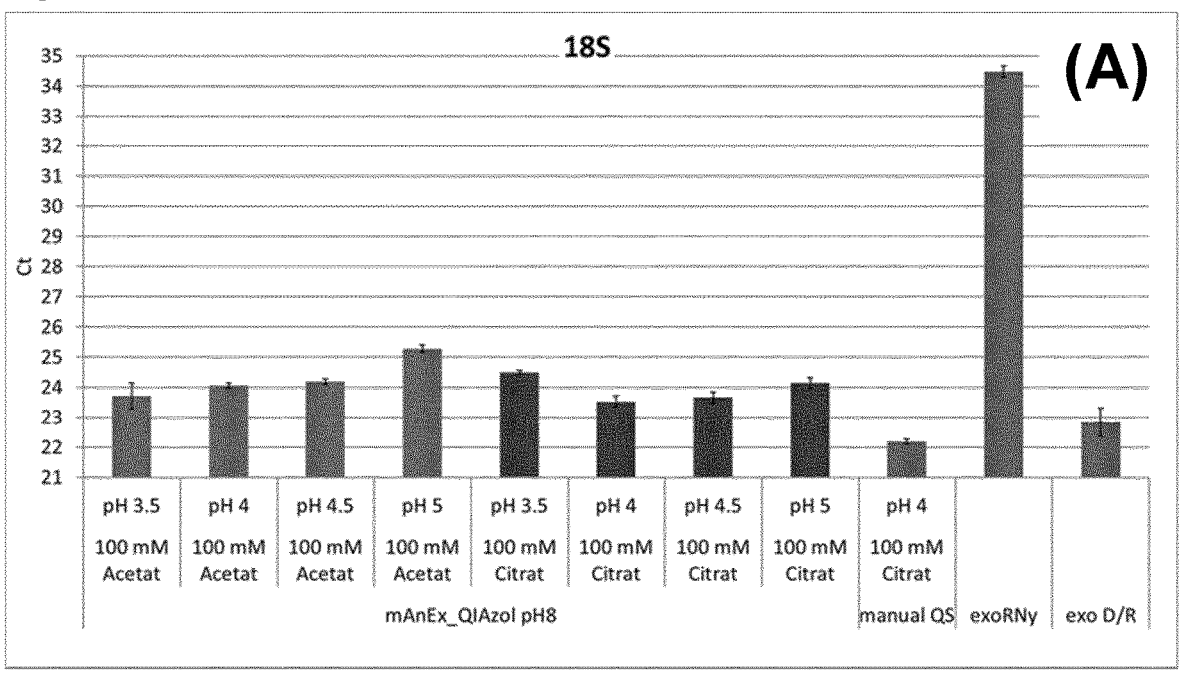
FIG. 4A: Shows results of Example 3.1, here the recovery
of cfDNA (18S DNA) in the binding step using mAnEx
beads and different binding buffers as indicated in the figure
and the used reference protocols.
Figure 4B:
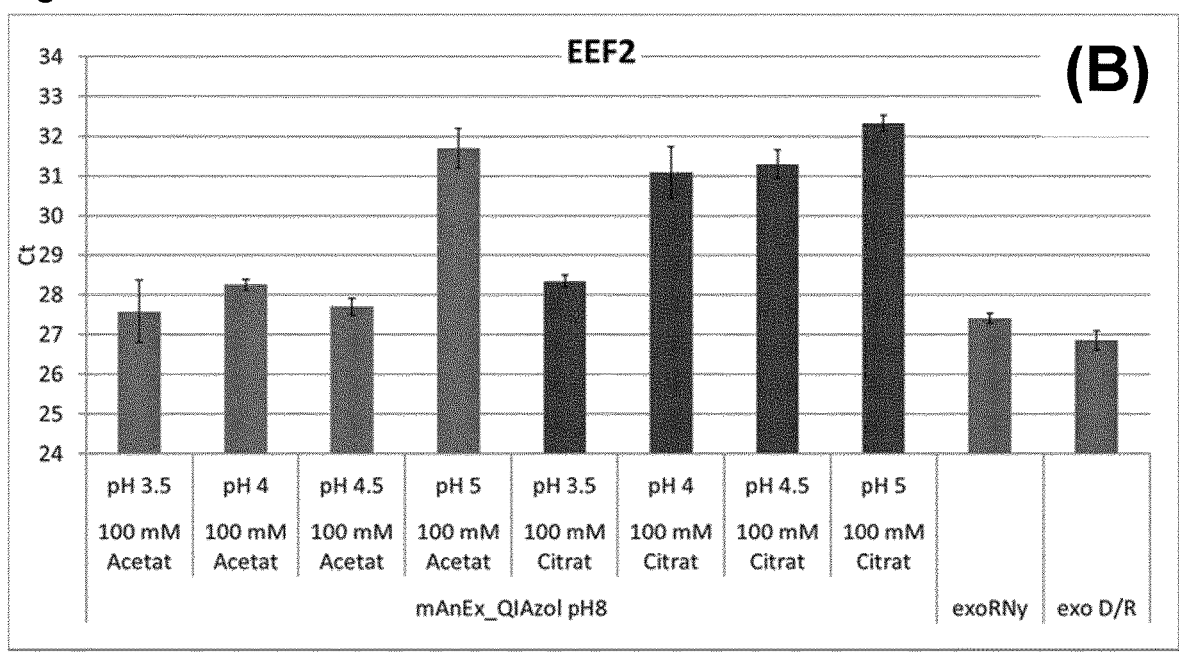
FIG. 4B: Shows results of Example 3.1, here the recovery
of vesicular mRNA (EEF2) in the binding step using mAnEx
beads and different binding buffers as indicated in the figure
and the used reference protocols.
Figure 4C:
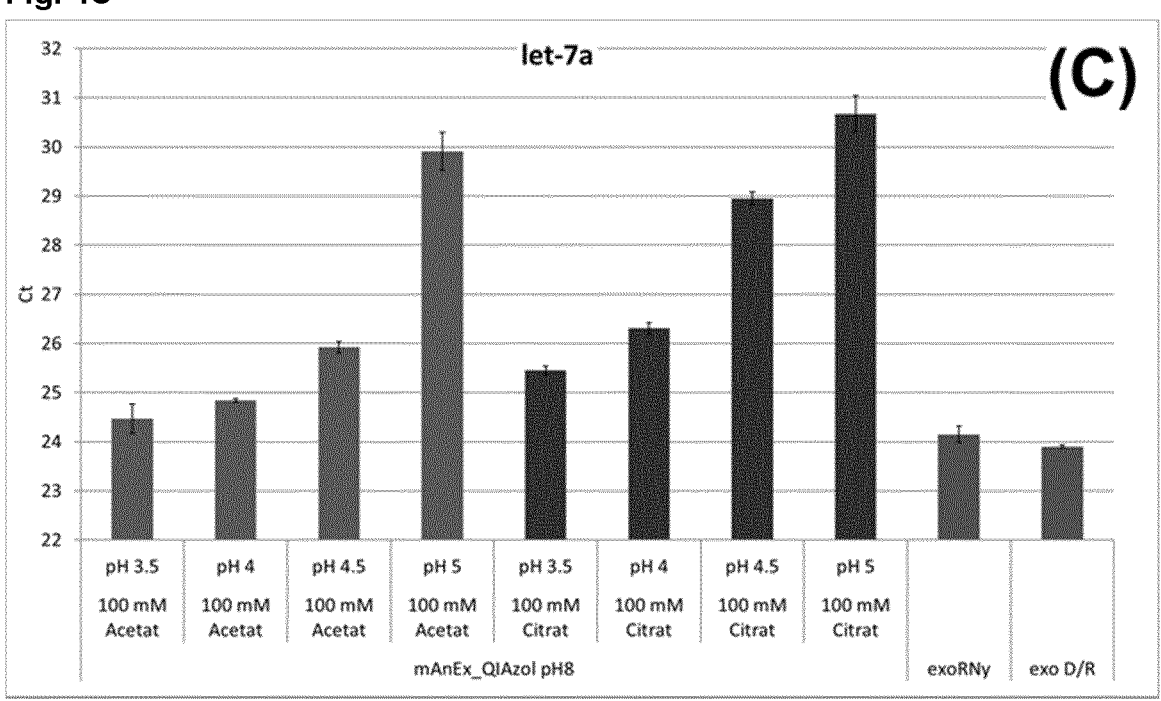
FIG. 4C: Shows results of Example 3.1, here the recovery
of vesicular miRNA (let-7a) in the binding step using
mAnEx beads and different binding buffers as indicated in
the figure and the used reference protocols.
Figure 4D:
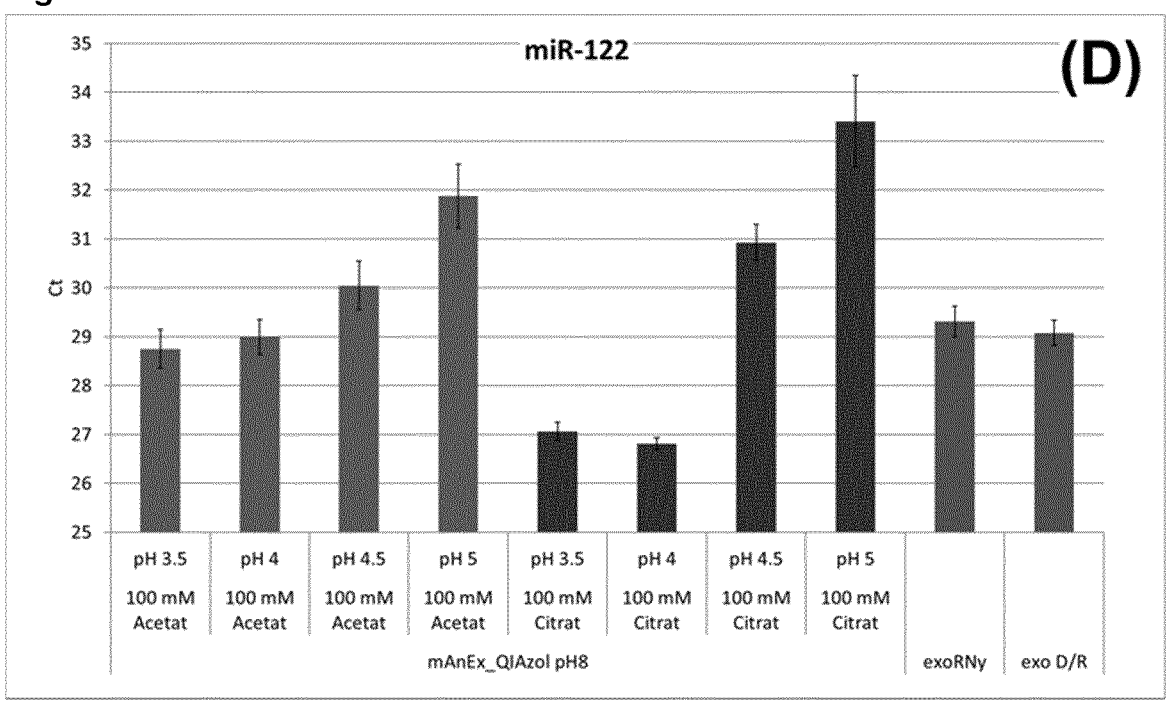
FIG. 4D: Shows results of Example 3.1, here the recovery
of non-vesicular miRNA (miR-122) in the binding step
using mAnEx beads and different binding buffers as indi-
cated in the figure and the used reference protocols.
Figure 4E:
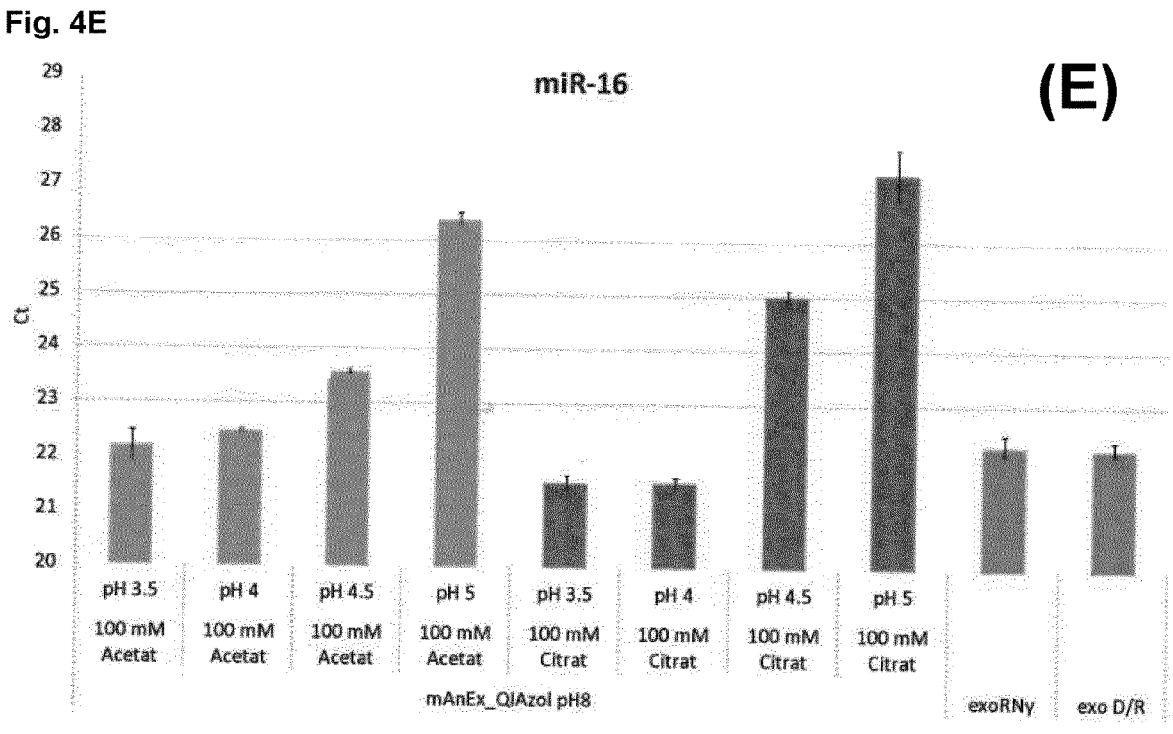
FIG. 4E: Shows results of Example 3.1, here the recovery of non-vesicular miRNA (miR-16) in the binding step using mAnEx beads and different binding buffers as indicated in the figure and the used reference protocols.

| PH | Buffer agent | | Salt | | Anion exchange | |
|----|------|---------------|------|---------------|-------------|-------|
| | Type | Concentration | Type | Concentration | Solid phase | group |
| 3.5 | citrate | 100 mM | none | | mAnEx | monomeric |
| 4 | | | | | | (DEAPS) |
| 4.5 | | | | | | |
| 5 | | | | | | |
| 3.5 | acetate | 100 mM | none | | mAnEx | monomeric |
| 4 | | | | | | (DEAPS) |
| 4.5 | | | | | | |
| 5 | | | | | | | by adding 1 mL wash solution (e.g. acetate, pH 5, 235 mM salt), followed by inverting the tubes 10 times, incubation, separation and removal of the wash supernatant. 700 µL QIAzol (QIAGEN), a phenol/guanidine based lysis reagent adjusted in this example to pH 8 was added to the washed anion exchange particles for elution/lysis of the bound analytes, followed by vortexing and 5 min end-over-end incubation. The anion exchange particles were separated for 2 min and the QIAzol eluate/supernatant was transferred into a 2 mL reaction tube. 90 µL chloroform was added, Results The results are shown in FIG. 4A-E below. The following target molecules were detected in the recovered eluate. With respect to the RNA, it is indicated whether the target is predominantly found within EVs (vesicular RNA) or outside EVs (non-vesicular RNA):

cfDNA: 18S DNA (FIG. 4A);

Vesicular RNAs: mRNA EEF2 (FIG. 4B), miRNA let-7a (FIG. 4C); and non-vesicular RNA: miR-122 (FIG. 4D), miR-16 (FIG. 4E).

Recovery of cfDNA

Recovery of cfDNA (FIG. 4A) with this QIAzol-based, combined DNA/RNA workflow for elution of the nucleic acids from the anion exchange particles is apparently lower than in the previous examples, and compared to the reference isolations. However, between the different binding buffers used cfDNA recoveries are very similar, with the exception of acetate at the highest pH tested (pH 5), where cfDNA recovery was lower. The more complex QIAzol-based elution/extraction workflow was used in example 3 to be able to additionally determine the selectivity of the binding conditions for cfDNA binding because this workflow allows to recover DNA and RNA and thus allows to analyze whether and to which extent EVs/non-vesicular RNA bind under these conditions to the anion exchange particles and are co-isolated together with the cfDNA (see FIGS. 4B to 4E).

As described herein, the elution of bound cfDNA from the anion exchange beads can also be achieved by simpler elution techniques, such as adding an elution solution having a basic pH value as is described herein (see also Example 1) and also known in the art. This is advantageous and can also be performed in an automated manner.

Non-Enrichment of EVs and Non-Vesicular cfRNA Species

Recovery of RNA from inside EVs (FIGS. 4B+C) shows a marked decrease (higher CT values) at pH values >4.5 for acetate and >3.5 for citrate, respectively, indicating that selective binding of cfDNA is considerably improved under these conditions. The majority of EVs thus remains intact in the binding mixture and are not co-enriched with the cfDNA. Therefore, these conditions are particularly favorable for cfDNA binding step (a).

Recovery of non-vesicular miR-122 (FIG. 4D), which is assumed to be associated with Ago2 protein (and thereby protected from endogenous RNases in plasma) was higher using citrate buffer at low pH, compared to acetate. The same was observed for the non-vesicular miR-16 (FIG. 4E). Presumably, under these conditions the association of the miRNA with Ago2 is either abolished, or weakened sufficiently to allow binding of the RNA to the anion exchange surface.

At lower pH values, efficiency of EV binding (indicated by recovery of the contained vesicular RNA species) to mAnEx beads is almost as high as for exoRNeasy (and much higher than in example 2 with the NaCl-containing binding buffers). Surprisingly, the tendency to bind EVs to the anion exchange surface is higher in acetate buffer compared to citrate buffer at the same pH. Hence, binding of EVs to the anion exchange surface/depletion of EVs during the cfDNA binding step is at the same pH also influenced by the used buffer agent.

Example 3.2. Binding Buffers Comprising Acetate and Formate at Different pH

The experiment described as example 3.1 was repeated using the same acetate buffers in comparison to formate buffers at pH 3-4.5. The binding buffers are listed in Table 4 below.

TABLE 4

Gives an overview over the used binding conditions tested in Example 3.2. Shown are the pH and the buffer agent (type and concentration) present in the 2x binding buffers tested which comprise no additional salt. HOAc/NaOAc trihydrate can be used as acetate buffering agent.

| | Buffer agent | | Salt | | Solid | Anion exchange |
| pH | Type | Concentration | Type | Concentration | phase | group |
|---|---|---|---|---|---|---|
| 3.5 | acetate | 100 mM | | none | mAnEx | monomeric |
| 4 | | | | | | (DEAPS) |
| 4.5 | | | | | | |
| 5 | | | | | | |
| 3 | formate | 100 mM | | none | mAnEx | monomeric |
| 3.5 | | | | | | (DEAPS) |
| 4 | | | | | | |
| 4.5 | | | | | | |

Further details on the performed experimental steps were explained above.

Results

The results are shown in FIG. 5A-E below based on detection of the same target molecules as in Example 3.1.

Figure 5A:
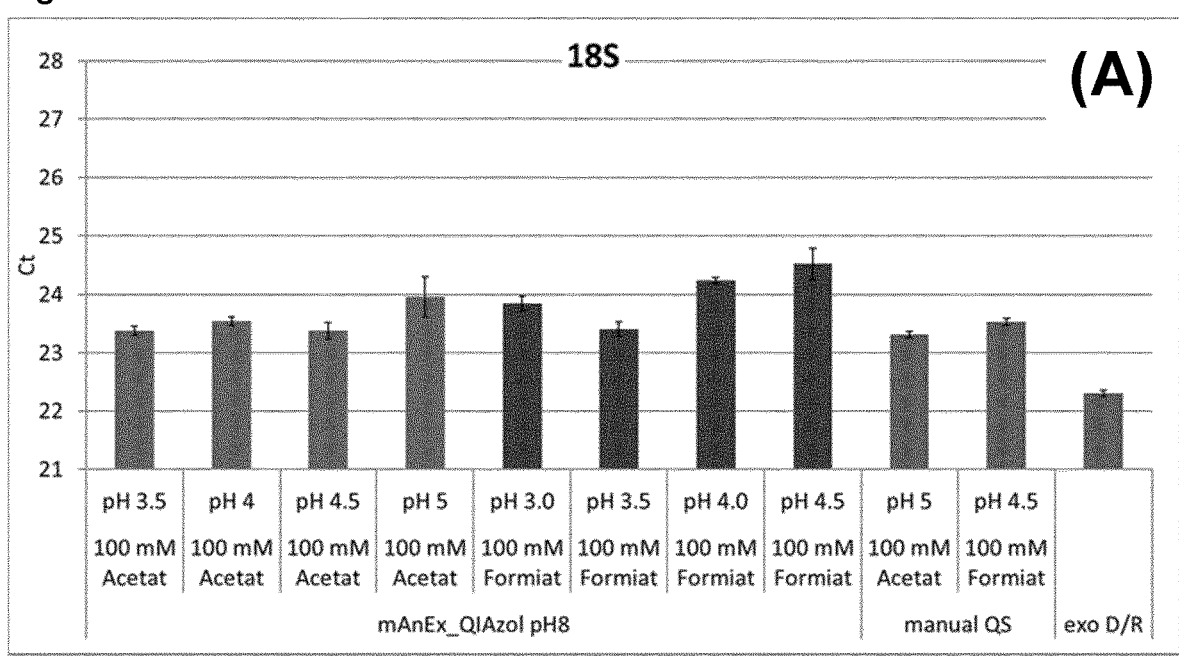
FIG. 5A: Shows results of Example 3.2, here the recovery of cfDNA (18S DNA) in the binding step using mAnEx beads and different binding buffers as indicated in the figure and the used reference protocols.
Figure 5B:
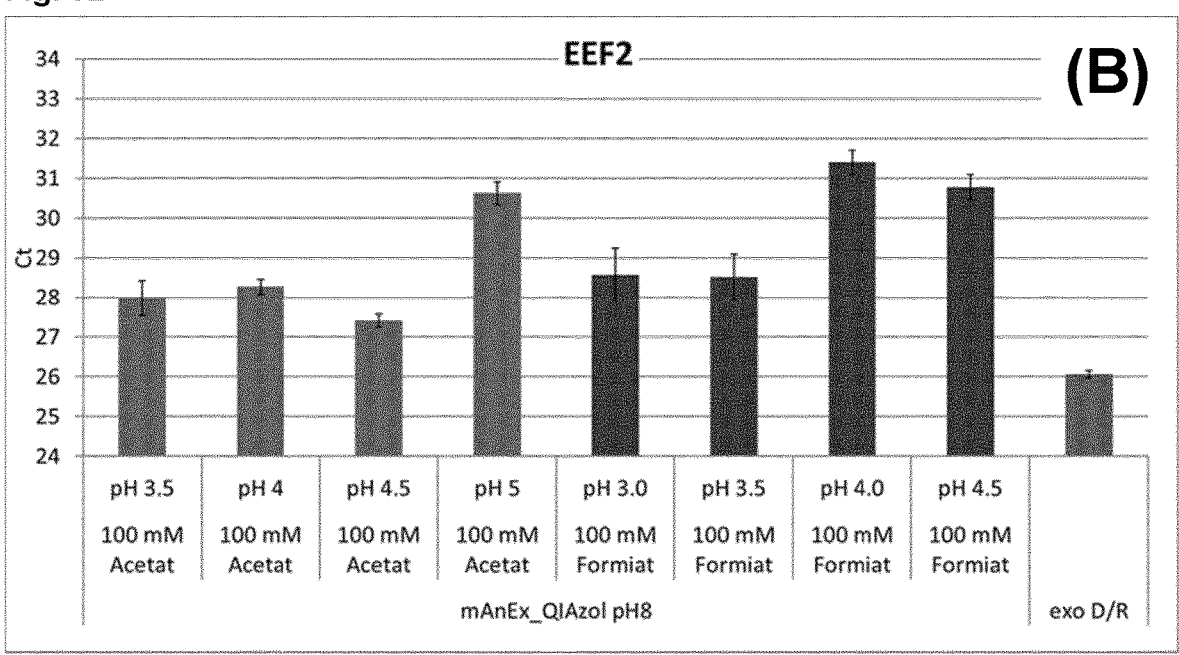
FIG. 5B: Shows results of Example 3.2, here the recovery of vesicular mRNA (EEF2) in the binding step using mAnEx beads and different binding buffers as indicated in the figure and the used reference protocols.
Figure 5C:
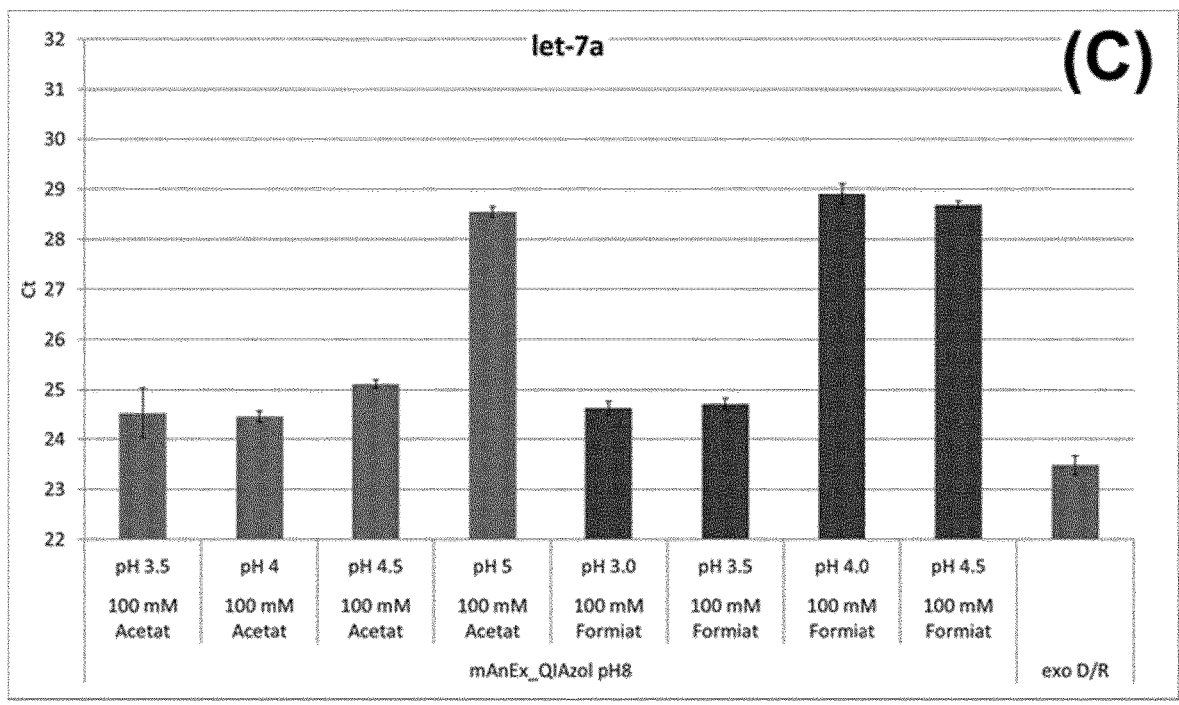
FIG. 5C: Shows results of Example 3.2, here the recovery of vesicular miRNA (let-7a) in the binding step using mAnEx beads and different binding buffers as indicated in the figure and the used reference protocols.
Figure 5D:
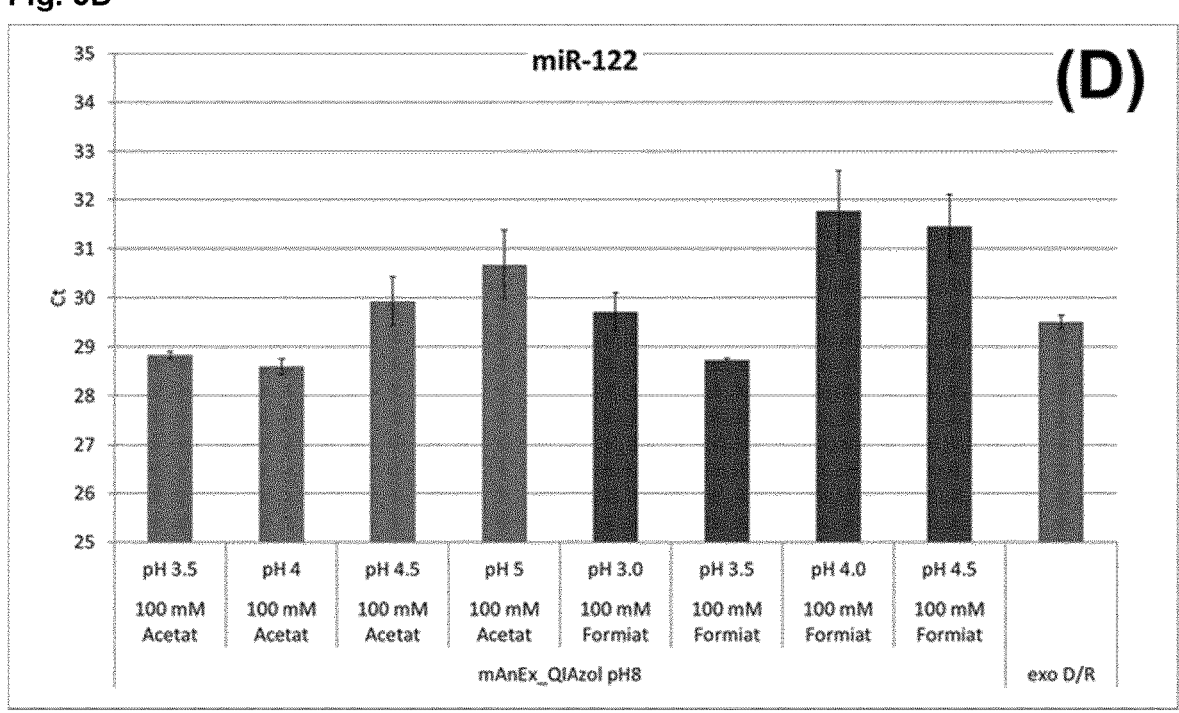
FIG. 5D: Shows results of Example 3.2, here the recovery of non-vesicular miRNA (miR-122) in the binding step using mAnEx beads and different binding buffers as indicated in the figure and the used reference protocols.
Figure 5E:
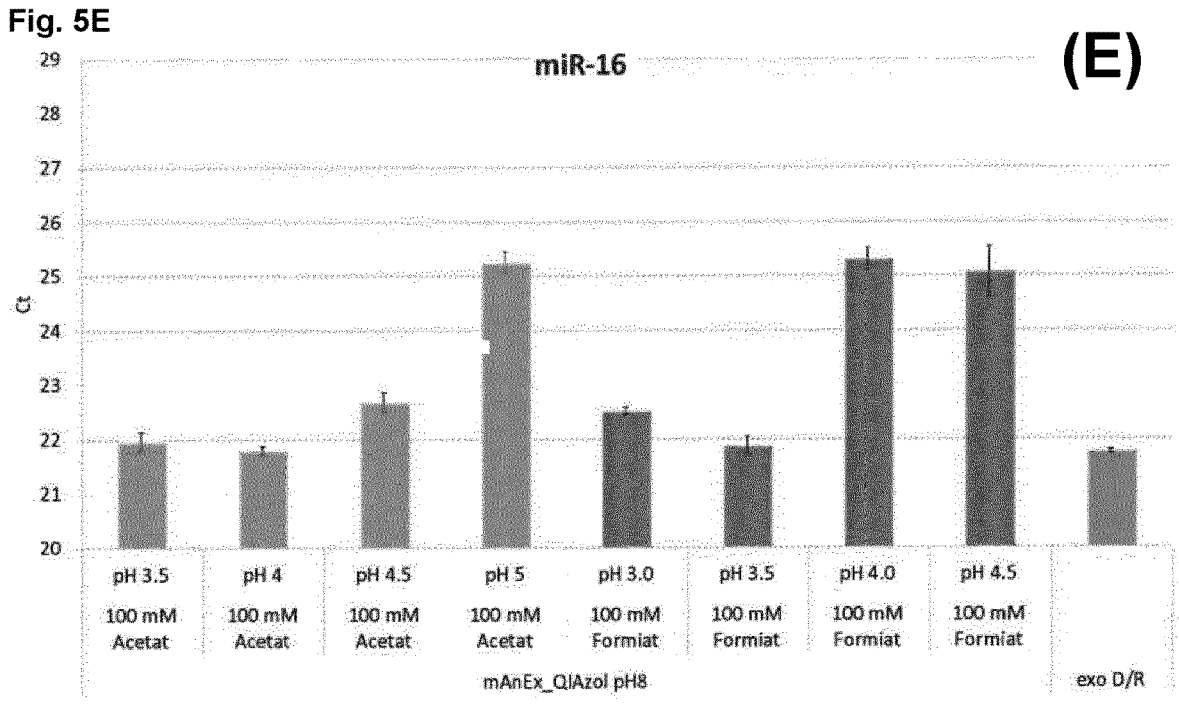
FIG. 5E: Shows results of Example 3.2, here the recovery of non-vesicular miRNA (miR-16) in the binding step using mAnEx beads and different binding buffers as indicated in the figure and the used reference protocols.
Figure 6A:
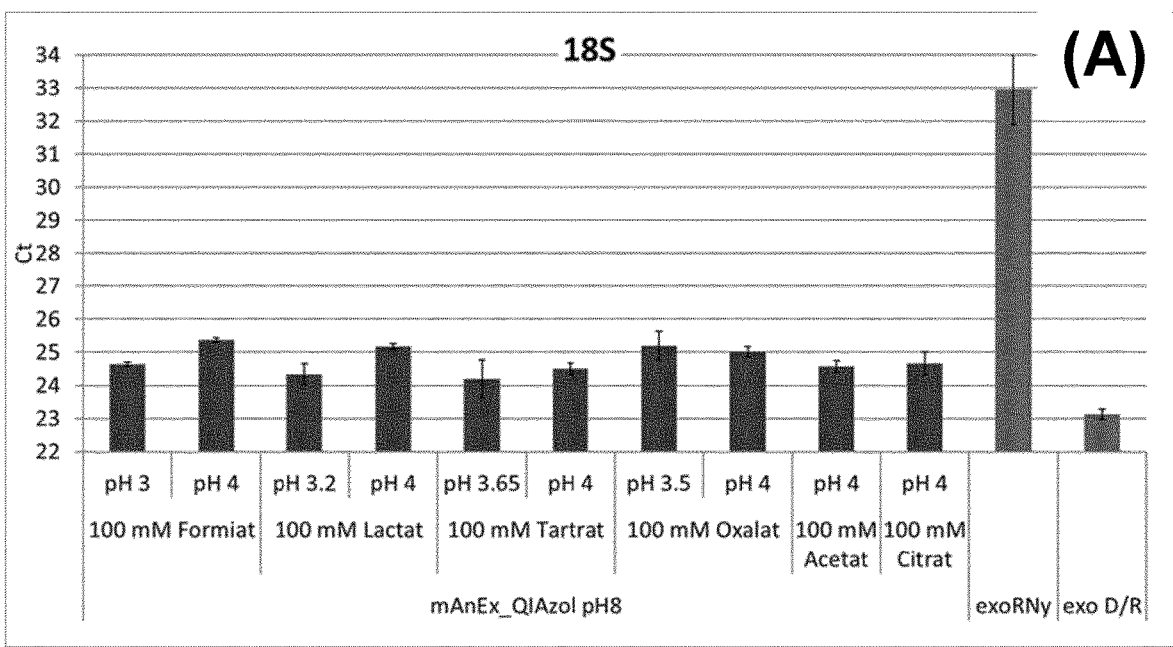
FIG. 6A: Shows results of Example 3.3, here the recovery of cfDNA (18S DNA) in the binding step using mAnEx beads and different binding buffers as indicated in the figure and the used reference protocols.
Figure 6B:
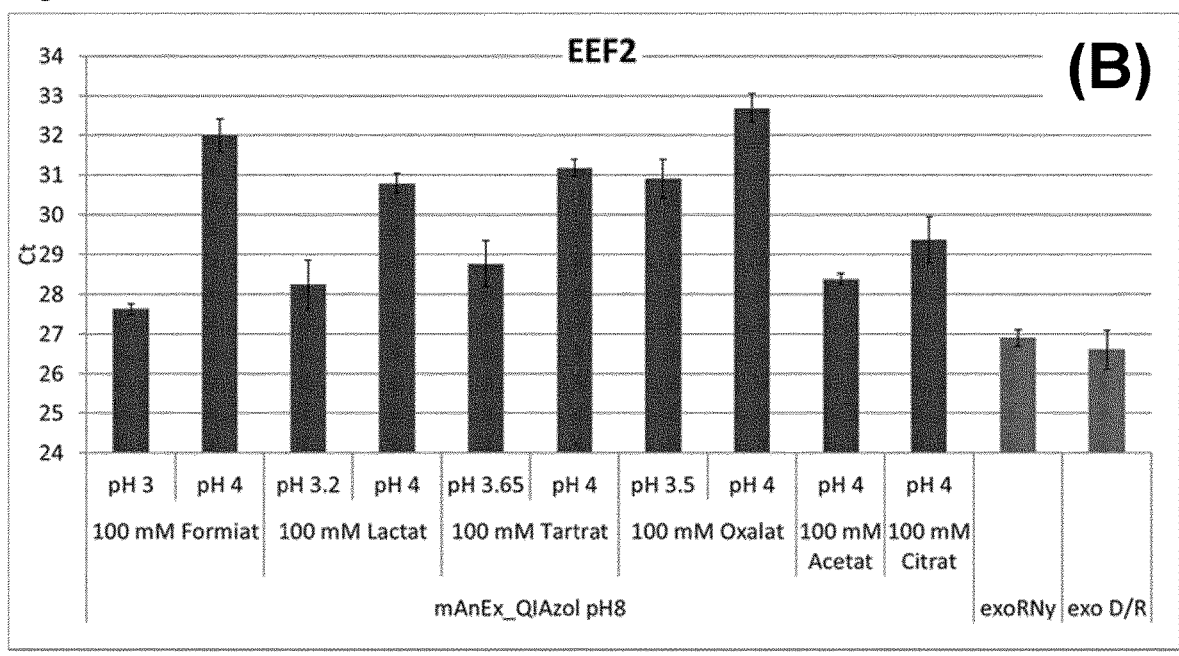
FIG. 6B: Shows results of Example 3.3, here the recovery of vesicular mRNA (EEF2) in the binding step using mAnEx beads and different binding buffers as indicated in the figure and the used reference protocols.
Figure 6C:
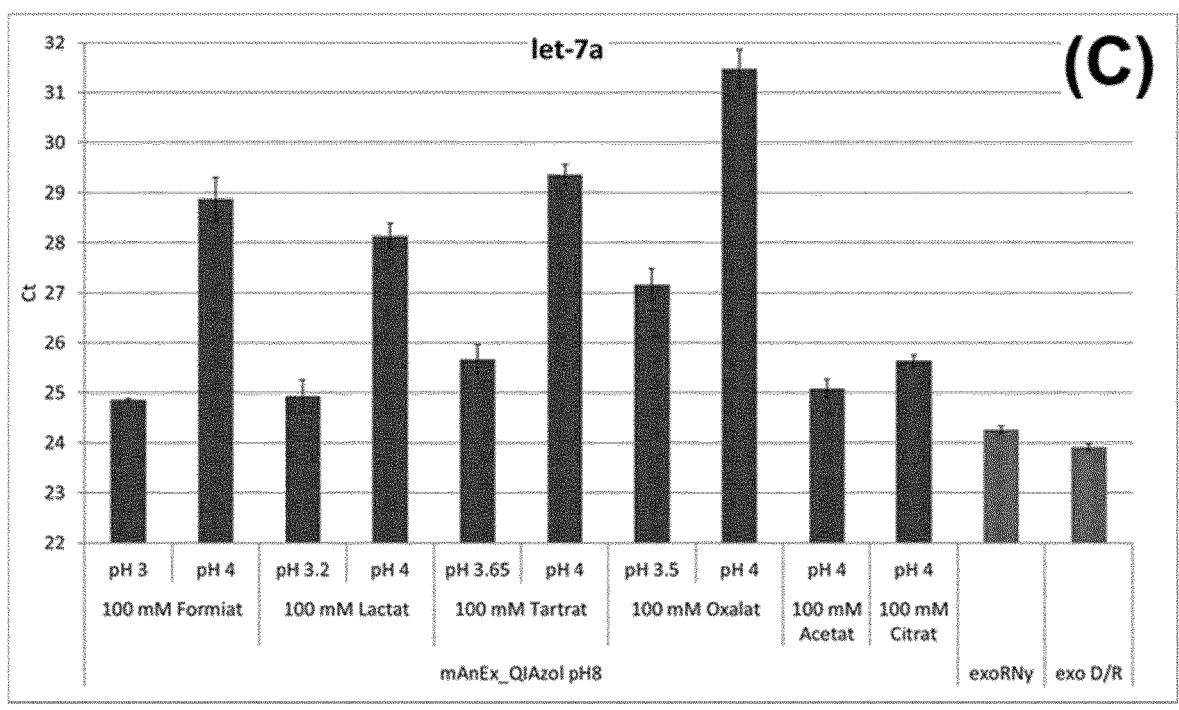
FIG. 6C: Shows results of Example 3.3, here the recovery of vesicular miRNA (let-7a) in the binding step using mAnEx beads and different binding buffers as indicated in the figure and the used reference protocols.
Figure 6D:
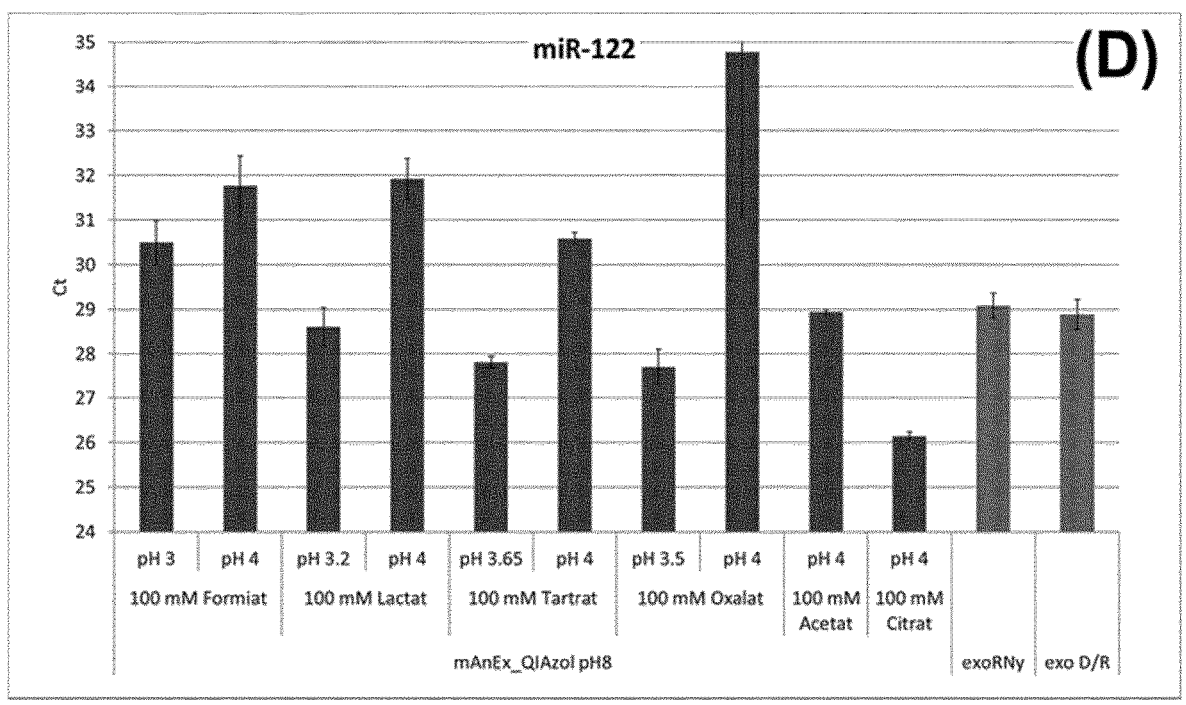
FIG. 6D: Shows results of Example 3.3, here the recovery of non-vesicular miRNA (miR-122) in the binding step using mAnEx beads and different binding buffers as indicated in the figure and the used reference protocols.
Figure 6E:
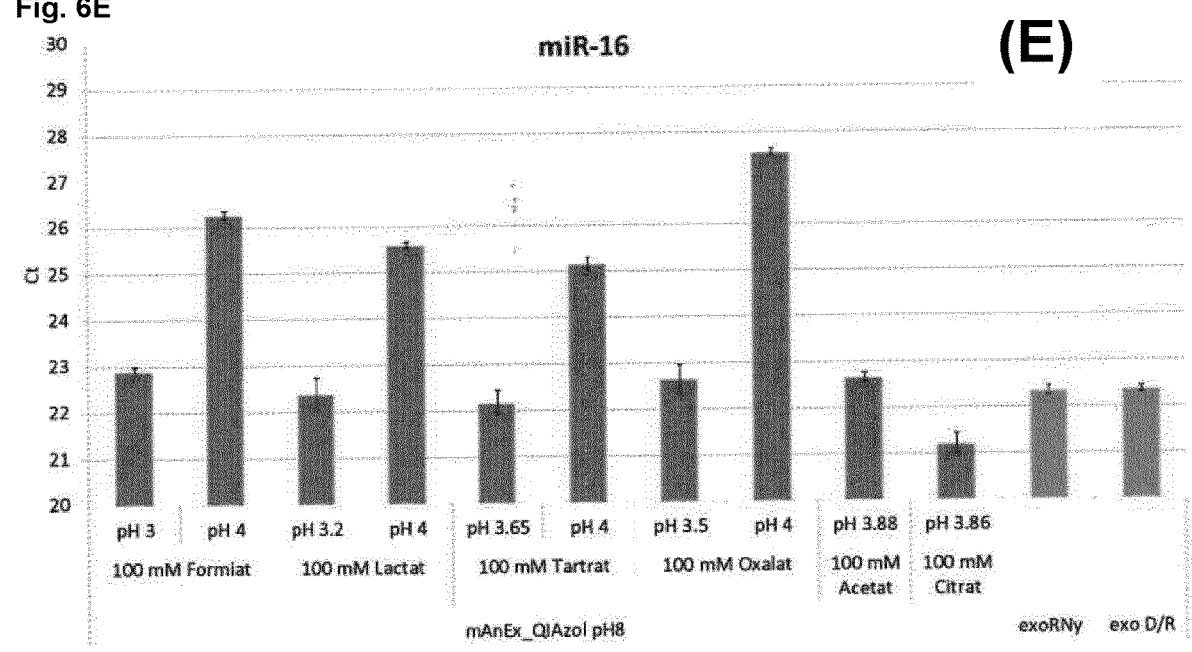
FIG. 6E: Shows results of Example 3.3, here the recovery of non-vesicular miRNA (miR-16) in the binding step using mAnEx beads and different binding buffers as indicated in the figure and the used reference protocols.

Example 3.2. confirms the results obtained with acetate in example 3.1. cfDNA binding to the anion exchange beads and subsequent recovery is robust and very similar between the different binding conditions tested. The cfDNA yield using the method according to the present disclosure was comparable to the yield obtained with manual QIAsymphony protocol and the exo D/R protocol (FIG. 5A). However, EV and non-vesicular cfRNA binding to the anion exchange beads can be adjusted by varying the pH so that they remain predominantly in the binding mixture/supernatant, whereby co-isolation together with the cfDNA may be greatly reduced (see FIG. 5B-E). The data indicates that the higher the pH value of the binding buffer, the fewer EVs bind to the anion exchange beads, i.e. the more EVs are present in the supernatant (see e.g. FIG. 5C). Example 3.2 furthermore shows that the tested binding conditions with formate as buffer agent show greatly reduced binding of EVs to the beads at pH >3.5 already.

Example 3.2. moreover shows that further buffer agents are suitable to provide selective binding conditions, i.e. conditions at which cfDNA binds to the anion exchange particles, while EVs and non-vesicular ccfRNA binding is reduced.

Example 3.3. Binding Buffers Comprising Further Buffer Systems at Different pH The experiment described as example 3.1 was repeated using the same different buffer systems at pH values between 3 and 4. The binding buffers are listed in Table 5 below.

TABLE 5

Gives an overview over the used binding conditions tested in Example 3.3.
Shown are the pH and the buffer agent (type and concentration) present
in the 2x binding buffers tested which comprise no additional salt.

| pH | Buffer agent Type | Buffer agent Concentration | Salt Type | Salt Concentration | Solid phase | Anion exchange group |
|---|---|---|---|---|---|---|
| 3 4 | formate | 100 mM | | none | mAnEx | monomeric (DEAPS) |
| 3.2 4 | lactate | 100 mM | | none | mAnEx | monomeric (DEAPS) |
| 3.65 4 | tartrate | 100 mM | | none | mAnEx | monomeric (DEAPS) |
| 3.5 4 | oxalate | 100 mM | | none | mAnEx | monomeric (DEAPS) |
| 4 | acetate | 100 mM | | none | mAnEx | monomeric (DEAPS) |
| 4 | citrate | 100 mM | | none | mAnEx | monomeric (DEAPS) |

Further details on the performed experimental steps were explained above.

Results

The results are shown in FIG. 6A-E below based on detection of the same target molecules as in Example 3.1.

Between the different buffer systems used in this experiment, at pH 4 lactate, formate, tartrate and oxalate buffers all had lower propensity to bind EVs than acetate or citrate (FIG. 6C), with only minor differences in ccfDNA recovery (FIG. 6B) and therefore better specificity for ccfDNA binding. Oxalate led to particularly low binding of EVs, specifically at pH 4 and in comparison to acetate. At the lower pH values, EV binding efficiency of the different buffer systems followed the pH values, with the lowest pH value showing less selectivity by showing increased EV binding (and exoRNA recovery) compared to higher pH values tested.

The experiments described here demonstrate conditions that allow the efficient capture of ccfDNA while leaving EVs and non-vesicular in the remaining binding mixture/supernatant, thereby allowing their isolation in a second step—using different particle surfaces (respectively, anion exchange groups), lower pH, and/or different buffer systems.

The invention claimed is:

1. A method for enriching extracellular DNA and sequentially extracellular vesicles and optionally extracellular RNA or for enriching extracellular vesicles and optionally extracellular RNA from a biological sample comprising extracellular DNA and extracellular vesicles, wherein the method comprises:

(a) preparing a binding mixture comprising
the biological sample,
a solid phase comprising anion exchange groups, and
an acidic binding buffer comprising a buffering agent,
and binding extracellular DNA to the solid phase comprising anion exchange groups;

(b) separating the solid phase with the bound extracellular DNA from the binding mixture to obtain a remaining binding mixture, wherein the remaining binding mixture comprises extracellular vesicles; and (c) processing the remaining binding mixture to enrich one or more biological targets of interest therefrom, wherein the processing comprises enriching extracellular vesicles and optionally extracellular RNA as biological targets of interest from the remaining binding mixture, wherein step (c) comprises enriching extracellular vesicles by binding to an anion exchange surface of a solid phase in the presence of a buffering agent, wherein the binding conditions used in step (a) for binding extracellular DNA differ from the binding conditions used in step (c) for binding extracellular vesicles and optionally extracellular RNA, and wherein the different binding conditions in step (a) and step (c) are achieved by at least one selected from the group consisting of:

(i) the extracellular vesicle binding mixture of step (c) has a lower pH than the extracellular DNA binding mixture of step (a);

(ii) the buffering agent introduced into the extracellular vesicle binding mixture in step (c) differs from the buffering agent in the extracellular DNA binding mixture in step (a) and (iii) the anion exchange surface of a solid phase in step (c) differs from the anion exchange groups of the solid phase in step (a).

2. The method according to claim 1 wherein when enriching extracellular vesicles and optionally extracellular RNA from a biological sample comprising extracellular vesicles and extracellular DNA, in step (a) at least extracellular DNA is bound as non-target biomolecule to the solid phase.

3. The method according to claim 1, wherein the pH of the acidic binding buffer is in a range of 2.5 to 6.5.

4. The method according to claim 1, wherein in step (a) the pH of the binding mixture corresponds to the pH of the acidic binding buffer or deviates by ≤1.5 pH units from the pH of the acidic binding buffer.

5. The method according to claim 1, wherein in step (a) the pH of the binding mixture is in a range of 2.5 to 6.5.

6. The method according to claim 1, wherein in step (a) the pH of the binding mixture is ≥4, ≥4.2 or ≥4.5.

7. The method according to claim 1, wherein in step (a) the pH of the binding mixture is lower than the pKa of the ionized form of the anion exchange groups of the solid phase.

8. The method according to claim 7, wherein the pH is at least 1 unit lower than the pKa.

9. The method according to claim 1, wherein the acidic binding buffer of step (a) comprises a carboxylic acid based buffering agent.

10. The method according to claim 1, wherein the buffering agent comprises a carboxylic acid and a salt of said carboxylic acid.

11. The method according to claim 6, wherein the acidic binding buffer of step (a) has a pH of ≥3.5, and wherein the buffering agent comprises a buffer component selected from the group consisting of citrate, oxalate, formate, propionate, lactate and tartrate.

12. The method according to claim 1, wherein in step (a) the binding mixture comprises the buffering agent originating from the acidic binding buffer in a concentration selected from the group consisting of:
(i) 0.5M or less;
(ii) at least 15 mM; and
(iii) the range of 15 mM to 250 mM.

13. The method according to claim 1, wherein the acidic binding buffer comprises a buffering salt as buffering agent and a non-buffering salt, and wherein the concentration of the non-buffering salt in the acidic binding buffer is 1M or less.

14. The method according to claim 13, wherein the non-buffering agent is an alkali metal salt.

15. The method according to claim 13, wherein the total salt concentration in the acidic binding buffer of step (a) is 1M or less.

16. The method according to claim 1, wherein the solid phase that is used in step (a) is particles.

17. The method according to claim 1, wherein the anion exchange groups comprise at least one primary, secondary or tertiary amino group.

18. The method according to claim 17, wherein the anion exchange group of the solid phase comprises one or more of primary, secondary and tertiary amines of the formula $(R)_3N, (R)_2NH, RNH_2$ and/or $X$—$(CH_2)_n$—$Y$ wherein
X is (R) 2N, RNH or $NH_2$,
Y is (R) 2N, RNH or $NH_2$,
R is independently an optionally substituted linear, branched or cyclic alkyl, alkenyl, alkynyl or aryl substituent which optionally comprises one or more heteroatoms, and
n is an integer in the range of from 0 to 20.

19. The method according to claim 17, wherein the anion exchange groups have at least one of the following characteristics:
(i) they comprise at least one amino group, wherein the amino group is part of a heterocyclic or heteroaromatic ring;
(ii) they comprise at least one amino group, wherein the amino group is part of an imidazole ring;
(iii) they comprise histidine or histamine;
(iv) they comprise at least one ionizable group having a pKa value of the ionized form within a range of 6 to about 13; or
(v) they comprise any one or more of
a trialkylamine group and/or a dialkylaminoalkyl group for extracellular cell-free DNA (cfDNA) binding;
a trialkylamine group and/or a dialkylaminoalkyl group for cfDNA binding wherein the alkyl groups independently comprise 1-6, 1 to 5 or 1 to 4 carbon atoms;
a trialkylamine group and/or a dialkylaminoalkyl group for cfDNA binding and no further ionizable groups for cfDNA binding;
a silane group;
a functionalization with trialkylsilanes; or a functionalization with N, N-dialkyl-3-aminoalkyl) trialkoxysilane, wherein the alkyl groups are selected from methyl-, ethyl-, propyl-, butyl-, or pentyl-groups.

20. The method according to claim 16, wherein the solid phase that is used in step (a) is magnetic particles, wherein the anion exchange groups of the magnetic particles comprise a trialkylamine group and wherein the acidic binding buffer has a pH of ≥3.5, and wherein the buffering agent comprises a buffer component selected from the group consisting of citrate, oxalate, formate, propionate, lactate and tartrate.

21. The method according to claim 1, wherein, after separating the solid phase with the bound extracellular DNA in step (b), the method further comprises:
(i) washing the extracellular DNA; and/or
(ii) recovering the extracellular DNA from the solid phase.

22. The method according to claim 1, wherein extracellular vesicles (EV) are enriched in step (c) by binding to a solid phase in combination with one or more of ultracentrifugation, ultrafiltration, gradients, affinity capture, or size exclusion chromatography.

23. The method according to claim 1, wherein the solid phase in step (c) is magnetic particles.

24. The method according to claim 23, wherein step (c) comprises enriching extracellular vesicles by binding to magnetic anion exchange particles, wherein enriching comprises:
(aa) contacting the remaining binding mixture collected after step (b) with magnetic anion exchange particles under extracellular vesicle binding conditions such that extracellular vesicles and optionally extracellular RNA bind to the anion exchange particles;
(bb) separating the anion exchange particles with the bound extracellular vesicles and optionally extracellular RNA; and
(cc) optionally further processing the anion exchange particles to enrich extracellular vesicles and optionally extracellular RNA.

25. The method according to claim 24, wherein the solid phase in step (a) is magnetic anion exchange particles, and wherein the different binding conditions in step (a) and step (c) are achieved by one or more conditions selected from the group consisting of:
(i) the charge density of the solid phase used in step (c) for binding extracellular vesicles is higher than the charge density of the solid phase used in step (a);
(ii) the EV binding mixture of step (c) (aa) has a lower pH than the cfDNA binding mixture of step (a);
(iii) the extracellular vesicle binding pH is in the range of 2.5 to 5;
(iv) the buffering agent in step (c) promotes binding of extracellular vesicles to the anion exchange groups of the solid phase;
(v) the buffering agent in step (c) is acetate; and
(vi) citrate is used in extracellular DNA binding step (a) and acetate is used in extracellular vesicle binding step (c).

26. The method according to claim 25, wherein preparing the extracellular vesicle binding conditions in step (c) (aa) comprises adding an acidic reagent, and wherein the binding conditions have at least one of the following characteristics:
(i) the pH of the acidic reagent is in the range of 2.5 to 5.5;
(ii) the acidic reagent comprises a buffering agent;
(iii) the acidic reagent comprises a carboxylic acid based buffer;

(iv) the extracellular binding mixture in step (c) (aa) comprises the buffering agent from the acidic reagent in a concentration of 100 mM to 1M; and (v) wherein the acidic reagent used in step (c) (aa) for extracellular vesicle binding has a lower pH than the acidic binding buffer of step (a) for cfDNA binding.

27. The method according claim 23, wherein step (c) comprises using magnetic particles comprising anion exchange groups selected from the group consisting of histamine, polyethyleneimine and poly-histidine for-EV extracellular vesicle binding.

28. The method according to claim 1, wherein the method further comprises lysing enriched extracellular vesicles thereby providing a lysate that comprises vesicular RNA and optionally enriching RNA from the lysate.

29. The method according to claim 1, wherein step (c) comprises enriching extracellular vesicles and optionally extracellular RNA from the remaining binding mixture collected after step (b), and further lysing the enriched extracellular vesicles to release the vesicular RNA and purifying RNA from the lysate, wherein the purified RNA comprises vesicular RNA and optionally non-vesicular RNA.

30. The method according to claim 24, wherein after separation step (bb), the solid phase with the bound extracellular vesicles is contacted with an acidic wash buffer that comprises a buffering agent, optionally wherein the acidic wash buffer does not comprise a detergent.

31. The method according to claim 30, further comprising recovering extracellular vesicles bound to the anion exchange solid phase by elution and/or lysis, wherein recovering comprises at least one of the following:

(i) providing a salt having a concentration of more than 1M;

(ii) increasing the pH such that the anion exchange groups are not positive charged;

(iii) increasing the pH to at least pH 8; and (iv) contacting the solid phase with the bound extracellular vesicles with a reagent comprising phenol and a chaotropic salt.

32. The method according to claim 1, wherein the method has one or more of the following characteristics:

(i) a protease is added at least in one of the following steps:

prior to step (a);
in step (a);
after step (b);
in step c); or
after step c);

(ii) wherein magnetic anion exchange particles are used in step (a) for binding extracellular DNA, and wherein at least steps (a) and (b) are performed in an automated manner using a robotic instrument;

(iii) wherein magnetic anion exchange particles are used in step (c) for binding extracellular vesicles;

(iv) wherein steps (a) to (c) are performed in an automated manner using a robotic instrument;

(vi) wherein enriched cfDNA and enriched extracellular cell-free RNA (cfRNA) are provided in separate fractions;

(vi) wherein enriched cfDNA and enriched cfRNA are provided in separate eluate fractions;

(vii) wherein the enriched cfDNA and enriched cfRNA are analyzed differently; and (viii) wherein enriching encompasses isolating or purifying the target molecule of interest.

33. The method according to claim 1, wherein the biological sample is:

(i) a body fluid or cell culture liquid;

(ii) derived from a body fluid or cell culture liquid;

(iii) a cell-free or cell-depleted body fluid sample or cell culture supernatant;

(iv) whole blood, plasma, serum, lymphatic fluid, urine, liquor, cerebrospinal fluid, synovial fluid, interstitial fluid, ascites, milk, bronchial lavage, saliva, amniotic fluid, semen/seminal fluid, body secretions, nasal secretions, vaginal secretions, wound secretions or excretions;

(v) derived from the following samples by removing cells: whole blood, plasma, serum, lymphatic fluid, urine, liquor, cerebrospinal fluid, synovial fluid, interstitial fluid, ascites, milk, bronchial lavage, saliva, amniotic fluid, semen/seminal fluid, body secretions, nasal secretions, vaginal secretions, wound secretions or excretions;

(vi) it is selected from plasma, serum or urine; or (vii) selected from cell-depleted or cell-free urine.

* * * * *